US011926653B2

(12) United States Patent
Sahenk

(10) Patent No.: US 11,926,653 B2
(45) Date of Patent: Mar. 12, 2024

(54) METHODS AND MATERIALS FOR NT-3 GENE THERAPY

(71) Applicant: RESEARCH INSTITUTE AT NATIONWIDE CHILDREN'S HOSPITAL, Columbus, OH (US)

(72) Inventor: Zarife Sahenk, Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 593 days.

(21) Appl. No.: 16/757,176

(22) PCT Filed: Oct. 19, 2018

(86) PCT No.: PCT/US2018/056765
§ 371 (c)(1),
(2) Date: Apr. 17, 2020

(87) PCT Pub. No.: WO2019/079755
PCT Pub. Date: Apr. 25, 2019

(65) Prior Publication Data
US 2020/0339960 A1   Oct. 29, 2020

Related U.S. Application Data

(60) Provisional application No. 62/741,335, filed on Oct. 4, 2018, provisional application No. 62/676,687, filed on May 25, 2018, provisional application No. 62/574,828, filed on Oct. 20, 2017.

(51) Int. Cl.
| | | |
|---|---|---|
| *C07K 14/475* | (2006.01) | |
| *A61K 48/00* | (2006.01) | |
| *A61P 25/00* | (2006.01) | |
| *C12N 15/86* | (2006.01) | |

(52) U.S. Cl.
CPC ........ *C07K 14/475* (2013.01); *A61K 48/0058* (2013.01); *A61K 48/0075* (2013.01); *A61P 25/00* (2018.01); *C12N 15/86* (2013.01); *C12N 2750/14143* (2013.01); *C12N 2830/15* (2013.01); *C12N 2830/50* (2013.01)

(58) Field of Classification Search
None
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 5,882,877 A | 3/1999 | Gregory et al. | |
| 6,258,595 B1 | 7/2001 | Gao et al. | |
| 6,566,118 B1 | 5/2003 | Atkinson et al. | |
| 10,336,828 B2 * | 7/2019 | Hwang | C07K 16/00 |
| 10,980,897 B2 | 4/2021 | Martin | |
| 2018/0340187 A1 | 11/2018 | Rodino-Klapac | |
| 2022/0364117 A1 | 11/2022 | Rodino-Klapac et al. | |

FOREIGN PATENT DOCUMENTS

| | | |
|---|---|---|
| WO | 1995/13365 A1 | 5/1995 |
| WO | 1995/13392 A1 | 5/1995 |
| WO | 1996/17947 A1 | 6/1996 |
| WO | 1997/06243 A1 | 2/1997 |
| WO | 1997/08298 A1 | 3/1997 |
| WO | 1997/09441 A2 | 3/1997 |
| WO | 1997/21825 A1 | 6/1997 |
| WO | 1998/09657 A2 | 3/1998 |
| WO | 1999/11764 A2 | 3/1999 |
| WO | 2001/83692 A2 | 11/2001 |
| WO | 2002/53703 A2 | 7/2002 |
| WO | WO-03/052051 A2 | 6/2003 |
| WO | 2010/089706 A1 | 8/2010 |
| WO | WO-2011/0094198 A1 | 8/2011 |
| WO | 2013/016352 A1 | 1/2013 |
| WO | WO-2015/0126927 A2 | 8/2015 |
| WO | WO-2016/0100963 A1 | 6/2016 |
| WO | WO-2017/072498 A1 | 5/2017 |
| WO | WO-2017/165806 A1 | 9/2017 |
| WO | 2017/180976 A1 | 10/2017 |
| WO | 2017/181011 A1 | 10/2017 |
| WO | 2017/181014 A1 | 10/2017 |
| WO | WO-2017/0173043 A1 | 10/2017 |

OTHER PUBLICATIONS

Lusby et al., "Nucleotide Sequence of the Inverted Terminal Repetition in Adeno-Associated Virus DNA" 34(2) Journal of Virology 402-409 (Year: 1980).*
Adlkofer et al., Heterozygous peripheral myelin protein 22-deficient mice are affected by a progressive demyelinating tomaculous neuropathy, J. Neurosci., 17(12):4662-4671 (1997).
Adlkofer et al., Hypermyelination and demyelinating peripheral neuropathy in Pmp22-deficient mice, Nat. Genet., 11:274-280 (1995).
Anzini et al., Structural abnormalities and deficient maintenance of peripheral nerve myelin in mice lacking the gap junction protein connexin 32, J. Neurosci., 17(12):4545-4551 (1997).
Auricchio et al., Exchange of surface proteins impacts on viral vector cellular specificity and transduction characteristics: the retina as a model, Hum. Mol. Genet., 10(26):3075-81 (2001).
Berkner, Expression of Heterologous Sequences in Adenoviral Vectors, Curr. Top. Micro. Immunol., 158:39-66 (1992).
Bosio et al., Galactosphingolipids and axono-glial interaction in myelin of the central nervous system, Cell Tissue Res., 292:199-210 (1998).

(Continued)

Primary Examiner — Nancy J Leith
(74) Attorney, Agent, or Firm — MARSHALL, GERSTEIN & BORUN LLP

(57) ABSTRACT

The present disclosure relates to recombinant adeno-associated vims (rAAV) delivery of a neurotrophin 3 (NT-3) polynucleotide. The disclosure provides rAAV and methods of using the rAAV for NT-3 gene therapy to improve muscle strength, stimulate muscle growth and to treat muscle wasting disorders, such as muscular dystrophy and Charcot-Marie-Tooth neuropathy.

26 Claims, 12 Drawing Sheets

Specification includes a Sequence Listing.

(56) References Cited

OTHER PUBLICATIONS

Carter, Adeno-associated virus vectors, Current Opinions in Biotechnology, 3(5):533-539 (1992).

Clark et al., A stable cell line carrying adenovirus-inducible rep and cap genes allows for infectivity titration of adeno-associated virus vectors, Gene. Therapy, 3(12):1124-1132 (1996).

Clark et al., Highly Purified Recombinant Adeno-Associated Virus Vectors Are Biologically Active and Free of Detectable Helper and Wild-Type Viruses, Hum. Gene. Ther., 10(6):1031-1039 (1999).

Cserjesi et al., Myogenin induces the myocyte-specific enhancer binding factor MEF-2 independently of other muscle-specific gene products, Mol. Cell Biol., 11(10):4854-4862 (1991).

Cunningham et al., mTOR controls mitochondrial oxidative function through a YY1-PGC-1a transcriptional complex, Nature, 450(7170):736-740 (2007).

De et al., High Levels of Persistent Expression of a1-Antitrypsin Mediated by the Nonhuman Primate Serotype rh. 10 Adeno-associated Virus Despite Preexisting Immunity to Common Human Adeno-associated Viruses, Mol. Ther., 13(1):67-76 (2006).

Duvel et al., Activation of a Metabolic Gene Regulatory Network Downstream of mTOR Complex 1, Molecular cell, 39(2):171-183 (2010).

Gao et al., Clades of Adeno-Associated Viruses Are Widely Disseminated in Human Tissues, J. Virol., 78(12):6381-6388 (2004).

Gao et al., Novel adeno-associated viruses from rhesus monkeys as vectors for human gene therapy, PNAS, 99(18):11854-11859 (2002).

Goins et al., Gene therapy for the treatment of chronic peripheral nervous system pain, Neurobiol. Dis., 48(2):255-270 (2012).

Helgren et al., Neurotrophin-3 administration attenuates deficits of pyridoxine-induced large-fiber sensory neuropathy, J. Neurosci., 17(1):372-382 (1997).

Hermonat et al., Use of adeno-associated virus as a mammalian DNA cloning vector: transduction of neomycin resistance into mammalian tissue culture cells, Proc. Natl. Acad. Sci. U.S.A., 81:6466-6470 (1984).

International Application No. PCT/US2018/056765, International Preliminary Report on Patentability, dated Apr. 30, 2020.

International Application No. PCT/US2018/056765, International Search Report and Written Opinion, dated Jan. 24, 2019.

Izumiya et al., Fast/Glycolytic Muscle Fiber Growth Reduces Fat Mass and Improves Metabolic Parameters in Obese Mice, Cell Metabolism, 7(2):159-172 (2008).

Johnson et al., Muscle creatine kinase sequence elements regulating skeletal and cardiac muscle expression in transgenic mice, Mol. Cell Biol., 9(8):3393-3399 (1989).

Kantor et al., Chapter Three—Methods for Gene Transfer to the Central Nervous System, Adv. Genet., 87:125-197 (2014).

Komyathy et al., Anterior tibialis CMAP amplitude correlations with impairment in CMT1A, Muscle & Nerve, 47(4):493-496 (2013).

Laplante et al., mTOR Signaling in Growth Control and Disease, Cell, 149(2):274-293 (2012).

Larsson et al., Effects of aging on shortening velocity and myosin isoform composition in single human skeletal muscle cells, Am. J. Physiol., 272(2):C638-C649 (1997).

Larsson et al., Maximum velocity of shortening in relation to myosin isoform composition in single fibres from human skeletal muscles, J. Physiol., 472(1):595-614 (1993).

Laughlin et al., Cloning of infectious adeno-associated virus genomes in bacterial plasmids, Gene., 23(1):65-73 (1983).

Lebkowski et al., Adeno-associated virus: a vector system for efficient introduction and integration of DNA into a variety of mammalian cell types, Mol. Cell. Biol., 8:349 (1988).

Lewis et al., High-Dosage Ascorbic Acid Treatment in Charcot-Marie-Tooth Disease Type 1A Results of a Randomized, Double-Masked, Controlled Trial, JAMA Neurology, 70(8):981-987 (2013).

Lupski et al., DNA duplication associated with Charcot-Marie-Tooth disease type 1A, Cell, 66:219-232 (1991).

Mader et al., A steroid-inducible promoter for the controlled overexpression of cloned genes in eukaryotic cells, Proc. Natl. Acad. Sci. U.S.A., 90(12):5603-5607 (1993).

Magy et al., Updating the classification of inherited neuropathies, Neurology, 90(10):e870-6 (2018).

Mannil et al., Selected items from the Charcot-Marie-Tooth (CMT) Neuropathy Score and secondary clinical outcome measures serve as sensitive clinical markers of disease severity in CMTIA patients, Neuromuscul. Disord., 24(11):1003-1017 (2014).

Marsic et al., Vector Design Tour de Force: Integrating Combinatorial and Rational Approaches to Derive Novel Adeno-associated Virus Variants, Molecular Therapy, 22(11):1900-1909 (2014).

Martini et al., Schachner M. Protein zero (P0)-deficient mice show myelin degeneration in peripheral nerves characteristic of inherited human neuropathies, Nat. Genet., 11:281-286 (1995).

Mason et al., Gene therapy for the peripheral nervous system: a strategy to repair the injured nerve?, Curr. Gene Ther., 11:75-89 (2011).

McLaughlin et al., Adeno-associated virus general transduction vectors: analysis of proviral structures, J. Virol., 62(6):1963-73 (1988).

Micallef et al., Effect of ascorbic acid in patients with Charcot-Marie-Tooth disease type 1A: a multicentre, randomised, double-blind, placebo-controlled trial, Lancet Neurol., 8(12):1103-1110 (2009).

Mizisin et al., Neurotrophin-3 reverses nerve conduction velocity deficits in streptozotocin-diabetic rats, J. Peripher. Nerv. Syst., 4(3-4):211-221 (1999).

Mizisin et al., NT-3 attenuates functional and structural disorders in sensory nerves o f galactose-fed rats, J. Neuropathol. Exp. Neurol., 57(9):803-813 (1998).

Mori et al., Two novel adeno-associated viruses from cynomolgus monkey: pseudotyping characterization of capsid protein, Virology, 330(2):375-383 (2004).

Muscat et al., Multiple 5'-flanking regions of the human alpha-skeletal actin gene synergistically modulate muscle-specific expression, Mol. Cell Biol., 7(11):4089-4099 (1987).

Muzyczka, Use of Adeno-Associated Virus as a General Transduction Vector for Mammalian Cells, Current Topics in Microbiology and Immunology, 158:97-129 (1992).

Nicks et al., Long-term Analyses of Innervation and Neuromuscular Integrity in the Trembler-J Mouse Model of Charcot-Marie-Tooth Disease, J. Neuropathol. Exp. Neural., 72(10):942-954 (2013).

Ojala et al., Adeno-Associated Virus Vectors and Neurological Gene Therapy, Neuroscientist, 21(1):84-98 (2015).

Pareyson et al., A multicenter, randomized, double-blind, placebo-controlled trial oflong-term ascorbic acid treatment in Charcot-Marie-Tooth disease type I A (CMT-TRIAAL): the study protocol [EudraCT No. 2006-000032-27], Pharmacological Research, 54:436-441 (2006).

Pareyson et al., Ascorbic acid in Charcot-Marie-Tooth disease type 1A (CMT-TRIAAL and CMT-TRAUK): a double-blind randomised trial, Lancet Neurol., 10(4):320-328 (2011).

Paul et al., Increased Viral Titer Through Concentration of Viral Harvests from Retroviral Packaging Lines, Human Gene Therapy, 4(5):609-615 (1993).

Perrin et al., An experimental rabies vaccine produced with a new BHK-21 suspension cell culture process: use of serum-free medium and perfusion-reactor system, Vaccine, 13(13):1244-1250 (1995).

Petruska et al., Intramuscular AAV delivery of NT-3 alters synaptic transmission to motoneurons in adult rats, Eur. J. Neurosci. 32:997-1005 (2010).

Choi, et al., Optimization of AAV expression cassettes to improve packaging capacity and transgene expression in neurons, Mol. Brain., 7(17), (Mar. 2014).

Piscosquito et al., Responsiveness of clinical outcome measures in Charcot-Marie-Tooth disease, European Journal of Neurology: The Official Journal of the European Federation of Neurological Societies, 22(12):1556-1563 (2015).

Ramer et al., Neurotrophin-3-mediated regeneration and recovery of proprioception following dorsal rhizotomy, Molecular and Cellular Neurosciences, 19:239-249 (2002).

(56) References Cited

OTHER PUBLICATIONS

Risson et al., Muscle inactivation of mTOR causes metabolic and dystrophin defects leading to severe myopathy, J. Cell. Biol., 187(6):859-874 (2009).
Sahenk et al., AAV1.NT-3 Gene Therapy for Charcot-Marie-Tooth Neuropathy, Mol. Ther., 22(3):511-21 (2014).
Sahenk et al., Abnormalities in the axonal cytoskeleton induced by a connexin32 mutation in nerve xenografts, J. Neurosci. Res., 51(2):174-184 (1998).
Sahenk et al., Effects of PMP22 duplication and deletions on the axonal cytoskeleton, Ann. Neurol., 45(1):16-24 (1999).
Sahenk et al., Evidence for impaired axonal regeneration in PMP22 duplication: studies in nerve xenografts, J. Peripher. Nerv. Syst., 8(2):116-127 (2003).
Sahenk et al., Freimer M. A novel PMP22 point mutation causing HNPP phenotype: studies on nerve xenografts, Neurology, 51(3):702-707 (1998).
Sahenk et al., NT-3 promotes nerve regeneration and sensory improvement in CMTIA mouse models and in patients, Neurology, 65(5):681-689 (2005).
Sahenk, Abnormal Schwann Cell-Axon Interactions in CMT Neuropathies: The Effects of Mutant Schwann Cells on the Axonal Cytoskeleton and Regeneration-Associated Myelination, Ann. N.Y. Acad. Sci., 883:415-426 (1999).
Salva et al., Design of Tissue-specific Regulatory Cassettes for High-level rAAV-mediated Expression in Skeletal and Cardiac Muscle, Mol. Ther., 15(2):320-329 (2007).
Samulski et al., Cloning of adeno-associated virus into pBR322: rescue of intact virus from the recombinant plasmid in human cells, Proc. Natl. Acad. Sci. U.S.A., 79(6):2077-2081 (1982).
Samulski et al., Helper-free stocks of recombinant adeno-associated viruses: normal integration does not require viral gene expression, J. Virol., 63(9):3822-3828 (1989).
Sanchez et al., Oligodendroglia regulate the regional expansion of axon caliber and local accumulation of neurofilaments during development independently of myelin formation, J. Neurosci., 16(16):5095-5105 (1996).
Saporta et al., Charcot-Marie-Tooth disease subtypes and genetic testing strategies, Ann. Neurol., 69(1):22-33 (2011).
Schecterson et al., Novel roles for neurotrophins are suggested by BDNF and NT-3 mRNA expression in developing neurons, Neuron, 9(3):449-463 (1992).
Schenpp et al., Highly Purified Recombinant Adeno-Associated Virus Vectors, Methods Mol. Med., 69:427-443 (2002).
Seidl et al., Evidence for the participation of nerve growth factor and its low-affinity receptor (p75NTR) in the regulation of the myogenic program, Journal of Cellular Physiology, 176(1):10-21 (1998).
Semenza et al., Hypoxia-inducible nuclear factors bind to an enhancer element located 3' to the human erythropoietin gene, Proc. Natl. Acad. Sci. U.S.A., 88(13):5680-5684 (1991).
Senapathy et al., Molecular cloning of adeno-associated virus variant genomes and generation of infectious virus by recombination in mammalian cells, J. Biol. Chem., 259:4661-4666 (1984).
Shy et al., Neuropathy progression in Charcot-Marie-Tooth disease type 1A, Neurology, 70(5):378-383 (2008).
Shy et al., Reliability and validity of the CMT neuropathy score as a measure of disability, Neurology, 64(7):1209-1214 (2005).
Solari et al., Reliability of clinical outcome measures in Charcot-Marie-Tooth disease, Neuromuscul. Disord., 18:19-26 (2008).
Srivastava et al., Nucleotide sequence and organization of the adeno-associated virus 2 genome, J. Virol., 45(2):555-564 (1983).
Sterne et al., Neurotrophin-3-enhanced Nerve Regeneration Selectively Improves Recovery of Muscle Fibers Expressing Myosin Heavy Chains 2b, J. Cell. Biol., 139(3):709-715 (1997).
Tauris et al., Proneurotrophin-3 may induce Sortilin-dependent death in inner ear neurons, Eur. J. Neurosci., 33(4):622-631 (2011).
Toscano et al., Dendritic Cells Transduced With Lentiviral Vectors Expressing VIP Differentiate Into VIP-secreting Tolerogenic-like DCs, Mol. Ther., 18(5):1035-1045 (2010).
Tratschin et al., A human parvovirus, adeno-associated virus, as a eucaryotic vector: transient expression and encapsidation of the procaryotic gene for chloramphenicol acetyltransferase, Mol. Cell. Biol., 4(10):2072-2081 (1984).
Tratschin et al., Adeno-associated virus vector for high-frequency integration, expression, and rescue of genes in mammalian cells, Mol. Cell. Biol., 5(11):3251-3260 (1985).
Tsai et al., Muscle-specific 4E-BP1 signaling activation improves metabolic parameters during aging and obesity, J. Clin. Invest., 125(8):2952-2964 (2015).
Verhamme et al., Oral high dose ascorbic acid treatment for one year in young CMTIA patients: a randomised, double-blind, placebo-controlled phase II trial, BMC Medicine, 7:70 (2009).
Waegh et al., Altered slow axonal transport and regeneration in a myelin-deficient mutant mouse: the trembler as an in vivo model for Schwann cell-axon interactions, J. Neurosci., 10(6):1855-1865 (1990).
Waegh et al., Local control of axonal properties by schwann cells: Neurofilaments and axonal transport in homologous and heterologous nerve grafts, J. Neurosci. Res., 30(1):201-212 (1991).
Waegh et al., Local modulation of neurofilament phosphorylation, axonal caliber, and slow axonal transport by myelinating Schwann cells, Cell, 68:451-463 (1992).
Wang et al., PrimerBank: a PCR primer database for quantitative gene expression analysis, 2012 update, Nucleic Acids Research, 40(Database issue):D1144-1149 (2012).
Weil et al., Behavioural alterations in male mice lacking the gene for D-aspartate oxidase, Behav. Brain Res., 171(2):295-302 (2006).
Weintraub et al., The myoD gene family: nodal point during specification of the muscle cell lineage, Science, 251:761-766 (1991).
Yalvac et al., AAV1.NT-3 gene therapy attenuates spontaneous autoimmune peripheral polyneuropathy, Gene. Ther., 23(1):95-102 (2016).
Yang et al., Neurotrophin 3 transduction augments remyelinating and immunomodulatory capacity of neural stem cells, Mol. Ther., 22(2):440-450 (2014).
Yin et al., Myelin-Associated Glycoprotein Is a Myelin Signal that Modulates the Caliber of Myelinated Axons, J. Neurosci., 18(6):1953-1962 (1998).
Mastroeni et al., Insulin-like growth factor-1 and neurotrophin-3 gene therapy prevents motor decline in an X-linked adrenoleukodystrophy mouse model, Ann Neura, 66(1):117-122 (2009).

* cited by examiner

Figure 8A. – Schematic map of injection sites for Cohort 1
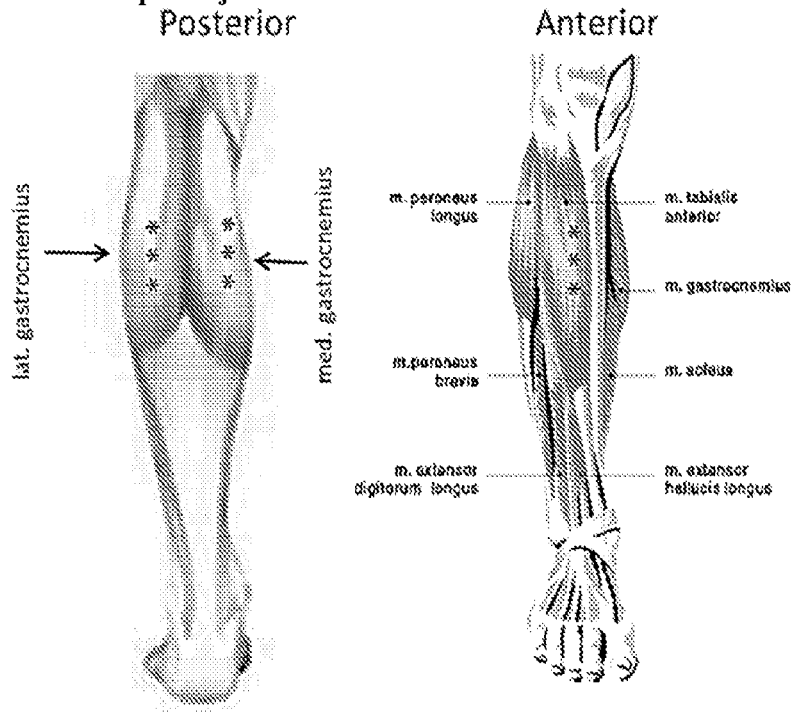
| Cohort | Volume per Injection | # Injections per muscle | Unilateral / Bilateral |
|---|---|---|---|
| 1 | 0.5 mL | 3-4 | Bilateral |
Figure 8B. – Schematic map of injection sites for Cohort 3
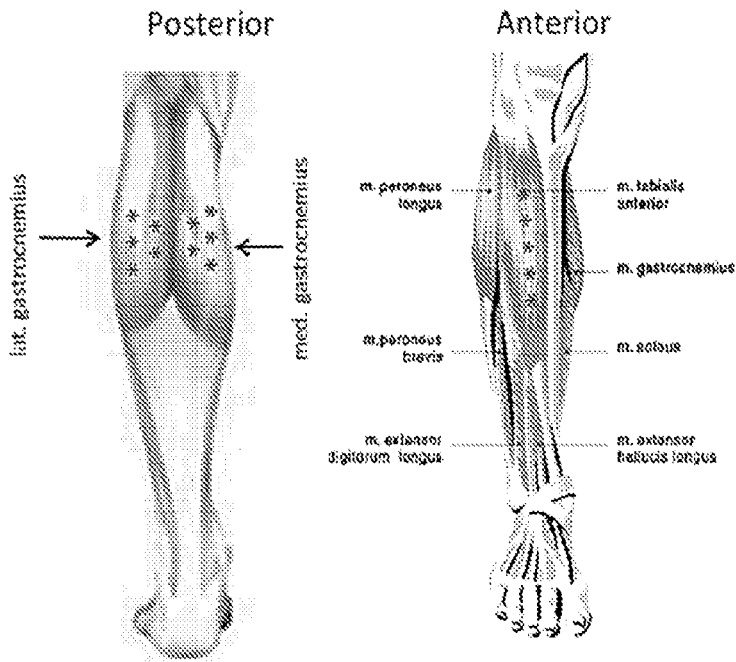
| Cohort | Volume per Injection | # Injections per muscle | Unilateral / Bilateral |
|---|---|---|---|
| 2 | 1.0 mL | ~5 | Bilateral |

Figure 9 sc pAAV.tMCK.NT3 vector full Sequence (5884bp) SEQ ID NO: 11

CAGCAGCTGCGCGCTCGCTCGCTCACTGAGGCCGCCCGGGCAAAGCCCGGGCGTCGGGCGACCTTTGGTC
GCCCGGCCTCAGTGAGCGAGCGAGCGCGCAGAGAGGGAGTGGggttaaccaattggcggccgcaaacttg
catgccccactacgggtctaggctgcccatgtaaggaggcaaggcctggggacacccgagatgcctggtt
ataattaaccccaacacctgctgcccccccccccccaacacctgctgcctgagcctgagcggttacccca
ccccggtgcctgggtcttaggctctgtacaccatggaggagaagctcgctctaaaaataaccctgtccct
ggtggatccactacgggtctatgctgcccatgtaaggaggcaaggcctggggacacccgagatgcctggt
tataattaaccccaacacctgctgcccccccccccccaacacctgctgcctgagcctgagcggttacccc
accccggtgcctgggtcttaggctctgtacaccatggaggagaagctcgctctaaaaataaccctgtccc
tggtggaccactacgggtctaggctgcccatgtaaggaggcaaggcctggggacacccgagatgcctggt
tataattaaccccaacacctgctgcccccccccccccaacacctgctgcctgagcctgagcggttaccccta
ccccggtgcctgggtcttaggctctgtacaccatggaggagaagctcgctctaaaaataaccctgtccct
ggtcctcctggggacagcccctcctggctagtcacaccctgtaggctcctctataacccaggggcac
aggggctgccccgggtcacctgcagaagttggtcgtgaggcactgggcaggtaagtatcaaggttacaa
gacaggtttaaggagaccaatagaaactgggcttgtcgagacagagaagactcttgcgtttctgataggc
acctattggtcttactgacatccactttgcctttctctccacaggtgtccactcccagttcaattacagc
gcgtggtacctgcagggatatCcaccATGTCCATCTTGTTTTATGTGATATTTCTCGCTTATCTCCGTGG
CATCCAAGGTAACAACATGGATCAAAGGAGTTTGCCAGAAGACTCGCTCAATTCCCTCATTATTAAGCTG
ATCCAGGCAGATATTTTGAAAAACAAGCTCTCCAAGCAGATGGTGGACGTTAAGGAAAATTACCAGAGCA
CCCTGCCCAAAGCTGAGGCTCCCCGAGAGCCGGAGCGGGGAGGGCCCGCCAAGTCAGCATTCCAGCCGGT
GATTGCAATGGACACCGAACTGCTGCGACAACAGAGACGCTACAACTCACCGCGGGTCCTGCTGAGCGAC
AGCACCCCCTTGGAGCCCCCGCCCTTGTATCTCATGGAGGATTACGTGGGCAGCCCCGTGGTGGCGAACA
GAACATCACGGCGGAAACGGTACGCGGAGCATAAGAGTCACCGAGGGGAGTACTCGGTATGTGACAGTGA
GAGTCTGTGGGTGACCGACAAGTCATCGGCCATCGACATTCGGGGACACCAGGTCACGGTGCTGGGGGAG
ATCAAAACGGGCAACTCTCCCGTCAAACAATATTTTTATGAAACGCGATGTAAGGAAGCCAGGCCGGTCA
AAAACGGTTGCAGGGGTATTGATGATAAACACTGGAACTCTCAGTGCAAAACATCCCAAACCTACGTCCG
AGCACTGACTTCAGAGAACAATAAACTCgtgggctggcggtggatacggatagacacgtcctgtgtgtgt
gccttgtcgagaaaaatcggaagaacatgaGGCGGCCGCGGGGATCCAGACATGATAAGATACATTGATG
AGTTTGGACAAACCACAACTAGAATGCAGTGAAAAAAATGCTTTATTTGTGAAATTTGTGATGCTATTGC
TTTATTTGTAACCATTATAAGCTGCAATAAACAAGTTAACAACAACAATTGCATTCATTTTATGTTTCAG
GTTCAGGGGGAGGTGTGGGAGGTTTTTTCggcgcgcctCTAGAGCATGGCTACGTAGATAAGTAGCATGG
CGGGTTAATCATTAACTACAAGGAACCCCTAGTGATGGAGTTGGCCACTCCCTCTCTGCGCGCTCGCTCG
CTCACTGAGGCCGGGCGACCAAAGGTCGCCCGACGCCCGGGCTTTGCCCGGGCGGCCTCAGTGAGCGAGC
GAGCGCGCCAGCTGGCGTAATAGCGAAGAGGCCCGCACCGATCGCCCTTCCCAACAGTTGCGCAGCCTGA
ATGGCGAATGGAATTCCAGACGATTGAGCGTCAAAATGTAGGTATTTCCATGAGCGTTTTTCCTGTTGCA
ATGGCTGGCGGTAATATTGTTCTGGATATTACCAGCAAGGCCGATAGTTTGAGTTCTTCTACTCAGGCAA
GTGATGTTATTACTAATCAAAGAAGTATTGCGACAACGGTTAATTTGCGTGATGGACAGACTCTTTTACT
CGGTGGCCTCACTGATTATAAAAACACTTCTCAGGATTCTGGCGTACCGTTCCTGTCTAAAATCCCTTTA
ATCGGCCTCCTGTTTAGCTCCCGCTCTGATTCTAACGAGGAAAGCACGTTATACGTGCTCGTCAAAGCAA
CCATAGTACGCGCCCTGTAGCGGCGCATTAAGCGCGGCGGGTGTGGTGGTTACGCGCAGCGTGACCGCTA
CACTTGCCAGCGCCCTAGCGCCCGCTCCTTTCGCTTTCTTCCCTTCCTTTCTCGCCACGTTCGCCGGCTT
TCCCCGTCAAGCTCTAAATCGGGGGCTCCCTTTAGGGTTCCGATTTAGTGCTTTACGGCACCTCGACCCC
AAAAAACTTGATTAGGGTGATGGTTCACGTAGTGGGCCATCGCCCTGATAGACGGTTTTTCGCCCTTTGA
CGTTGGAGTCCACGTTCTTTAATAGTGGACTCTTGTTCCAAACTGGAACAACACTCAACCCTATCTCGGT
CTATTCTTTTGATTTATAAGGGATTTTGCCGATTTCGGCCTATTGGTTAAAAAATGAGCTGATTTAACAA
AAATTTAACGCGAATTTTAACAAAATATTAACGTTTACAATTTAAATATTTGCTTATACAATCTTCCTGT
TTTTGGGGCTTTTCTGATTATCAACCGGGGTACATATGATTGACATGCTAGTTTTACGATTACCGTTCAT
CGATTCTCTTGTTTGCTCCAGACTCTCAGGCAATGACCTGATAGCCTTTGTAGAGACCTCTCAAAAATAG
CTACCCTCTCCGGCATGAATTTATCAGCTAGAACGGTTGAATATCATATTGATGGTGATTTGACTGTCTC
CGGCCTTTCTCACCCGTTTGAATCTTTACCTACACATTACTCAGGCATTGCATTTAAAATATATGAGGGT

Figure 9 Cont.

```
TCTAAAAATTTTTATCCTTGCGTTGAAATAAAGGCTTCTCCCGCAAAAGTATTACAGGGTCATAATGTTT
TTGGTACAACCGATTTAGCTTTATGCTCTGAGGCTTTATTGCTTAATTTTGCTAATTCTTTGCCTTGCCT
GTATGATTTATTGGATGTTGGAATTCCTGATGCGGTATTTTCTCCTTACGCATCTGTGCGGTATTTCACA
CCGCATATGGTGCACTCTCAGTACAATCTGCTCTGATGCCGCATAGTTAAGCCAGCCCCGACACCCGCCA
ACACCCGCTGACGCGCCCTGACGGGCTTGTCTGCTCCCGGCATCCGCTTACAGACAAGCTGTGACCGTCT
CCGGGAGCTGCATGTGTCAGAGGTTTTCACCGTCATCACCGAAACGCGCGAGACGAAAGGGCCTCGTGAT
ACGCCTATTTTTATAGGTTAATGTCATGATAATAATGGTTTCTTAGACGTCAGGTGGCACTTTTCGGGGA
AATGTGCGCGGAACCCCTATTTGTTTATTTTTCTAAATACATTCAAATATGTATCCGCTCATGAGACAAT
AACCCTGATAAATGCTTCAATAATATTGAAAAAGGAAGAGTATGAGTATTCAACATTTCCGTGTCGCCCT
TATTCCCTTTTTTGCGGCATTTTGCCTTCCTGTTTTTGCTCACCCAGAAACGCTGGTGAAAGTAAAAGAT
GCTGAAGATCAGTTGGGTGCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTATGTGGCGCGGTATTATC
CCGTATTGACGCCGGGCAAGAGCAACTCGGTCGCCGCATACACTATTCTCAGAATGACTTGGTTGAGTAC
TCACCAGTCACAGAAAAGCATCTTACGGATGGCATGACAGTAAGAGAATTATGCAGTGCTGCCATAACCA
TGAGTGATAACACTGCGGCCAACTTACTTCTGACAACGATCGGAGGACCGAAGGAGCTAACCGCTTTTTT
GCACAACATGGGGGATCATGTAACTCGCCTTGATCGTTGGGAACCGGAGCTGAATGAAGCCATACCAAAC
GACGAGCGTGACACCACGATGCCTGTAGCAATGGCAACAACGTTGCGCAAACTATTAACTGGCGAACTAC
TTACTCTAGCTTCCCGGCAACAATTAATAGACTGGATGGAGGCGGATAAAGTTGCAGGACCACTTCTGCG
CTCGGCCCTTCCGGCTGGCTGGTTTATTGCTGATAAATCGGAGCCGGTGAGCGTGGGTCTCGCGGTATC
ATTGCAGCACTGGGGCCAGATGGTAAGCCCTCCCGTATCGTAGTTATCTACACGACGGGGAGTCAGGCAA
CTATGGATGAACGAAATAGACAGATCGCTGAGATAGGTGCCTCACTGATTAAGCATTGGTAACTGTCAGA
CCAAGTTTACTCATATATACTTTAGATTGATTTAAAACTTCATTTTTAATTTAAAAGGATCTAGGTGAAG
ATCCTTTTTGATAATCTCATGACCAAAATCCCTTAACGTGAGTTTTCGTTCCACTGAGCGTCAGACCCCG
TAGAAAAGATCAAAGGATCTTCTTGAGATCCTTTTTTTCTGCGCGTAATCTGCTGCTTGCAAACAAAAAA
ACCACCGCTACCAGCGGTGGTTTGTTTGCCGGATCAAGAGCTACCAACTCTTTTTCCGAAGGTAACTGGC
TTCAGCAGAGCGCAGATACCAAATACTGTCCTTCTAGTGTAGCCGTAGTTAGGCCACCACTTCAAGAACT
CTGTAGCACCGCCTACATACCTCGCTCTGCTAATCCTGTTACCAGTGGCTGCTGCCAGTGGCGATAAGTC
GTGTCTTACCGGGTTGGACTCAAGACGATAGTTACCGGATAAGGCGCAGCGGTCGGGCTGAACGGGGGT
TCGTGCACACAGCCCAGCTTGGAGCGAACGACCTACACCGAACTGAGATACCTACAGCGTGAGCTATGAG
AAAGCGCCACGCTTCCCGAAGGGAGAAAGGCGGACAGGTATCCGGTAAGCGGCAGGGTCGGAACAGGAGA
GCGCACGAGGGAGCTTCCAGGGGGAAACGCCTGGTATCTTTATAGTCCTGTCGGGTTTCGCCACCTCTGA
CTTGAGCGTCGATTTTTGTGATGCTCGTCAGGGGGCGGAGCCTATGGAAAAACGCCAGCAACGCGGCCT
TTTTACGGTTCCTGGCCTTTTGCTGGCCTTTTGCTCACATGTTCTTTCCTGCGTTATCCCCTGATTCTGT
GGATAACCGTATTACCGCCTTTGAGTGAGCTGATACCGCTCGCCGCAGCCGAACGACCGAGCGCAGCGAG
TCAGTGAGCGAGGAAGCGGAAGAGCGCCCAATACGCAAACCGCCTCTCCCCGCGCGTTGGCCGATTCATT
AATG
```

METHODS AND MATERIALS FOR NT-3 GENE THERAPY

CROSS-REFERENCE TO RELATED APPLICATIONS

This application claims priority to U.S. Provisional Patent Application No. 62/574,828, filed on Oct. 20, 2017, U.S. Provisional Patent Application No. 62/676,687, filed May 25, 2018 and U.S. Provisional Patent Application No. 62/741,335, filed on Oct. 4, 2018, the disclosures of which are hereby incorporated by reference in their entirety.

STATEMENT OF U.S. GOVERNMENTAL INTEREST

This invention was made with government support under grant numbers NS105986 and U01-NS066914, awarded by the National Institutes of Health. The government has certain rights in the invention.

INCORPORATION BY REFERENCE OF THE SEQUENCE LISTING

This application contains, as a separate part of disclosure, a Sequence Listing in computer-readable form (filename: 53122A_Seqlisting.txt 17,328 bytes-ASCII text file; created Oct. 18, 2018) which is incorporated by reference herein in its entirety.

FIELD

The present disclosure relates to recombinant adeno-associated virus (rAAV) delivery of a neurotrophin 3 (NT-3) polynucleotide. The disclosure provides rAAV and methods of using the rAAV for NT-3 gene therapy to improve muscle strength, stimulate muscle growth and to treat neuropathies and muscle wasting disorders, such as Charcot-Marie-Tooth neuropathy.

BACKGROUND

Recent studies have demonstrated that neurotrophin 3 (NT-3) is a versatile molecule with previously unknown or underappreciated features. In addition to its well-recognized effects on peripheral nerve regeneration and Schwan cells (SCs), NT-3 has anti-inflammatory and immunomodulatory effects. Yang et al., Mel Titer, 22(2):440-450 (2014). It has been recently demonstrated that NT-3 is capable of attenuating spontaneous autoimmune peripheral polyneuropathy in the rodent model of chronic inflammatory demyelinating peripheral nerve disorder that occurs in humans. Yalvac et al., Gene therapy, 23(1):95-102 (2015).

Charcot-Marie-Tooth (CMT) neuropathies are the most common hereditary neuropathies. CMT1 includes five types of CMT that are caused by four genes when mutated. This group includes the majority of people with CMT. These genes are associated with SCs and the myelin sheath surrounding the axon, although they interact in different ways and thus are phenotypically heterogeneous. CMT type 1A is the result of a DNA duplication on chromosome 17p11 encompassing PMP22 gene which leads to development of the classic CMT1 phenotype. Patients develop clinical signs in the first two decades of life causing significant disabilities requiring ambulatory aids. In these patients, peripheral nerve regeneration is incomplete due to prolonged axotomy and denervation which occurs as part of the chronic neuropathy.

NT-3 is a trophic factor secreted by Schwann cells (SCs) that supports nerve regeneration. The ability of denervated SCs to survive is crucial for nerve regeneration as SCs provide both growth factors and basal lamina, scaffoldings that promote axonal growth. Prolonged denervation leads to a decreased regenerative capacity related to reduced expression of regeneration-associated SC molecules (neurotrophic factors (NTFs) and their receptors) resulting in atrophy of the denervated SCs, breakdown of the bands of Bungner, and loss of SC basal lamina scaffoldings.

Previous studies have shown that NT-3 gene therapy in the Trembled (TrJ) mouse model of Charcot-Marie-Tooth (CMT) neuropathy not only improved nerve regeneration with accompanied increases in SC number, myelinated fiber densities and myelin thickness, but also increased the muscle fiber diameter, illustrated in the anterior and posterior compartment muscles in the hind limbs. Sahenk et al., Mol Ther, 22(3):511-521 (2014). Previous studies have shown that neuropathic phenotypes are known to produce diverse changes in skeletal muscle, including a switch from fast type II, to slow type I fibers. In the TrJ mice, the extensor digitalis longus, primarily composed of fast-type fibers was found to have significantly higher percentage of slow fibers compared to wild type (WT) and the percentage of type I fibers in the soleus muscle dramatically increased with age. Nicks et al., J Neuropathol Exp Neurol, 72(10): 942-954 (2013). Interestingly, aging is also paralleled by similar changes in the slow fiber proportion, both in humans and other mammals. Larsson L, Moss R, J Physiol., 472: 595-614 (1993); Larsson et al., Am J Physiol., 272:C638-C649 (1997).

CMT1A, inherited as an autosomal dominant condition, is the most common type of CMT. Most often it is caused by a 1.5 Mb duplication at 17p11.2 including the peripheral myelin protein 22 (PMP22) gene, created by unequal crossing over of homologous chromosomes (1). This is a slowly progressive disease without known treatment. Symptoms most often start in the first two decades. Pes cavus and hammer toes are present. Ambulatory aids such as ankle foot orthoses are required. Less frequently, severe childhood cases may be wheelchair or ventilator-dependent. Typically, 90% of patients have motor nerve conduction velocity (NCV) in the ulnar nerve between 16 and 35 m/s or less (2). Even though the genetic defect primarily involves Schwann cells (SCs), the clinical electrophysiological picture is a length-dependent sensorimotor demyelinating neuropathy. The clinical picture is significantly influenced by axonal degeneration resulting from impaired Schwann cell (SC)-axon interactions (3).

Currently there is no treatment for this condition. Ascorbic acid supplements have been highly touted to help, but multiple studies have shown no benefit. Both low dose (1-2 g/day) (4-6) and high dose therapy (3-4 g/day) have not proved to be beneficial (6,7). Initially a human trial of NT-3 showed clinical efficacy after 24 weeks of treatment accompanied by increased numbers of myelinated nerve fibers in post-treatment sural nerve biopsies (8). In the Tr$^J$ mouse subcutaneous NT-3 treatment improved axonal regeneration and enhanced the myelination. However, the short serum half-life of NT-3 proved to be a major obstacle for continued subcutaneous administration and this product was discontinued.

A large number of musculoskeletal diseases have been shown to lead to a decrease in muscle strength. These include, but are not limited to, inherited or recessive myopathies (such as muscular dystrophies), muscle-wasting diseases (such as cachexia that may be the result from underlying illnesses such as acquired immunodeficiency diseases (AIDS), rheumatoid arthritis, cancer, chronic obstructive pulmonary disease (COPD), and cirrhosis), conditions of muscle atrophy or attenuation (such as sarcopenia that may be the result of aging), protracted disuse (such as paralysis, coma, extended bed rest, and ICU stay), weakness induced by surgery (such as joint replacement surgery), drug-induced myopathy and rhabdomyolysis. Muscle pathology of these diseases and conditions are mediated, in part or in whole, by a combination of immune, inflammatory, and fibrotic responses. Agents capable of blocking these responses and/or stimulating regeneration of the damaged tissue would be capable of slowing or reversing disease progression in these disorders.

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_001862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

There is a need for developing therapies for CMT neuropathies and other muscle wasting disorders. The invention provides gene therapy methods of delivering NT-3 for the treatment of CMT neuropathies and other muscle wasting disorders.

SUMMARY

The disclosure provides methods of stimulating muscle growth in a subject. The method comprises administering a therapeutically effective amount of neurotrophin-3 (NT-3), pro-NT-3, or an effective fragment thereof, or a nucleic acid encoding NT-3, pro-NT-3, or an effective fragment thereof, to a subject in need. The disclosure describes the novel effect of NT-3, its ability to directly influence the protein synthesis and metabolic remodeling in neurogenic muscle.

In various embodiments of the disclosure, the NT-3, pro-NT-3, or an effective fragment thereof, or a nucleic acid encoding NT-3 or an effective fragment thereof of the disclosure, is administered intramuscularly.

In any of the methods of the disclosure, the nucleic acid encoding NT-3 or an effective fragment thereof, is administered using a viral vector. In certain embodiments, the viral vector is the adeno-associated virus (AAV) vector. In related embodiments, the nucleic acid encoding NT-3 or an effective fragment thereof of the disclosure, is operatively linked to a muscle-specific promoter, such as a triple muscle-specific creatine kinase promoter. In various embodiments, the nucleic acid encoding NT-3 or an effective fragment thereof of the disclosure, comprises SEQ ID NO: 1.

The disclosure provides for nucleic acids comprising, in order from 5' to 3': (i) a first AAV2 inverted terminal repeat sequence (ITR); (ii) a muscle creatine kinase promoter/enhancer sequence set out in nucleotides 147-860 of SEQ ID NO: 11; (iii) a nucleotide sequence encoding a human NT-3 polypeptide; and (iv) a second AAV2 ITR sequence; wherein the human NT-3 polypeptide has an amino acid sequence that is at least 90% identical to SEQ ID NO: 2 or is 100% identical to SEQ ID NO: 2, or is encoded by a nucleotide sequence 90% identical to nucleotides 1077-1850 of SEQ ID NO: 11 or 100% identical to nucleotides 1077-1850 of SEQ ID NO: 11.

In some embodiments, the nucleic acids of the disclosure further comprise 3' to the promoter/enhancer, a chimeric intron set out in nucleotides 892-1024 of SEQ ID NO: 11. In addition, the nucleic acids of the disclosure can further comprise 3' to said nucleotide sequence encoding a human NT-3 polypeptide, a SV40 polyadenyation signal set out in nucleotides 1860-2059 of SEQ ID NO: 11.

Any of the nucleic acids of the disclosure can comprise one or more inverted terminal repeat (ITR) sequences. For example, the nucleic can comprise a first ITR whiich set out in nucleotides 7-112 of SEQ ID NO: 11, and/or a second ITR which is set out in nucleotides 2121-2248 of SEQ ID NO: 11.

In some embodiments, the nucleic acids comprise an scAAV1.tMCK.NTF3 genome that is at least 90% identical to the nucleotide sequence set out in SEQ ID NO: 11.

The disclosure also provides for recombinant adeno-associated virus particles (rAAV) comprising any of the nucleic acids of the disclosure, wherein the rAAV is infectious. The rAAV particles can be any rAAV serotype, such as AAV-1, AAV-2, AAV-3, AAV-4, AAV-5, AAV-6, AAV-7, AAV-8, AAV-9, AAV-10, AAV-11, or AAVrh.74. In addition, in any of the rAAV particles of the invention, the AAV DNA in the rAAV genome is from AAV-1.

The disclosure also provides for compositions comprising the rAAV of the disclosure and a pharmaceutically acceptable carrier. For example, these compositions are formulated to treat a muscle wasting disorder or neuropathy in a subject in need thereof or these compositions are formulated to stimulate muscle growth in a subject in need thereof.

In one embodiment, the disclosure provides for methods of treating a muscle wasting disorder or neuropathy in a human subject in need thereof comprising the step of administering to the human subject a nucleic acid encoding the NT-3 polypeptide; wherein a) the nucleic acid comprises a nucleotide sequence that is 90% identical to the nucleotide sequence of SEQ ID NO: 1, b) the nucleic acid comprises the nucleotide sequence of SEQ ID NO: 1; c) the nucleic acid comprises a nucleic acid sequence encoding an amino acid sequence that is at least 90% identical to SEQ ID NO:2 or is 100% identical to SEQ ID NO: 2, d) the nucleic acid encoding the NT-3 polypeptide is any of the nucleic acids of the disclosure, e) the nucleic acid encoding the NT-3 polypeptide is the recombinant adeno-associated virus (rAAV) scAAV1.tMCK.NTF3, and the rAAV is administered at a dose that results in sustained expression of a low concentration of NT-3 polypeptide, f) the nucleic acid encoding the NT-3 polypeptide is the recombinant adeno-associated virus (rAAV) scAAV1.tMCK.NTF3, the route of administration is an intramuscular route and the dose of the rAAV administered is about 1.5×1012 vg/kg to about 6.5×1012 vg/kg, g) the nucleic acid encoding the NT-3 polypeptide is the recombinant adeno-associated virus (rAAV) scAAV1.tMCK.NTF3, the route of administration is an intramuscular route and the dose of the rAAV administered is about 2×1012 vg/kg to about 6×1012 vg/kg, h) the nucleic acid encoding the NT-3 polypeptide is the recombinant adeno-associated virus (rAAV) scAAV1.tMCK.NTF3, the route of administration is an intramuscular route and the dose of the rAAV administered is about 2×1012 vg/kg, i) the nucleic acid encoding the NT-3 polypeptide is the recombinant adeno-associated virus (rAAV) scAAV1.tMCK.NTF3, the route of administration is an intramuscular route and the dose of the rAAV administered is about 4×1012 vg/kg, j) the nucleic acid encoding the NT-3 polypeptide is the recombinant adeno-associated virus (rAAV) scAAV1.tMCK.NTF3, the route of administration is an intramuscular route and the dose of the rAAV administered is about 6×1012 vg/kg, k) the nucleic acid encoding the NT-3 polypeptide is the recombinant adeno-associated virus (rAAV) scAAV1.tMCK.NTF3, the route of administration is an intramuscular injection at a concentration of about 2×1013 vg/ml administered using 3 to 6 injections per muscle of about 0.5 to 1 ml, or 1) the nucleic acid encoding the NT-3 polypeptide is the recombinant adeno-associated virus (rAAV) scAAV1.tMCK.NTF3, the route of administration is an intramuscular injection at a concentration of about 2×10$^{13}$ vg/ml administered using multiple injections at a total volume of about 5 to 14 ml.

In another embodiment, the diclsoure provides for methods of improving muscle strength or stimulating muscle growth in a human subject in need thereof comprising the step of administering to the human subject a nucleic acid encoding the NT-3 polypeptide; wherein a) the nucleic acid comprises a nucleotide sequence that is 90% identical to the nucleotide sequence of SEQ ID NO: 1, b) the nucleic acid comprises the nucleotide sequence of SEQ ID NO: 1; c) the nucleic acid comprises a nucleic acid sequence encoding an amino acid sequence that is at least 90% identical to SEQ ID NO: 2 or is 100% identical to SEQ ID NO: 2, d) the nucleic acid encoding the NT-3 polypeptide is any of the nucleic acids of the disclosure, e) the nucleic acid encoding the NT-3 polypeptide is the recombinant adeno-associated evirus (rAAV) scAAV1.tMCK.NTF3, and the rAAV is administered at a dose that results in sustained expression of a low concentration of NT-3 polypeptide, f) the nucleic acid encoding the NT-3 polypeptide is the recombinant adeno-associated virus (rAAV) scAAV1.tMCK.NTF3, the route of administration is an intramuscular route and the dose of the rAAV administered is about 1.5×1012 vg/kg to about 6.5×1012 vg/kg, g) the nucleic acid encoding the NT-3 polypeptide is the recombinant adeno-associated virus (rAAV) scAAV1.tMCK.NTF3, the route of administration is an intramuscular route and the dose of the rAAV administered is about 2×1012 vg/kg to about 6×1012 vg/kg, h) the nucleic acid encoding the NT-3 polypeptide is the recombinant adeno-associated virus (rAAV) scAAV1.tMCK.NTF3, the route of administration is an intramuscular route and the dose of the rAAV administered is about 2×1012 vg/kg, i) the nucleic acid encoding the NT-3 polypeptide is the recombinant adeno-associated virus (rAAV) scAAV1.tMCK.NTF3, the route of administration is an intramuscular route and the dose of the rAAV administered is about 4×1012 vg/kg, j) the nucleic acid encoding the NT-3 polypeptide is the recombinant adeno-associated virus (rAAV) scAAV1.tMCK.NTF3, the route of administration is an intramuscular route and the dose of the rAAV administered is about 6×1012 vg/kg, k) the nucleic acid encoding the NT-3 polypeptide is the recombinant adeno-associated virus (rAAV) scAAV1.tMCK.NTF3, the route of administration is an intramuscular injection at a concentration of about 2×1013 vg/ml administered using 3 to 6 injections per muscle of about 0.5 to 1 ml, or 1) the nucleic acid encoding the NT-3 polypeptide is the recombinant adeno-associated virus (rAAV) scAAV1.tMCK.NTF3, the route of administration is an intramuscular injection at a concentration of about 2×10$^{13}$ vg/ml administered using multiple injections at a total volume of about 5 to 14 ml.

In any of the method of the disclosure, the nucleic acid is administered using a viral vector, such as adeno-associated virus vector. Any of the methods of the disclosure can be carried out with a nucleic acid that is is operatively linked to a muscle-specific promoter, such the muscle-specific creatine kinase (MCK) promoter. In addition, any of the methods of the disclosure can be carried out with the scAAV1.tMCK.NTF3 comprises the NT-3 gene cassette set out in SEQ ID NO: 11.

In some embodiments, the disclosure provides for gene therapy methods using human neurotrophin-3 gene (NTF3) under control of a muscle specific promoter, tMCK, using a scAAV1 vector, a self-complementary AAV1 serotype. In particular, the disclosure provides for methods of treating subjects diagnosed with a muscle wasting disorder or a neuropathy comprising administering an AAV vector expressing NT-3. In particular, the methods comprise administering the construct scAAV1.tMCK.NTF3 via intramuscular (IM) injection in the gastrocnemius and tibialis anterior muscle. For example, intramuscular delivery of an AAV vector expressing NT-3, e.g. scAAV1.tMCK.NTF3, initiates local production and secretion of NT-3 into the circulation thereby promoting nerve myelination and fiber regeneration leading to stabilization of the CMT disease phenotype. More particularly, the disclosure provides for methods of administering scAAV1.tMCK.NTF3 at a dose of at about $2 \times 10^{12}$ vg/kg or at a dose of about $6 \times 10^{12}$ vg/kg. The scAAV1.tMCK.NTF3 comprises the NT-3 gene cassette set out in SEQ ID NO: 11.

The disclosure also provides for methods of administering AAV vector expressing NT-3 as a surrogate gene therapy for treating a muscle wasting disorder or a neuropathy. NT-3 has a short half-life and the methods of the disclosure comprise administering an AAV vector for a sustained release of NT-3 protein, even though the subject expresses endogenous NT-3 protein. As a surrogate gene therapy, the administration of the AAV vector provides sustained delivery of the NT-3 protien by sustained secretion by muscle cells. This continuous sustained low circulating level of NT-3 protein provides a therapeutic effect with a minimal risk of toxicity. Systemic production of NT-3 by gene therapy is also a more convenient and cost effective therapy option when compared to repeated injections of a purified NT-3 peptide.

The disclosure provides for methods of treating a muscle wasting disorder or neuropathy in a human subject in need thereof comprising the step of administering to the human subject a dose of recombinant adeno-associated virus (rAAV) scAAV1.tMCK.NTF3 that results in sustained expression of a low concentration of NT-3 protein.

The disclosure also provides for methods of stimulating muscle growth in a human subject in need thereof comprising the step of administering to the human subject a dose of recombinant adeno-associated virus (rAAV) scAAV1.tMCK.NTF3 that results in sustained expression of a low concentration of NT-3 protein.

In one embodiment, the disclosure provides for methods of treating a muscle wasting disorder or neuropathy in a human subject in need thereof comprising the step of administering to the human subject a recombinant adeno-associated virus (rAAV) scAAV1.tMCK.NTF3, wherein the route of administration is an intramuscular route and the dose of the rAAV administered is about $1.0 \times 10^{12}$ vg/kg to about $7 \times 10^{12}$ vg/kg, or about $1.5 \times 10^{12}$ vg/kg to about $6.5 \times 10^{12}$ vg/kg, or about $2 \times 10^{12}$ vg/kg to about $6 \times 10^{12}$ vg/kg.

In another embodiment, the disclosure provides for methods of treating a muscle wasting disorder or neuropathy in a human subject in need thereof comprising the step of administering to the human subject a recombinant adeno-associated virus (rAAV) scAAV1.tMCK.NTF3, wherein the route of administration is an intramuscular route and the dose of the rAAV administered is about $1.0 \times 10^{12}$ vg/kg, or about $1.5 \times 10^{12}$ vg/kg, or about $2 \times 10^{12}$ vg/kg, or about $3 \times 10^{12}$ vg/kg, or about $4 \times 10^{12}$ vg/kg, or about $5 \times 10^{12}$ vg/kg, or about $6 \times 10^{12}$ vg/kg, or about $7 \times 10^{12}$ vg/kg, or about $8 \times 10^{12}$ vg/kg, or about $9 \times 10^{12}$ vg/kg, or about $1 \times 10^{13}$ vg/kg.

In another embodiment, the disclosure provides for methods of treating a muscle wasting disorder or neuropathy in human subject in need thereof comprising the step of administering to the human subject a recombinant adeno-associated virus (rAAV) scAAV1.tMCK.NTF3, wherein the route of administration is an intramuscular injection at a concentration of about $1 \times 10^{13}$ vg/ml. For example, the rAAV is administered using 3 to 6 injections per muscle respectively, e.g. each injection volume will be 0.5 to 1 ml, wherein a total of 5 mL to 14 mL of vector is administered to the medial and lateral heads of the gastroc and tibialis anterior muscle in each leg.

In an exemplary embodiment, the disclosure provides for methods of treating a muscle wasting disorder or neuropathy in a human subject in need thereof comprising the step of administering to the human subject a recombinant adeno-associated virus (rAAV) scAAV1.tMCK.NTF3, wherein the route of administration is an intramuscular injection at a concentration of about $2 \times 10^{13}$ vg/ml administered using 3 to 6 injections per muscle respectively (each injection volume will be 0.5 to 1 ml). A total of 5 mL to 14 mL of vector is administered to the medial and lateral heads of the gastroc and tibialis anterior muscle in each leg.

In one embodiment, the provides for methods of improving muscle strength or stimulating muscle growth in a human subject in need thereof comprising the step of administering to the human subject a recombinant adeno-associated virus (rAAV) scAAV1.tMCK.NTF3, wherein the route of administration is an intramuscular route and the dose of the rAAV administered is about $1.0 \times 10^{12}$ vg/kg to about $7 \times 10^{12}$ vg/kg, or about $1.5 \times 10^{12}$ vg/kg to about $6.5 \times 10^{12}$ vg/kg, or about $2 \times 10^{12}$ vg/kg to about $6 \times 10^{12}$ vg/kg.

In another embodiment, the disclosure provides for methods of improving muscle strength or stimulating muscle growth in a human subject in need thereof comprising the step of administering to the human subject a recombinant adeno-associated virus (rAAV) scAAV1.tMCK.NTF3, wherein the route of administration is an intramuscular route and the dose of the rAAV administered is about $1.0 \times 10^{12}$ vg/kg, or about $1.5 \times 10^{12}$ vg/kg, or about $2 \times 10^{12}$ vg/kg, or about $3 \times 10^{12}$ vg/kg, or about $4 \times 10^{12}$ vg/kg, or about $5 \times 10^{12}$ vg/kg, or about $6 \times 10^{12}$ vg/kg, or about $7 \times 10^{12}$ vg/kg, or about $8 \times 10^{12}$ vg/kg, or about $9 \times 10^{12}$ vg/kg, or about $1 \times 10^{13}$ vg/kg.

In an exemplary embodiment, the disclosure provides for methods of improving muscle strength or stimulating muscle growth in human subject in need thereof comprising the step of administering to the human subject a recombinant adeno-associated virus (rAAV) scAAV1.tMCK.NTF3, wherein the route of administration is an intramuscular injection at a concentration of about $1 \times 10^{13}$ vg/ml. For example, the rAAV is administered using 3 to 6 injections per muscle respectively, e.g. each injection volume will be 0.5 to 1 ml, wherein a total of 5 mL to 14 mL of vector is administered to the medial and lateral heads of the gastroc and tibialis anterior muscle in each leg.

In an exemplary embodiment, the disclosure provides for methods of improving muscle strength or stimulating muscle growth in human subject in need thereof comprising the step of administering to the human subject a recombinant adeno-associated virus (rAAV) scAAV1.tMCK.NTF3, wherein the route of administration is an intramuscular injection at a concentration of about $1 \times 10^{13}$ vg/ml administered at low dose ($2 \times 10^{12}$ vg/kg per patient) and at high dose ($6 \times 10^{12}$ vg/kg per patient) using 3 to 6 injections per muscle respectively (each injection volume will be 0.5 to 1 ml). A total of 5 mL to 14 mL of vector is administered to the medial and latera heads of the gastroc and tibialis anterior muscle in each leg.

In any of the methods of the disclosure, wherein the route of administration of scAAV1.tMCK.NTF3 is an intramuscular bilateral injection to the medial and lateral head of the gastrocnemius and tibialis anterior muscle. In addition, in any of the method of the invention, the administration of scAAV1.tMCK.NTF3 results in improved muscle strength in the subject is in the upper or lower extremities, and for example the improvement in the muscle strength is measured as a decrease in composite score on CMT Pediatric scale (CMTPeds). In addition, in any of the method of the invention, the administration of scAAV1.tMCK.NTF3 results in a decrease or halt in disease progression over a two-year time period. Disease progression is measured by the CMTPedS.

Muscle strength is also measured using electromyography, hand held myometry, fixed system myometry, manual muscle tests, and/or functional/activity tests such as the Jebsen test, and\timed tests which evaluate how long it takes a subject to perform a specific task such as the 6-minute walk test, timed rise from floor, 10 meter walk/run, timed climb 4 steps and time descent 4 steps.

In one aspect of the disclosure, in any of the methods, the subject is suffering from a hereditary neuropathy such as Charcot-Marie-Tooth (CMT) neuropathy, e.g. CMT1A, CMT2K, CMT4A, CMTRIA, and axonal and demyelinating neuropathies caused by an autosomal recessive genetic variant, or an autosomal dominant genetic variant or an X-linked genetic variant. The hereditary neuropathy may be caused by any of the genetic variants provided in Table 1. In addition, the hereditary neuropathy may be a transthyretin amyloid neuropathies caused by a mutation in the transthyretin (TTR) gene such as the following genetic variants: Val30Met, Ile107Val, and Ser77Tyr.

In another aspect of the disclosure, in any of the methods, the subject is suffering from an acquired neuropathy with axonal loss and/or impaired nerve regeneration. The acquired neuropathy is a peripheral neuropathy caused by any disorder or disease that is known to cause a neuropathy. For example, the subject is suffering from peripheral neuropathy caused by diabetes mellitus, human immunodeficiency virus (HIV) infection, thyroid disorder such as hypothyroidism, hypoglycemia, uremia, renal insufficiency, hepatic dysfunction, hepatic failure, polycythemia, connective tissue disorders, cancer, lyme disease, celiac disease, leprosy, porphyria, Sjogren's syndrome, poliomyelitis, acromegaly, disorders of lipid/glycolipid metabolism, West Nile syndrome, amyloidosis, mitochondrial disorders, dysproteinemic disorders such as monoclonal gammapathy of undetermined significance (MGUS) or POEMS syndrome. The subject is suffering from a nutritional/vitamin deficiencies such as vitamin $B_{12}$ deficiency, vitamin E deficiency or copper deficiency.

In an additional aspect of the disclosure, in any of the methods described herein, the subject is suffering from autoimmune peripheral polyneuropathy, acute inflammatory demyelinating polyradiculoneuropathy (AIDP), chronic inflammatory demyelinating polyradiculoneuropahty (CIDP), vasculitic mononeuritis multiplex, paraneuropathy, idiopathic ganglionitis, amyotrophic lateral sclerosis, multifocal motor conduction lock neuropathy, or lower motor neuron syndrome.

The acquired neuropathy may be a toxic neuropathy. For example, the toxic neuropathy is the result of the toxic effect of a prescribed medication, such Chlorampenicol, Choroquiline, Colchicine, Disulfiram, Etanercept, Ethambutal, gold, Hydroxychloroquine, Nitrofuantoin, Metronidazole, Stravudine, Zalcitabine, Infliximab, Leflunomide, Thalidomide or a chemotherapeutic agent such as Cisplatin, Cytarabine, Bortezombid, Docetaxal, Lenalidomide, Misondiazole, Oxaliplatin, Pacitaxal, Procarbazine, Suramin, Thalidomide, Vinblastine or Vincristine, or an anti-alcohol drug such as Disulfiran, or an anti-convulsant such as Phenytoin or Dilantin, or a heart or blood pressure medications such as statin, Amiodarone, Hydralazine, procainamide, Perhexiline, or an antibiotic such as Fluoroquinolones, Isoniazid, Cipro, Levaquin, Flagyl, or Metrondiazole or a skin condition treatments such as Dapsone. The toxic neuropathy may also caused by long term alcohol abuse or vitamin $B_6$ toxicity.

In another aspect of the disclosure, in any of the methods described herein, the subject is a cancer patient suffering from an acquired neuropathy. For example, the cancer patient developed a neuropathy related to nutritional deficiency, chemotherapy side effects, and/or paraneoplastic syndrome.

In yet another aspect of the disclosure, in any of the methods, the subject is a surgical patient suffering from an acquired neuropathy. For example, the surgical patient developed a neuropathy after undergoing bariatric surgery, multiple orthopedic procedures, or multiple surgeries for "entrapped nerves."

In another aspect of the disclosure, in any of the methods, the subject is suffering from hereditary myopathy, neuromuscular disease, muscular atrophy, drug-induced.myopathy, sarcopenia, cachexia, type II muscle fiber atrophy, a genetically determined muscular dystrophies, age-related muscular atrophy or an acquired autoimmune primary muscle disorder.

In another aspect of the disclosure, in any of the methods, the subject is suffering from Duchenne muscular dystrophy, Becker muscular dystrophy, myotonic muscular dystrophy, sarcoglycanopathies, myotonic dystrophy, Emery-Dreifuss muscular dystrophy, congenital muscular dystrophy, Merosin-deficient congenital muscular dystrophy, Bethlem myopathy, Ullrich congenital muscular dystrophy, fascioscapulohumeral muscular dystrophy, spinal muscular dystrophy, rigid spine muscular dystrophy, distal muscular dystrophy, oculopharyngeal muscular dystrophy, Congenital Muscular Dystrophy (MDC) 1A, 1B, 1C and 1D; Limb Girdle Muscular Dystrophy (LGMD) 1A, 1B, 1C, 1D, 1E, 1F, 1G, 1H, 2A, 2B, 2C, 2D, 2E, 2F, 2G 2H, 2I, 2J, 2K, 2L, 2M, 2N, 2O and 2Q; Muscle Eye Brain Disease; Fukuyama Walker Warburg Syndrome; Myasthenic syndromes; Congenital Myasthenias; Inclusion Body Myopathy; Inclusion Body Myositis; Dermatomyositis; Centronuclear Myopathy; Myoshi Myopathy; Mitochondrial Myopathy; Nemaline Myopathy; Nonaka Myopathy; Myasthenia Gravis; or Polymyositis.

In one embodiment, the disclosure provides for use of a therapeutically effective amount of neurotrophin-3 (NT-3), pro-NT-3, or an effective fragment thereof, or a nucleic acid encoding NT-3, pro-NT-3, or an effective fragment thereof, for the manufacture of a medicament for stimulating muscle growth in a subject. For example, the medicament is formulated for intramuscular administration.

In an exemplary embodiment, the medicament comprises a nucleic acid encoding NT-3, pro-NT-3, or an effective fragment thereof, wherein the nucleic acid in a viral vector. In related embodiments, the viral vector is an adeno-associated virus vector. In various embodiments, the nucleic acid is operatively linked to a muscle-specific promoter, such as triple muscle-specific creatine kinase promoter. In various embodiments, the nucleic acid comprises SEQ ID NO: 1.

The invention also provide for use of a nucleic acid encoding the NT-3 polypeptide for the manufacture of a medicament for treating a muscle wasting disorder or neuropathy in a human subject, wherein: a) the nucleic acid comprises a nucleotide sequence that is 90% identical to the nucleotide sequence of SEQ ID NO: 1, b) the nucleic acid comprises the nucleotide sequence of SEQ ID NO: 1; c) the nucleic acid comprises a nucleic acid sequence encoding the an amino acid sequence that is at least 90% identical to SEQ ID NO:2 or is 100% identical to SEQ ID NO: 2, d) the nucleic acid encoding the NT-3 polypeptide is any of the nucleic acids of the disclosure, e) the nucleic acid encoding the NT-3 polypeptide is the recombinant adeno-associated evirus (rAAV) scAAV1.tMCK.NTF3, and the rAAV is at a dose that results in sustained expression of a low concentration of NT-3 polypeptide, f) the nucleic acid encoding the NT-3 polypeptide is the recombinant adeno-associated virus (rAAV) scAAV1.tMCK.NTF3, the medicament is formulated for an intramuscular route of administration and the dose of the rAAV is about 1.5×1012 vg/kg to about 6.5×1012 vg/kg, g) the nucleic acid encoding the NT-3 polypeptide is the recombinant adeno-associated virus (rAAV) scAAV1.tMCK.NTF3, the medicament is formulated for an intramuscular route of administration and the dose of the rAAV is about 2×1012 vg/kg to about 6×1012 vg/kg, h) the nucleic acid encoding the NT-3 polypeptide is the recombinant adeno-associated virus (rAAV) scAAV1.tMCK.NTF3, the medicament is formulated for an intramuscular route of administration and the dose of the rAAV is about 2×1012 vg/kg, i) the nucleic acid encoding the NT-3 polypeptide is the recombinant adeno-associated virus (rAAV) scAAV1.tMCK.NTF3, the medicament is formulated for an intramuscular route of administration and the dose of the rAAV is about 4×1012 vg/kg, j) the nucleic acid encoding the NT-3 polypeptide is the recombinant adeno-associated virus (rAAV) scAAV1.tMCK.NTF3, the medicament is formulated for an intramuscular route of administration and the dose of the rAAV administered is about 6×1012 vg/kg, k) the nucleic acid encoding the NT-3 polypeptide is the recombinant adeno-associated virus (rAAV) scAAV1.tMCK.NTF3, the medicament is formulated for an intramuscular injection at a concentration of about 2×1013 vg/ml administered using 3 to 6 injections per muscle of about 0.5 to 1 ml, or 1) the nucleic acid encoding the NT-3 polypeptide is the recombinant adeno-associated virus (rAAV) scAAV1.tMCK.NTF3, the medicament is formulated for an intramuscular injection at a concentration of about $2 \times 10^{13}$ vg/ml administered using multiple injections at a total volume of about 5 to 14 ml.

The disclosure also provides for use of a dose of a nucleic acid encoding the NT-3 polypeptide for the manufacture of a medicament for improving muscle strength or stimulating muscle growth in a human subject, wherein: a) the nucleic acid comprises a nucleotide sequence that is 90% identical to the nucleotide sequence of SEQ ID NO: 1, b) the nucleic acid comprises the nucleotide sequence of SEQ ID NO: 1; c) the nucleic acid comprises a nucleic acid sequence encoding the an amino acid sequence that is at least 90% identical to SEQ ID NO: 2 or is 100% identical to SEQ ID NO: 2, d) the nucleic acid encoding the NT-3 polypeptide is any of the nucleic acids of the disclosure, e) the nucleic acid encoding the NT-3 polypeptide is the recombinant adeno-associated evirus (rAAV) scAAV1.tMCK.NTF3, and the rAAV is at a dose that results in sustained expression of a low concentration of NT-3 polypeptide, f) the nucleic acid encoding the NT-3 polypeptide is the recombinant adeno-associated virus (rAAV) scAAV1.tMCK.NTF3, the composition is formulated for an intramuscular route of administration and the dose of the rAAV is about 1.5×1012 vg/kg to about 6.5×1012 vg/kg, g) the nucleic acid encoding the NT-3 polypeptide is the recombinant adeno-associated virus (rAAV) scAAV1.tMCK.NTF3, the medicament is formulated for an intramuscular route of administration and the dose of the rAAV is about 2×1012 vg/kg to about 6×1012 vg/kg, h) the nucleic acid encoding the NT-3 polypeptide is the recombinant adeno-associated virus (rAAV) scAAV1.tMCK.NTF3, the medicament is formulated for an intramuscular route of administration and the dose of the rAAV is about 2×1012 vg/kg, i) the nucleic acid encoding the NT-3 polypeptide is the recombinant adeno-associated virus (rAAV) scAAV1.tMCK.NTF3, the medicament is formulated for an intramuscular route of administration and the dose of the rAAV is about 4×1012 vg/kg, j) the nucleic acid encoding the NT-3 polypeptide is the recombinant adeno-associated virus (rAAV) scAAV1.tMCK.NTF3, the medicament is formulated for an intramuscular route of administration and the dose of the rAAV administered is about 6×1012 vg/kg, k) the nucleic acid encoding the NT-3 polypeptide is the recombinant adeno-associated virus (rAAV) scAAV1.tMCK.NTF3, the medicament is formulated for an intramuscular injection at a concentration of about 2×1013 vg/ml administered using 3 to 6 injections per muscle of about 0.5 to 1 ml, or 1) the nucleic acid encoding the NT-3 polypeptide is the recombinant adeno-associated virus (rAAV) scAAV1.tMCK.NTF3, the medicament is formulated for an intramuscular injection at a concentration of about $2 \times 10^{13}$ vg/ml administered using multiple injections at a total volume of about 5 to 14 ml.

For example, any of the medicmants of the disclosure can comprise a nucleic acid is formulated for administration using a viral vector, such as an adeno-associated virus vector. In addition, any of the medicaments of the disclosure can comprise a nucleic acid is operatively linked to a muscle-specific promoter, such as the muscle-specific promoter is muscle-specific creatine kinase promoter (MCK). In another embodiment, in any of the medicaments or the disclosure scAAV1.tMCK.NTF3 comprises the NT-3 gene cassette set out in SEQ ID NO: 11. In one embodiment, the disclosure provide for use of a recombinant adeno-associated virus (rAAV) scAAV1.tMCK.NTF3 for the preparation of a medicament for treating a muscle wasting disorder or neuropathy in a human subject in need thereof, wherein the medicament results in sustained expression of a low concentration of NT-3 protein.

In another embodiment, the disclosure provides for use of a recombinant adeno-associated virus (rAAV) scAAV1.tMCK.NTF3 for the preparation of a medicament for stimulating muscle growth in a human subject in need thereof, wherein the dose results in sustained expression of a low concentration of NT-3 protein.

In one embodiment, the disclosure provides for use of a recombinant adeno-associated virus (rAAV) scAAV1.tMCK.NTF3 for the preparation of a medicament for treating a muscle wasting disorder or neuropathy in a human subject in need thereof, wherein the medicament is formulated for an intramuscular route of administration, and wherein the medicament comprises a dose of the rAAV that is about $1.0 \times 10^{12}$ vg/kg to about $7 \times 10^{12}$ vg/kg, or about $1.5 \times 10^{12}$ vg/kg to about $6.5 \times 10^{12}$ vg/kg, or about $2 \times 10^{12}$ vg/kg to about $6 \times 10^{12}$ vg/kg.

In another embodiment, the disclosure provides for use of a recombinant adeno-associated virus (rAAV) scAAV1.tMCK.NTF3 for the preparation of a medicament for treating a muscle wasting disorder or neuropathy in a human subject in need thereof, wherein the medicament is formulated for an intramuscular route of administration, and wherein the medicament comprises a dose of the rAAV that is about is about $1.0 \times 10^{12}$ vg/kg, or about $1.5 \times 10^{12}$ vg/kg, or about $2 \times 10^{12}$ vg/kg, or about $3 \times 10^{12}$ vg/kg, or about $4 \times 10^{12}$ vg/kg, or about $5 \times 10^{12}$ vg/kg, or about $6 \times 10^{12}$ vg/kg, or about 7×10$^{12}$ vg/kg, or about 8×10$^{12}$ vg/kg, or about 9×10$^{12}$ vg/kg, or about 1×10$^{13}$ vg/kg.

In another embodiment, the disclosure provides for use of a recombinant adeno-associated virus (rAAV) scAAV1.tMCK.NTF3 for the preparation of a medicament for treating a muscle wasting disorder or neuropathy in a human subject in need thereof, wherein the medicament is formulated for an intramuscular route of administration, and wherein the medicament comprises a concentration of the rAAV that is about 2×10$^{13}$ vg/ml. For example, the medicament is administered using 3 to 6 injections per muscle respectively e.g. each injection volume will be 0.5 to 1 ml to the medial and lateral heads of the gastroc and tibialis anterior muscle in each leg, wherein a total of 5 mL to 14 mL of vector will be administered to the medial and lateral heads of the gastroc and tibialis anterior muscle in each leg.

In an exemplary embodiment, the disclosure provides for use of a recombinant adeno-associated virus (rAAV) scAAV1.tMCK.NTF3 for the preparation of a medicament for treating a muscle wasting disorder or neuropathy in a human subject in need thereof, wherein the medicament is formulated for an intramuscular route of administration, and wherein the medicament comprises a dose of the rAAV that is about 1×10$^{13}$ vg/ml administered using 3 to 6 injections per muscle respectively (each injection volume will be 0.5 to 1 ml). A total of 5 mL to 14 mL of vector is administered to the medial and lateral heads of the gastroc and tibialis anterior muscle in each leg.

In one embodiment, the disclosure provides for use of a recombinant adeno-associated virus (rAAV) scAAV1.tMCK.NTF3 for the preparation of a medicament for improving muscle strength or stimulating muscle growth in a human subject in need thereof, wherein the medicament is formulated for an intramuscular route of administration, and wherein the medicament comprises a dose of the rAAV that is about 1.0×10$^{12}$ vg/kg to about 7×10$^{12}$ vg/kg, or about 1.5×10$^{12}$ vg/kg to about 6.5×10$^{12}$ vg/kg, or about 2×10$^{12}$ vg/kg to about 6×10$^{12}$ vg/kg.

In another embodiment, the disclosure provides for use of a recombinant adeno-associated virus (rAAV) scAAV1.tMCK.NTF3 for the preparation of a medicament for improving muscle strength or stimulating muscle growth in a human subject in need thereof, wherein the medicament is formulated for an intramuscular route of administration, and wherein the medicament comprises a dose of the rAAV that is about 1.0×10$^{12}$ vg/kg, or about 1.5×10$^{12}$ vg/kg, or about 2×10$^{12}$ vg/kg, or about 3×10$^{12}$ vg/kg, or about 4×10$^{12}$ vg/kg, or about 5×10$^{12}$ vg/kg, or about 6×10$^{12}$ vg/kg, or about 7×10$^{12}$ vg/kg, or about 8×10$^{12}$ vg/kg, or about 9×10$^{12}$ vg/kg, or about 1×10$^{13}$ vg/kg.

In another embodiment, the disclosure provides for use of a recombinant adeno-associated virus (rAAV) scAAV1.tMCK.NTF3 for the preparation of a medicament for improving muscle strength or stimulating muscle growth in a human subject in need thereof, wherein the medicament is formulated for an intramuscular route of administration, and wherein the medicament comprises a concentration of the rAAV that is about 2×10$^{13}$ vg/ml administered at low dose (2×10$^{12}$ vg/kg per patient) and at high dose (6×10$^{12}$ vg/kg per patient). In some embodiments, the medicament is administered using 3 to 6 injections per muscle respectively, e.g. each injection volume is 0.5 to 1 ml to the medial and lateral heads of the gastroc and tibialis anterior muscle in each leg. A total of 5 mL to 14 mL of vector will be administered to the medial and lateral heads of the gastroc and tibialis anterior muscle in each leg.

In an exemplary embodiment, the disclosure provides for use of a recombinant adeno-associated virus (rAAV) scAAV1.tMCK.NTF3 for the preparation of a medicament for improving muscle strength or stimulating muscle growth in a human subject in need thereof, wherein the medicament is formulated for an intramuscular route of administration, and wherein the medicament comprises a concentration of the rAAV that is about 2×10$^{13}$ vg/ml administered at low dose (2×10$^{12}$ vg/kg per patient) and at high dose (6×10$^{12}$ vg/kg per patient) using 3 to 6 injections per muscle respectively (each injection volume will be 0.5 to 1 ml). A total of 5 mL to 14 mL of vector will be administered to the medial and lateral heads of the gastroc and tibialis anterior muscle in each leg.

In any of the uses of the disclosure, the medicament is formulated for intramuscular bilateral injection to the medial and lateral head of the gastrocnemius and tibialis anterior muscle. In addition, in any of the uses of the invention, the medicament results in improved muscle strength in the subject is in the upper or lower extremities, and for example the improvement in the muscle strength is measured as a decrease in composite score on CMT Pediatric scale (CMT-PedS). In addition, in any of the uses of the invention, the medicament results in a decrease or halt in disease progression over a two-year time period. Disease progression is measured by the CMTPedS.

In an aspect of the disclosure, in any of the uses of the disclosure, the subject is suffering from a hereditary neuropathy such as Charcot-Marie-Tooth (CMT) neuropathy, e.g. CMT1A, CMT2K, CMT4A, CMTRIA, and axonal and demyelinating neuropathies caused by an autosomal recessive genetic variant, or an autosomal dominant genetic variant or an X-linked genetic variant. The hereditary neuropathy may be caused by any of the genetic variants provided in Table 1. In addition, the hereditary neuropathy may be a transthyretin amyloid neuropathies caused by a mutation in the transthyretin (TTR) gene such as the following genetic variants: Val30Met, Ile107Val, and Ser77Tyr.

In another aspect of the disclosure, in any of the methods of the invention, the subject is suffering from an acquired neuropathy with axonal loss and/or impaired nerve regeneration. The acquired neuropathy is a peripheral neuropathy caused by any disorder or disease that causes neuropathy. For example, the subject is suffering from peripheral neuropathy caused by diabetes mellitus, human immunodeficiency virus (HIV) infection, thyroid disorder such as hypothyroidism, hypoglycemia, uremia, renal insufficiency, hepatic dysfunction, hepatic failure, polycythemia, connective tissue disorders, cancer, lyme disease, celiac disease, leprosy, porphyria, Sjogren's syndrome, poliomyelitis, acromegaly, disorders of lipid/glycolipid metabolism, West Nile syndrome, amyloidosis, mitochondrial disorders, dysproteinemic disorders such as monoclonal gammapathy of undetermined significance (MGUS) or POEMS syndrome. The subject may be suffering from a nutritional/vitamin deficiencies such as vitamin B$_{12}$ deficiency, vitamin E deficiency or copper deficiency.

In addition, in any of the uses of the disclosure, the subject is suffering from autoimmune peripheral polyneuropathy, acute inflammatory demyelinating polyradiculoneuropathy (AIDP), chronic inflammatory demyelinating polyradiculoneuropathy (CIDP), vasculitic mononeuritis multiplex, paraneuropathy, idiopathic ganglionitis, amyotrophic lateral sclerosis, multifocal motor conduction lock neuropathy, or lower motor neuron syndrome.

The acquired neuropathy is a toxic neuropathy. For example, the toxic neuropathy is the result of the toxic effect of a prescribed medication, such Chlorampenicol, Choroquiline, Colchicine, Disulfiram, Etanercept, Ethambutal, gold, Hydroxychloroquine, Nitrofuantoin, Metronidazole, Stravudine, Zalcitabine, Infliximab, Leflunomide, Thalidomide or a chemotherapeutic agent such as Cisplatin, Cytarabine, Bortezombid, Docetaxal, Lenalidomide, Misondiazole, Oxaliplatin, Pacitaxal, Procarbazine, Suramin, Thalidomide, Vinblastine or Vincristine, or an anti-alcohol drug such as Disulfiran, or an anti-convulsant such as Phenytoin or Dilantin, or a heart or blood pressure medications such as a statin, Amiodarone, Hydralazine, procainamide, Perhexiline, or an antibiotic such as Fluoroquinolones, Isoniazid, Cipro, Levaquin, Flagyl, or Metrondiazole, or a skin condition treatments such as Dapsone. The toxic neuropathy may be caused by long term alcohol abuse or vitamin $B_6$ toxicity.

In another aspect, in any of the uses of the disclosure, the subject is a cancer patient suffering from an acquired neuropathy. For example, the cancer patient developed a neuropathy related to nutritional deficiency, chemotherapy side effects, and/or paraneoplastic syndrome.

In yet another aspect, in any of the uses of the disclosure, the subject is a surgical patient suffering from an acquired neuropathy. For example, the surgical patient developed a neuropathy after undergoing bariatric surgery, multiple orthopedic procedures, or multiple surgeries for "entrapped nerves."

In another aspect, in any of the uses of the disclosure, the subject is suffering from hereditary myopathy, neuromuscular disease, muscular atrophy, drug-induced. myopathy, sarcopenia, cachexia, type II muscle fiber atrophy, a genetically determined muscular dystrophies, age-related muscular atrophy or an acquired autoimmune primary muscle disorder.

In another aspect, in any of the uses of the disclosure, the subject is suffering from Duchenne muscular dystrophy, Becker muscular dystrophy, myotonic muscular dystrophy, sarcoglycanopathies, myotonic dystrophy, Emery-Dreifuss muscular dystrophy, congenital muscular dystrophy, Merosin-deficient congenital muscular dystrophy, Bethlem myopathy, Ullrich congenital muscular dystrophy, fascioscapulohumeral muscular dystrophy, spinal muscular dystrophy, rigid spine muscular dystrophy, distal muscular dystrophy, oculopharyngeal muscular dystrophy, Congenital Muscular Dystrophy (MDC) 1A, 1B, 1C and 1D; Limb Girdle Muscular Dystrophy (LGMD) 1A, 1B, 1C, 1D, 1E, 1F, 1G, 1H, 2A, 2B, 2C, 2D, 2E, 2F, 2G 2H, 2I, 2J, 2K, 2L, 2M, 2N, 2O and 2Q; Muscle Eye Brain Disease; Fukuyama Walker Warburg Syndrome; Myasthenic syndromes; Congenital Myasthenias; Inclusion Body Myopathy; Inclusion Body Myositis; Dermatomyositis; Centronuclear Myopathy; Myoshi Myopathy; Mitochondrial Myopathy; Nemaline Myopathy; Nonaka Myopathy; Myasthenia Gravis; or Polymyositis.

In one embodiment, the disclosure provides for a composition comprising a therapeutically effective amount of neurotrophin-3 (NT-3), pro-NT-3, or an effective fragment thereof, or a nucleic acid encoding NT-3, pro-NT-3, or an effective fragment thereof, for use in stimulating muscle growth in a subject. For example, the compositions of the disclosure are formulated for intramuscular administration.

In an exemplary embodiment, the composition comprises a nucleic acid encoding NT-3, pro-NT-3, or an effective fragment thereof. In related embodiments, the nucleic acid in a viral vector, such as an an adeno-associated virus vector. In various embodiments, the nucleic acid is operatively linked to a muscle-specific promoter, such as triple muscle-specific creatine kinase promoter. In various embodiments, the composition comprises a nucleic acid comprising the nucleotide sequence of SEQ ID NO: 1.

The disclosure also provides compositions comprising a nucleic acid encoding a NT-3 polypeptide for use in treating a muscle wasting disorder or neuropathy in a human subject, wherein: a) the nucleic acid comprises a nucleotide sequence that is 90% identical to the nucleotide sequence of SEQ ID NO: 1, b) the nucleic acid comprises the nucleotide sequence of SEQ ID NO: 1; c) the nucleic acid comprises a nucleic acid sequence encoding an amino acid sequence that is at least 90% identical to SEQ ID NO: 2 or is 100% identical to SEQ ID NO: 2, d) the nucleic acid encoding the NT-3 polypeptide is any of the nucleic acids of the disclosure, e) the nucleic acid encoding the NT-3 polypeptide is the recombinant adeno-associated evirus (rAAV) scAAV1.tMCK.NTF3, and the rAAV is administered at a dose that results in sustained expression of a low concentration of NT-3 polypeptide, f) the nucleic acid encoding the NT-3 polypeptide is the recombinant adeno-associated virus (rAAV) scAAV1.tMCK.NTF3, the composition is formulated for an intramuscular route of administration and the dose of the rAAV is about $1.5 \times 10^{12}$ vg/kg to about $6.5 \times 10^{12}$ vg/kg, g) the nucleic acid encoding the NT-3 polypeptide is the recombinant adeno-associated virus (rAAV) scAAV1.tMCK.NTF3, the composition is formulated for an intramuscular route of administration and the dose of the rAAV is about $2 \times 10^{12}$ vg/kg to about $6 \times 10^{12}$ vg/kg, h) the nucleic acid encoding the NT-3 polypeptide is the recombinant adeno-associated virus (rAAV) scAAV1.tMCK.NTF3, the composition is formulated for an intramuscular route of administration and the dose of the rAAV is about $2 \times 10^{12}$ vg/kg, i) the nucleic acid encoding the NT-3 polypeptide is the recombinant adeno-associated virus (rAAV) scAAV1.tMCK.NTF3, the composition is formulated for an intramuscular route of administration and the dose of the rAAV is about $4 \times 10^{12}$ vg/kg, j) the nucleic acid encoding the NT-3 polypeptide is the recombinant adeno-associated virus (rAAV) scAAV1.tMCK.NTF3, the composition is formulated for an intramuscular route of administration and the dose of the rAAV administered is about $6 \times 10^{12}$ vg/kg, k) the nucleic acid encoding the NT-3 polypeptide is the recombinant adeno-associated virus (rAAV) scAAV1.tMCK.NTF3, the composition is formulated for an intramuscular injection at a concentration of about $2 \times 10^{13}$ vg/ml administered using 3 to 6 injections per muscle of about 0.5 to 1 ml, or l) the nucleic acid encoding the NT-3 polypeptide is the recombinant adeno-associated virus (rAAV) scAAV1.tMCK.NTF3, the composition is formulated for an intramuscular injection at a concentration of about $2 \times 10^{13}$ vg/ml administered using multiple injections at a total volume of about 5 to 14 ml.

In another embodiment, the disclosure provides for composition comprising a nucleic acid encoding the NT-3 polypeptide for use in improving muscle strength or stimulating muscle growth in a human subject, wherein a) the nucleic acid comprises a nucleotide sequence that is 90% identical to the nucleotide sequence of SEQ ID NO: 1, b) the nucleic acid comprises the nucleotide sequence of SEQ ID NO: 1; c) the nucleic acid comprises a nucleic acid sequence encoding the an amino acid sequence that is at least 90% identical to SEQ ID NO:2 or is 100% identical to SEQ ID NO: 2, d) the nucleic acid encoding the NT-3 polypeptide is any of the nucleic acids of the disclosure, e) the nucleic acid encoding the NT-3 polypeptide is the recombinant adeno-associated evirus (rAAV) scAAV1.tMCK.NTF3, and the rAAV is at a dose that results in sustained expression of a low concentration of NT-3 polypeptide, f) the nucleic acid encoding the NT-3 polypeptide is the recombinant adeno-associated virus (rAAV) scAAV1.tMCK.NTF3, the composition is formulated for an intramuscular route of administration and the dose of the rAAV is about 1.5×1012 vg/kg to about 6.5×1012 vg/kg, g) the nucleic acid encoding the NT-3 polypeptide is the recombinant adeno-associated virus (rAAV) scAAV1.tMCK.NTF3, the composition is formulated for an intramuscular route of administration and the dose of the rAAV is about 2×1012 vg/kg to about 6×1012 vg/kg, h) the nucleic acid encoding the NT-3 polypeptide is the recombinant adeno-associated virus (rAAV) scAAV1.tMCK.NTF3, the composition is formulated for an intramuscular route of administration and the dose of the rAAV is about 2×1012 vg/kg, i) the nucleic acid encoding the NT-3 polypeptide is the recombinant adeno-associated virus (rAAV) scAAV1.tMCK.NTF3, the composition is formulated for an intramuscular route of administration and the dose of the rAAV is about 4×1012 vg/kg, j) the nucleic acid encoding the NT-3 polypeptide is the recombinant adeno-associated virus (rAAV) scAAV1.tMCK.NTF3, the composition is formulated for an intramuscular route of administration and the dose of the rAAV is about 6×1012 vg/kg, k) the nucleic acid encoding the NT-3 polypeptide is the recombinant adeno-associated virus (rAAV) scAAV1.tMCK.NTF3, the composition is formulated for an intramuscular injection at a concentration of about 2×1013 vg/ml administered using 3 to 6 injections per muscle of about 0.5 to 1 ml, or l) the nucleic acid encoding the NT-3 polypeptide is the recombinant adeno-associated virus (rAAV) scAAV1.tMCK.NTF3, the composition is formulated for an intramuscular injection at a concentration of about 2×10$^{13}$ vg/ml administered using multiple injections at a total volume of about 5 to 14 ml.

For example, any of the composition of the disclosure can comprise a nucleic acid is formulated for administration using a viral vector, such as an adeno-associated virus vector. In addition, any of the compositions of the disclosure can comprise a nucleic acid is operatively linked to a muscle-specific promoter, such as the muscle-specific promoter is muscle-specific creatine kinase promoter (MCK). In another embodiment, in any of the compositions or the disclosure scAAV1.tMCK.NTF3 comprises the NT-3 gene cassette set out in SEQ ID NO: 11.

In one embodiment, the disclosure provides for compositions comprising a dose of recombinant adeno-associated virus (rAAV) scAAV1.tMCK.NTF3 for treating a muscle wasting disorder or neuropathy in a human subject in need thereof, that results in in sustained expression of a low concentration of NT-3 protein.

In another embodiment, the disclosure provide for use of a recombinant adneo-associated virus (rAAV) scAAV1.tMCK.NTF3 for the stimulating muscle growth in a human subject in need thereof that results in sustained expression of a low concentration of NT-3 protein.

In one embodiment, the disclosure provides for compositions comprising a dose of recombinant adeno-associated virus (rAAV) scAAV1.tMCK.NTF3 for treating a muscle wasting disorder or neuropathy in a human subject in need thereof, wherein the composition is formulated for intramuscular administration and the dose of the rAAV administered is about 1.0×10$^{12}$ vg/kg to about 7×10$^{12}$ vg/kg, or about 1.5×10$^{12}$ vg/kg to about 6.5×10$^{12}$ vg/kg, or about 2×10$^{12}$ vg/kg to about 6×10$^{12}$ vg/kg.

In another embodiment, the disclosure provides for compositions comprising a dose of recombinant adeno-associated virus (rAAV) scAAV1.tMCK.NTF3 for treating a muscle wasting disorder or neuropathy in a human subject in need thereof, wherein the composition is formulated for intramuscular administration and the dose of the rAAV administered is about 1.0×10$^{12}$ vg/kg, or about 1.5×10$^{12}$ vg/kg, or about 2×10$^{12}$ vg/kg, or about 3×10$^{12}$ vg/kg, or about 4×10$^{12}$ vg/kg, or about 5×10$^{12}$ vg/kg, or about 6×10$^{12}$ vg/kg, or about 7×10$^{12}$ vg/kg, or about 8×10$^{12}$ vg/kg, or about 9×10$^{12}$ vg/kg, or about 1×10$^{13}$ vg/kg.

In another embodiment, the disclosure provides for compositions comprising a dose of recombinant adeno-associated virus (rAAV) scAAV1.tMCK.NTF3 for treating a muscle wasting disorder or neuropathy in a human subject in need thereof, wherein the composition is formulated for intramuscular administration and the dose of the rAAV administered is about 2×10$^{13}$ vg/ml administered at low dose (2×10$^{12}$ vg/kg per patient) and at high dose (6×10$^{12}$ vg/kg per patient). In some embodiments, the composition is administered using 3 to 6 injections per muscle respectively (each injection volume will be 0.5 to 1 ml) to the medial and lateral heads of the gastroc and tibialis anterior muscle in each leg. A total of 5 mL to 14 mL of vector will be administered to the medial and lateral heads of the gastroc and tibialis anterior muscle in each leg.

In an exemplary embodiment, the disclosure provides for compositions comprising a dose of recombinant adeno-associated virus (rAAV) scAAV1.tMCK.NTF3 for treating a muscle wasting disorder or neuropathy in a human subject in need thereof, wherein the composition is formulated for intramuscular administration and the dose of the rAAV administered is about 2×10$^{13}$ vg/ml administered at low dose (2×10$^{12}$ vg/kg per patient) and at high dose (6×10$^{12}$ vg/kg per patient using 3 to 6 injections per muscle respectively each injection volume will be 0.5 to 1 ml). A total of 5 mL to 14 mL of vector will be administered to the medial and lateral heads of the gastroc and tibialis anterior muscle in each leg.

In one embodiment, the disclosure provides for compositions comprising a dose of recombinant adeno-associated virus (rAAV) scAAV1.tMCK.NTF3 for improving muscle strength in a human subject, wherein the composition is formulated for intramuscular administration and the dose of the rAAV administered is about 1.0×10$^{12}$ vg/kg to about 7×10$^{12}$ vg/kg, or about 1.5×10$^{12}$ vg/kg to about 6.5×10$^{12}$ vg/kg, or about 2×10$^{12}$ vg/kg to about 6×10$^{12}$ vg/kg.

In another embodiment, the disclosure provides for compositions comprising a dose of recombinant adeno-associated virus (rAAV) scAAV1.tMCK.NTF3 for improving muscle strength in a human subject, wherein the composition is formulated for intramuscular administration and the dose of the rAAV administered is about 1.0×10$^{12}$ vg/kg, or about 1.5×10$^{12}$ vg/kg, or about 2×10$^{12}$ vg/kg, or about 3×10$^{12}$ vg/kg, or about 4×10$^{12}$ vg/kg, or about 5×10$^{12}$ vg/kg, or about 6×10$^{12}$ vg/kg, or about 7×10$^{12}$ vg/kg, or about 8×10$^{12}$ vg/kg, or about 9×10$^{12}$ vg/kg, or about 1×10$^{13}$ vg/kg.

In another embodiment, the disclosure provides for compositions comprising a dose of recombinant adeno-associated virus (rAAV) scAAV1.tMCK.NTF3 for improving muscle strength or stimulating muscles growth in a human subject in need thereof, wherein the composition is formulated for intramuscular administration and the dose of the rAAV administered is about 2×10$^{13}$ vg/ml administered at low dose (2×10$^{12}$ vg/kg per patient) and at high dose (6×10$^{12}$ vg/kg per patient). In some embodiments, the composition is administered using 3 to 6 injections per muscle respectively (each injection volume will be 0.5 to 1 ml) to the medial and lateral heads of the gastroc and tibialis anterior muscle in each leg. A total of 5 mL to 14 mL of vector will be administered to the medial and lateral heads of the gastroc and tibialis anterior muscle in each leg.

In an exemplary embodiment, the disclosure provides for compositions comprising a dose of recombinant adeno-associated virus (rAAV) scAAV1.tMCK.NTF3 for improving muscle strength or stimulating muscle growth in a human subject in need thereof, wherein the composition is formulated for intramuscular administration and the dose of the rAAV administered is about $2\times10^{13}$ vg/ml administered at low dose ($2\times10^{12}$ vg/kg per patient) and at high dose ($6\times10^{12}$ vg/kg per patient using 3 to 6 injections per muscle respectively each injection volume will be 0.5 to 1 ml). A total of 5 mL to 14 mL of vector will be administered to the medial and lateral heads of the gastroc and tibialis anterior muscle in each leg.

In any of the compositions of the disclosure, the route of administration of scAAV1.tMCK.NTF3 is an intramuscular bilateral injection to the medial and lateral head of the gastrocnemius and tibialis anterior muscle. In addition, in any of the compositions of the invention, the administration of scAAV1.tMCK.NTF3 results in improved muscle strength in the subject is in the upper or lower extremities, and for example the improvement in the muscle strength is measured as a decrease in composite score on CMT Pediatric scale (CMTPedS). In addition, any of the compositions of the disclosure, the administration of the composition results in a decrease or halt in disease progression over a two-year time period. Disease progression is measured by the CMTPedS. The CMTPedS is an 11-item scale comprised of the Functional Dexterity Test, Nine-Hole Peg Test (SHPT), hand grip, foot plantar flexion, and foot dorsiflexion strength using handheld myometry, pinprick and vibration sensation, the Bruininks Oseretsky Test-Balance assessment, gait assessment, long jump, and six-minute walk test (6MWT). The efficacy defined as halting of the decline in abilities measured by this scale at 2 years post gene transfer.

In aspect of the disclosure, in any of the compositions, the subject is suffering from hereditary neuropathies such as Charcot-Marie-Tooth (CMT) neuropathy, e.g. CMT1A, CMT2K, CMT4A, CMTRIA and axonal and demyelinating europathies caused by an autosomal recessive genetic variant, or an autosomal dominant genetic variant or an X-linked genetic variant. The hereditary neuropathy may be caused by any of the genetic variants provided in Table 1. In addition, the hereditary neuropathy may be a transthyretin amyloid neuropathies caused by a mutation in the transthyretin (TTR) gene such as the following genetic variants: Val30Met, Ile107Val, and Ser77Tyr.

In another aspect of the disclosure, in any of the compositions, the subject is suffering from an acquired neuropathy with axonal loss and/or impaired nerve regeneration. The acquired neuropathy is a peripheral neuropathy caused by any disorder or disease that causes neuropathy. For example, the subject is suffering from peripheral neuropathy caused by diabetes mellitus, human immunodeficiency virus (HIV) infection, thyroid disorder such as hypothyroidism, hypoglycemia, uremia, renal insufficiency, hepatic dysfunction, hepatic failure, polycythemia, connective tissue disorders, cancer, lyme disease, celiac disease, leprosy, porphyria, Sjogren's syndrome, poliomyelitis, acromegaly, disorders of lipid/glycolipid metabolism, West Nile syndrome, amyloidosis, mitochondrial disorders, dysproteinemic disorders such as monoclonal gammapathy of undetermined significance (MGUS) or POEMS syndrome. The subject is suffering from a nutritional/vitamin deficiencies such as vitamin $B_{12}$ deficiency, vitamin E deficiency or copper deficiency.

In addition, in any of the compositions of the disclosure, the subject is suffering from autoimmune peripheral polyneuropathy, acute inflammatory demyelinating polyradiculoneuropathy (AIDP), chronic inflammatory demyelinating polyradiculoneuropahty (CIDP), vasculitic mononeuritis multiplex, paraneuropathy, idiopathic ganglionitis, amyotrophic lateral sclerosis, multifocal motor conduction lock neuropathy, or lower motor neuron syndrome.

In any of the compositions of the disclosure, the acquired neuropathy is a toxic neuropathy. For example, the toxic neuropathy is the result of the toxic effect of a prescribed medication, such Chlorampenicol, Choroquiline, Colchicine, Disulfiram, Etanercept, Ethambutal, Gold, Hydroxychloroquine, Nitrofuantoin, Metronidazole, Stravudine, Zalcitabine, Infliximab, Leflunomide, Thalidomide or a chemotherapeutic agent such as Cisplatin, Cytarabine, Bortezombid, Docetaxal, Lenalidomide, Misondiazole, Oxaliplatin, Pacitaxal, Procarbazine, Suramin, Thalidomide, Vinblastine or Vincristine, or anti-alcohol drugs such as Disulfiran, or anti-convulsants such as Phenytoin or Dilantin, or heart or blood pressure medications such as statins, Amiodarone, Hydralazine, procainamide, Perhexiline, or an antibiotic such as Fluoroquinolones, Isoniazid, Cipro, Levaquin, Flagyl, or Metrondiazole and skin condition treatments such as Dapsone. The toxic neuropathy is also caused by long term alcohol abuse or vitamin $B_6$ toxicity.

In another aspect of the disclosure, in any of the compositions, the subject is a cancer patient suffering from an acquired neuropathy. For example, the cancer patient developed a neuropathy related to nutritional deficiency, chemotherapy side effects, and/or paraneoplastic syndrome.

In yet another aspect of the disclosure, in any of the compositions, the subject is a surgical patient suffering from an acquired neuropathy. For example, the surgical patient developed a neuropathy after undergoing bariatric surgery, multiple orthopedic procedures, or multiple surgeries for "entrapped nerves."

In another aspect of the disclosure, in any of the, the subject is suffering from hereditary myopathy, neuromuscular disease, muscular atrophy, drug-induced. myopathy, sarcopenia, cachexia, type II muscle fiber atrophy, a genetically determined muscular dystrophies, age-related muscular atrophy or an acquired autoimmune primary muscle disorder.

In another aspect of the disclosure, in any of the compositions, the subject is suffering from Duchenne muscular dystrophy, Becker muscular dystrophy, myotonic muscular dystrophy, sarcoglycanopathies, myotonic dystrophy, Emery-Dreifuss muscular dystrophy, congenital muscular dystrophy, Merosin-deficient congenital muscular dystrophy, Bethlem myopathy, Ullrich congenital muscular dystrophy, fascioscapulohumeral muscular dystrophy, spinal muscular dystrophy, rigid spine muscular dystrophy, distal muscular dystrophy, oculopharyngeal muscular dystrophy, Congenital Muscular Dystrophy (MDC) 1A, 1B, 1C and 1D; Limb Girdle Muscular Dystrophy (LGMD) 1A, 1B, 1C, 1D, 1E, 1F, 1G, 1H, 2A, 2B, 2C, 2D, 2E, 2F, 2G 2H, 2I, 2J, 2K, 2L, 2M, 2N, 2O and 2Q; Muscle Eye Brain Disease; Fukuyama Walker Warburg Syndrome; Myasthenic syndromes; Congenital Myasthenias; Inclusion Body Myopathy; Inclusion Body Myositis; Dermatomyositis; Centronuclear Myopathy; Myoshi Myopathy; Mitochondrial Myopathy; Nemaline Myopathy; Nonaka Myopathy; Myasthenia Gravis; or Polymyositis.

In another aspect of the disclosure, in any of the compositions, the subject is suffering from traumatic nerve injuries such as nerve injuries caused by compression, double crush or transection.

BRIEF DESCRIPTION OF THE DRAWINGS

The present invention may be more readily understood by reference to the following figures, wherein:

(FIG. 2C) Relative expression of glycolytic (1-1K1 and PK1) and oxidative regulators (PGC1α) by qPCR; GAPDH was used a housekeeping gene. Error bars are ±SEM; n=5-6 in each group, *P<0.05, one-way Anova followed by Tukey's multiple comparison test.

(FIG. 3A) Representative western blot images and analysis of Akt/mTOR pathway, Phospho (P)-Akt (Ser473), P-4EBP1 (Thr37/46), and P-S6 (Ser235/236) in myotubes incubated with recombinant human NT-3 (100 ng/ml) or PBS (control) for 30 minutes. Density values of phosphorylated protein bands were normalized to GAPDH and showed as percent of control group. Coomassie Blue stained membrane represents equal gel loading. Myotubes were incubated with NT-3 (100 ng/ml) for 48 hours then, relative mRNA expression of metabolic markers (PGC1a, HK1, PK1) was detected by qPCR (FIG. 3B), and glucose consumption versus lactate production in cell culture media was detected by ELISA (FIG. 3C). (FIG. 3D) Relative expression levels of myogenin and NT-3 receptors, P75NTR and TrkC in myoblasts versus myotubes after NT-3 (100 ng/ml) treatment for 48 hours. GAPDH was as housekeeping gene in the analyses. The results shown are mean±SEM from at least three independent experiment, *P<0.05, Student's paired t-test.

FIG. 8A-8B indicate the location of IM injection of AAV.tMCK.NTF3 in human subjects.

FIG. 9 provides the nucleotide sequence of AAV.tMC-K.NTF3 (SEQ ID NO: 11).

DETAILED DESCRIPTION

Figure 1:
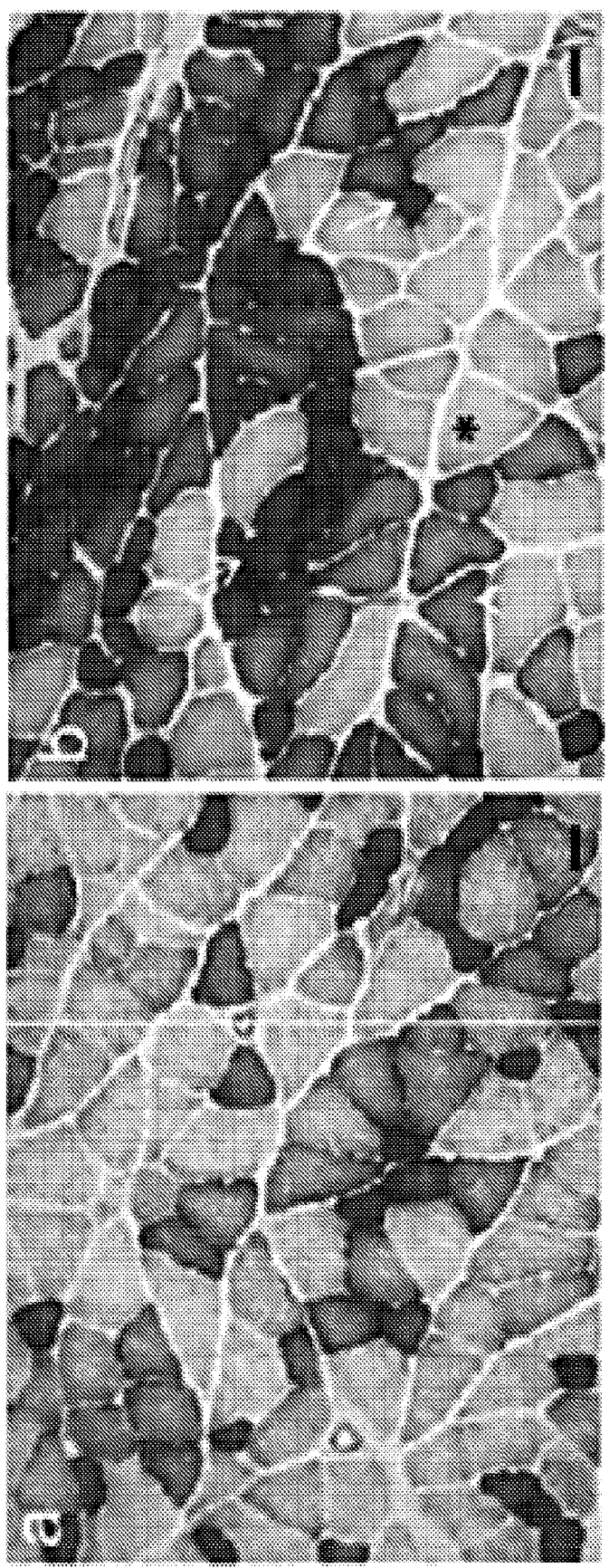
FIGS. 1A-C provide graphs and images showing AAV1.NT-3-induced fiber type remodeling in TrJ muscle. Representative images of SDH-stained tissue sections of AAV1.tMCK.NT-3 treated Trembler J (TrJ) (FIG. 1A) and untreated (TrJ-PBS) gastrocnemius muscle (FIG. 1B) at 16 weeks post-injection. Slow twitch oxidative (STO, arrows), fast twitch oxidative (FTO, arrow head) and fast twitch glycolytic (FTG, asterisks) are shown (FIG. 1B). Oxidative fibers are decreased in a. In the TrJ-PBS muscle (FIG. 1B), increased numbers of small STO fibers and angular fibers of all fiber types are present along with small type groupings compatible with neurogenic changes. Scale bar=30 gm for a, b. Fiber type switching from STO to FTO/FTG fibers in the TrJ muscle with NT-3 gene therapy (FIG. 1C). Mean percent of STO (derived from n=3-5 mice in each group) in both treatment groups was not significantly different from the wild type (WT) muscle indicating a change towards normalization of fiber type distribution with NT-3 in the TrJ neurogenic muscle.
Figure 1:
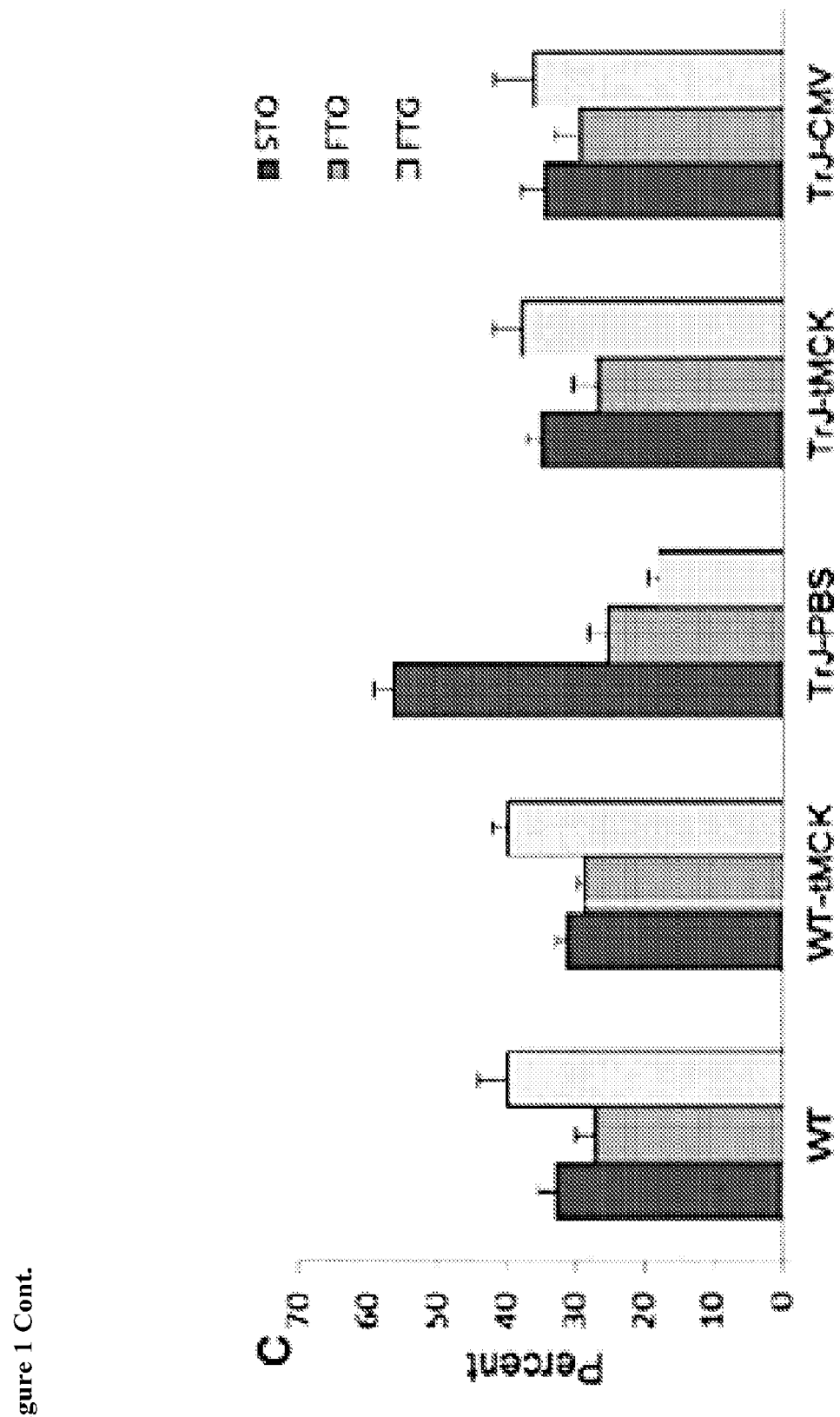

The AAV.NT-3 treatment-induced fiber size increase in the TrJ muscle, was investigated in order to determine whether this increase is solely the consequence of reinnervation, or whether NT-3, has direct effect on muscle protein synthesis that is independent of nerve regeneration and thereby capable of increasing muscle fiber size.

Disclosed herein is a novel effect of NT-3; its ability to directly influence the protein synthesis and metabolic remodeling in neurogenic muscle.

The work described herein, first assessed the effects of AAV.NT-3 gene therapy on the oxidative state of the TrJ muscle at 16 weeks post-gene injection and found that the muscle fiber size increase was associated with a change in the oxidative state of muscle fibers towards normalization of the fiber type ratio seen in the WT. The treatment resulted in a decrease in the percent of slow twitch oxidative (STO) fibers, while fast twitch oxidative and glycolytic (FTO and FTG) fiber populations increased, reflecting a reversal of the pattern seen in the untreated TrJ muscle. NT-3-induced fiber size increase was most prominent for the FTG fiber population. It was then investigated if the mammalian target of rapamycin complex 1 (mTORC1) activation played a role in the NT-3-induced muscle protein synthesis with a particular emphasis on the preferential radial growth of glycolytic fibers. The mTORC1 regulates translation and ribosome biogenesis through the phosphorylation of the translational regulators eukaryotic translation initiation factor 4E binding protein 1 (4E-BP1) and S6 kinase 1 (S6K1). Laplante M, Sabatini D., Cell, 149(2):274-293 (2012). Moreover, mTORC1 is associated with activation of cellular glycolysis, which involves the increased translation of glycolytic enzymes or their transcriptional regulators. Duvel et al., Molecular cell, 39(2):171-183 (2010). It was found that the histochemical changes in the TrJ muscle were accompanied by increased phosphorylation levels of 4E-BP1 and S6 protein (S6P) as evidence of mTORC1 activation. In parallel, the expression levels of mitochondrial biogenesis regulator (peroxisome proliferator-activated receptor y coactivator 1 a, PGC1α), and the markers of glycolysis (hexokinase-1, HK1 and pyruvate kinase 1, PK1) increased in the TrJ muscle. These changes were not significant in AAV.NT-3 treated WT muscle. Furthermore, in vitro studies showed that recombinant NT-3 can directly induce Akt/mTOR pathway activation in the TrkC expressing myotubes but not in myoblasts. Moreover, myogenin expression levels were significantly high in the myotubes while p75NTR expression was downregulated compared to myoblasts, indicating that NT-3 induced myoblast differentiation is associated with mTORC1 activation.

The findings described herein have many implications for the potential use of NT-3, not only for treatment of neuropathies with benefits to both nerve and muscle, but also for muscle wasting conditions including aging, cancer cachexia or type II muscle fiber atrophy as well as genetic or acquired autoimmune primary muscle disorders associated with impaired radial growth phase of regeneration in which perturbations in mTORC1 signaling and defective mitochondrial biogenesis may be involved.

The present disclosure relates to methods of stimulating muscle growth in a subject. The method includes administering a therapeutically effective amount of neurotrophin-3 (NT-3), pro-NT-3, or an effective fragment thereof, or a nucleic acid encoding NT-3, pro-NT-3, or an effective fragment thereof, to a subject in need thereof. Subjects in need of stimulating muscle growth include those having muscular dystrophy or muscle atrophy.

The invention provides for method of inhibiting muscle wasting comprising administering an AAV vector to deliver the neurotrophin-3 (NT-3) encoding NTF3 gene. In one embodiment, the invention provides for gene therapy methods of treating Charcot-Marie-Tooth type 1A (CMT1A) wherein the NT-3 encoding NTF3 gene is delivered to the subject using self-complementary adeno-associated virus (scAAV) type 1 under control of a muscle-specific tMCK promoter. In another embodiment, the invention provides gene therapy methods of increasing muscle strength in subjects in need thereof, e.g. subjects diagnosed or suffering from a muscle wasting disorders such as CMT.

Pre-clinical studies demonstrated that delivery of the construct AAV1.tMCK.NTF3 to the gastrocnemius muscle of the trembler J mice 9 (Tr$^J$), a naturally occurring mouse model for CMT1, improved nerve regeneration, myelination, myelinated fiber density, sciatic nerve compound muscle action potential amplitude and functional performance on rotarod testing and hindlimb grip strength (see Example 3).

As used herein, the terms "treatment", "treating", and the like, refer to obtaining a desired pharmacologic or physiologic effect. The effect may be therapeutic in terms of a partial or complete cure for a disease or an adverse effect attributable to the disease. "Treatment", as used herein, covers any treatment of a disease in a mammal, particularly in a human, and can include inhibiting the disease or condition, i.e., arresting its development; and relieving the disease, i.e., causing regression of the disease.

Prevention, as used herein, refers to any action providing a benefit to a subject at risk of being afflicted with a condition or disease such neuropathy, demyelinating polyneuropathy, muscle wasting disorders or atrophy.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of an agent which will achieve the goal of improvement in disease severity and the frequency of incidence. The effectiveness of treatment may be measured by evaluating a reduction in symptoms in a subject in response to the administration of NT-3.

The term "effective fragment" refers to a portion of the polynucleotide sequence encoding a functional fragment of the NT-3 polypeptide. The term "effective fragment" also refers to a portion of the NT-3 polypeptide amino acid sequence that retains NT-3 growth factor activity. Exemplary NT-3 growth factor activities include supporting the surivival and differentiation of existing neurons, and inducing and supporting the growth and differentiation of new neurons and synapses. In addition, NT-3 activity includes stimulating muscle growth and muscle function.

As used herein, the term "diagnosis" can encompass determining the likelihood that a subject will develop a disease, or the existence or nature of disease in a subject. The term diagnosis, as used herein also encompasses determining the severity and probable outcome of disease or episode of disease or prospect of recovery, which is generally referred to as prognosis). "Diagnosis" can also encompass diagnosis in the context of rational therapy, in which the diagnosis guides therapy, including initial selection of therapy, modification of therapy (e.g., adjustment of dose or dosage regimen), and the like.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). in some embodiments, the subject is a human.

The term "polynucleotide" or "nucleic acid molecule" refers to a polymeric form of nucleotides of at least 10 bases in length. The term includes DNA molecules (e.g., eDNA or genomic or synthetic DNA) and RNA molecules (e.g., mRNA or synthetic RNA), as well as analogs of DNA or RNA containing non-natural nucleotide analogs, non-native inter-nucleoside bonds, or both. The nucleic acid can be in any topological conformation. For instance, the nucleic acid can be single-stranded, double-stranded, triple-stranded, quadruplexed, partially double-stranded, branched, hair-pinned, circular, or in a padlocked conformation.

The term "gene" as used herein refers to a nucleotide sequence that can direct synthesis of an enzyme or other polypeptide molecule (e.g., can comprise coding sequences, for example, a contiguous open reading frame (ORF) which encodes a polypeptide) or can itself be functional in the organism. A gene in an organism can be clustered within an operon, as defined herein, wherein the operon is separated from other genes and/or operons by intergenic DNA. Individual genes contained within an operon can overlap without intergenic DNA between the individual genes.

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

The term "vector" or "expression vector" refers to any type of genetic construct comprising a nucleic acid coding for an RNA capable of being transcribed. Expression vectors can contain a variety of control sequences, structural genes (e.g., genes of interest), and nucleic acid sequences that serve other functions as well.

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably linked to a gene or coding region such that, upon transfection into a recipient cell, an RNA is expressed.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

As used herein, the term "about" refers to +/−10% deviation from the basic value.

Unless defined otherwise, all technical and scientific terms used herein have the same meaning as commonly understood by one of ordinary skill in the art to which this invention belongs.

Gene Therapy of Peripheral Neuropathy

In one aspect, the present invention provides methods of treating a subject having muscular atrophy using gene therapy.

Vectors which can be used to deliver a therapeutic nucleic acid include viral and non-viral vectors. Suitable vectors which can be used include adenovirus, adeno-associated virus, retrovirus, lentivirus, HSV (herpes simplex virus) and plasmids. An advantage of Herpes simplex virus vectors is their natural tropism for sensory neurons. However, adenovirus associated viral vectors are most popular, due to their low risk of insertional mutagenesis and immunogenicity, their lack of endogenous viral genes, and their ability to be produced at high titer. Kantor et al. review a variety of methods of gene transfer to the central nervous system, while Goins et al. describe methods of gene therapy for the treatment of chronic peripheral nervous system pain. See Kantor et al., Adv Genet. 87, 125-197 (2014), and Goins et al., Neurobiol. Dis. 48(2), 255-270 (2012), the disclosures of which are incorporated herein by reference. In particular, successful gene delivery to Schwann cells, the resident glia cells of pierphal nerves, has been reported using various viral vectors. Mason et al., Curr. Gene Ther. 11, 75-89 (2011). If the vector is in a viral vector and the vector has been packaged, then the virions can be used to infect cells. If naked DNA is used, then transfection or transformation procedures as are appropriate for the particular host cells can be used. Formulations of naked DNA utilizing polymers, liposomes, or nanospheres can be used for gene delivery. Nucleic acids can be administered in any desired format that provides sufficiently efficient delivery levels, including in virus particles, in liposomes, in nanoparticles, and complexed to polymers.

The nucleic acid (e.g., cDNA or transgene) encoding a gene whose expression decreases peripheral neuropathy can be cloned into an expression cassette that has a regulatory element such as a promoter (constitutive or regulatable) to drive transgene expression and a polyadenylation sequence downstream of the nucleic acid. For example, regulatory elements that are 1) specific to a tissue or region of the body; 2) constitutive; and/or 3) inducible/regulatable can be used.

In some embodiments, muscle-specific regulatory elements are used. Muscle-specific regulatory elements include muscle-specific promoters including mammalian muscle creatine kinase (MCK) promoter, mammalian desmin promoter, mammalian troponin I (TNNI2) promoter, or mammalian skeletal alpha-actin (ASKA) promoter. Muscle-specific enhancers useful in the present invention are selected from the group consisting of mammalian MCK enhancer, mammalian DES enhancer, and vertebrate troponin I IRE (TNI IRE, herein after referred to as FIRE) enhancer. One or more of these muscle-specific enhancer elements may be used in combination with a muscle-specific promoter of the invention to provide a tissue-specific regulatory element.

A preferred vector for use in treating muscular atrophy by gene therapy is AAV. AAV-mediated gene delivery has emerged as an effective and safe tool for both preclinical and clinical studies of neurological disorders. Ojala et al., Neuroscientist., 21(1):84-98 (2015). Currently, AAV is the most widely used vector for clinical trials for neurological disorders, and no adverse effects linked to the use of this vector have ever been reported from clinical trials: Adeno-associated virus is a non-pathogenic dependovirus from the parvoviridae family requiring helper functions from other viruses, such as adenovirus or herpes simplex virus, to fulfill its life cycle. The wild-type (WT) AAV is characterized by a single-stranded DNA (ssDNA) genome, with inverted terminal repeats (ITR) at both ends, of approximately 5 kb surrounded by a capsid.

Adenoviral vectors for use to deliver transgenes to cells for applications such as in vivo gene therapy and in vitro study and/or production of the products of transgenes, commonly are derived from adenoviruses by deletion of the early region 1 (E1) genes (Berkner, K. L., Curr. Top. Micro. Immunol. 158 L39-66 1992). Deletion of E1 genes renders such adenoviral vectors replication defective and significantly reduces expression of the remaining viral genes present within the vector. Recombinant adenoviral vectors have several advantages for use as gene delivery vehicles, including tropism for both dividing and non-dividing cells, minimal pathogenic potential, ability to replicate to high titer for preparation of vector stocks, and the potential to carry large inserts. However, it is believed that the presence of the remaining viral genes in adenoviral vectors can be deleterious.

Accordingly, in some embodiments, adenoviral vectors with deletions of various adenoviral gene sequences. In particular, pseudoadenoviral vectors (PAVs), also known as 'gutless adenovirus' or mini-adenoviral vectors, are adenoviral vectors derived from the genome of an adenovirus that contain minimal cis-acting nucleotide sequences required for the replication and packaging of the vector genome and which can contain one or more transgenes (See, U.S. Pat. No. 5,882,877 which covers pseudoadenoviral vectors (PAV) and methods for producing PAV, incorporated herein by reference). Such PAVs, which can accommodate up to about 36 kb of foreign nucleic acid, are advantageous because the carrying capacity of the vector is optimized, while the potential for host immune responses to the vector or the generation of replication-competent viruses is reduced. PAV vectors contain the 5' inverted terminal repeat (ITR) and the 3' ITR nucleotide sequences that contain the origin of replication, and the cis acting nucleotide sequence required for packaging of the PAV genome, and can accommodate one or more transgenes with appropriate regulatory elements, e.g. promoter, enhancers, etc.

AAV

Recombinant AAV genomes of the invention comprise nucleic acid molecule of the invention and one or more AAV ITRs flanking a nucleic acid molecule. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12 and AAV-13 (see, e.g., Gao et al., PNAS, 99:11854-11859 ((2002); and Viral Vectors for Gene Therapy: Methods and Protocols, ed. Machida, Humana Press, 2003). Furthermore, pseudotyped AAV vectors may also be utilized in the methods described herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5 capsid and the AAV 2 genome. (Auricchio et al., (2001) Hum. Mol. Genet., 10 (26):3075-81). Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). As noted in the Background section above, the nucleotide sequences of the genomes of various AAV serotypes are known in the art. To promote skeletal muscle specific expression, AAV1, AAV6, AAV8 or AAVrh.74 may be used.

DNA plasmids of the invention comprise rAAV genomes of the invention. The DNA plasmids are transferred to cells permissible for infection with a helper virus of AAV (e.g., adenovirus, E1-deleted adenovirus or herpes virus) for assembly of the rAAV genome into infectious viral particles. Techniques to produce rAAV particles, in which an AAV genome to be packaged, rep and cap genes, and helper virus functions are provided to a cell, are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAVrh.74, AAV-8, AAV-9, AAV-10, AAV-11, AAV-12 and AAV-13. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the invention comprise a rAAV genome. In exemplary embodiments, the genomes of both rAAV lack AAV rep and cap DNA, that is, there is no AAV rep or cap DNA between the ITRs of the genomes. Examples of rAAV that may be constructed to comprise the nucleic acid molecules of the invention are set out in International Patent Application No. PCT/US2012/047999 (WO 2013/016352) incorporated by reference herein in its entirety.

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69 427-443 (2002); U.S. Pat. No. 6,566,118 and WO 98/09657.

In another embodiment, the invention contemplates compositions comprising rAAV of the present invention. Compositions of the invention comprise rAAV and a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or nonionic surfactants such as TWEEN, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg).

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family [See Weintraub et al., Science, 251: 761-766 (1991)], the myocyte-specific enhancer binding factor MEF-2 [Cserjesi and Olson, Mol Cell Biol 11: 4854-4862 (1991)], control elements derived from the human skeletal actin gene [Muscat et al., Mol Cell Biol, 7: 4089-4099 (1987)], the cardiac actin gene, muscle creatine kinase sequence elements [See Johnson et al., Mol Cell Biol, 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors (Semenza et al., Proc Natl Acad Sci USA, 88: 5680-5684 (1991)), steroid-inducible elements and promoters including the glucocorticoid response element (GRE) (See Mader and White, Proc. Natl. Acad. Sci. USA 90: 5603-5607 (1993)), and other control elements.

Muscle tissue is an attractive target for in vivo DNA delivery, because it is not a vital organ and is easy to access. The invention contemplates sustained expression of miRNAs from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of the coding region of NT-3 to a recipient cell either in vivo or in vitro, via a replication-deficient rAAV of the invention resulting in expression of NT-3 by the recipient cell.

In one embodiment, the gene therapy is NT-3 gene therapy via recombinant adeno-associated virus (AAV) delivery. The inventors developed an AAV expression cassette carrying human NT-3 cDNA coding sequence under the control of either the CMV promoter or triple muscle-specific creatine kinase (tMCK) promoter. The inventors have previously shown that an improvement in motor function, histopathology, and electrophysiology of peripheral nerves can be achieved using the recombinant AAV1 vector to increase neurotrophin-3 expression in the tremble (Try) mouse, which is a model for the Charcot-Marie-Tooth disease variant CMT1A. See Sahenk et al., Mol Ther. 22(3):511-21 (2014), the disclosure of which is incorporated herein by reference.

Thus, the invention provides methods of administering an effective dose (or doses, administered essentially simultaneously or doses given at intervals) of rAAV that encode NT-3 to a patient in need thereof.

Doses and Routes of Administration

The invention provides for local administration and systemic administration of an effective dose of rAAV and compositions of the invention including combination therapy of the invention. For example, systemic administration is administration into the circulatory system so that the entire body is affected. Systemic administration includes enteral administration such as absorption through the gastrointestinal tract and parental administration through injection, infusion or implantation.

Routes of administration for the rAAV contemplated in the foregoing methods therefore include, but are not limited to, intraperitoneal (IP), intramuscular (IM) and intravascular [including, for example, inter-arterial limb perfusion (ILP) and intravenous (IV) routes.

The dose of rAAV to be administered in methods disclosed herein will vary depending, for example, on the particular rAAV, the mode of administration, the treatment goal, the individual, and the cell type(s) being targeted, and may be determined by methods standard in the art. More than one dose may be administered, for example, one, two, three or more doses. Titers of rAAV in a dose may range from about $1\times10^6$, about $1\times10^7$, about $1\times10^8$, about $1\times10^9$, about $1\times10^{10}$, about $1\times1^{11}$, about $1\times10^{12}$, about $1.5\times10^{12}$, about $1\times10^{12}$, about $3\times10^{12}$, about $4\times10^{12}$, about $5\times10^{12}$, about $6\times10^{12}$, about $6.5\times10^{12}$, about $7\times10^{12}$, $1\times10^{13}$, about $1\times10^{14}$, or to about $1\times10^{15}$ or more DNase resistant particles (DRP) per ml. Dosages may also be expressed in units of viral genomes (vg) (i.e., $1\times10^7$ vg, $1\times10^8$ vg, $1\times10^9$ vg, $1\times10^{10}$ vg, $1\times10^{11}$ vg, $1\times10^{12}$ vg, about $1.5\times10^{12}$ vg, about $1\times10^{12}$ vg, about $3\times10^{12}$ vg, about $4\times10^{12}$ vg, about $5\times10^{12}$ vg, about $6\times10^{12}$ vg, about $6.5\times10^{12}$ vg, about $7\times10^{12}$ vg, $1\times10^{13}$ vg, $1\times10^{14}$ vg, $1\times10^{15}$ respectively). Methods for titering AAV are described in Clark et al., *Hum. Gene Ther.*, 10: 1031-1039 (1999).

In some embodiments of the foregoing methods in which the route of administration is an IM route, the dose of the rAAV administered is from about $1.5\times10^{12}$ to at least about $6.5\times10^{12}$ vg/kg. (All ranges herein are intended to represent each individual value in the ranges, as well as the individual upper and lower values of each range.) In some embodiments of the foregoing methods in which the route of administration is IM, the dose of the rAAV administered is $2\times10^{12}$ vg/kg. In some embodiments of the foregoing methods in which the route of administration is IM, the dose of the rAAV administered is $4\times10^{12}$ vg/kg. In some embodiments of the foregoing methods in which the route of administration is IM, the dose of the rAAV administered is $6\times10^{12}$ vg/kg.

Human patients are subjects contemplated herein for treatment. Human patients are subjects contemplated herein for treatment by IM delivery. Such patients include those patients that, e.g.: i) adult subjects (>18 years) diagnosed with CMT1A, ii) exhibit a 1.5 Mb duplication at 17p11.2 inclusive of the peripheral myelin protein 22 (PMP22) gene, iii) males and females of any ethnic or racial group, iv) exhibit weakness of the ankle dorsiflexion muscle (should have full ROM against gravity but cannot maintain full dorsiflexion against gravity or able to stand heels 3 seconds or greater (Northstar criteria)), iv) abnormal nerve conduction velocities, v) ability to cooperate for clinical evaluation and repeat nerve conduction studies, and vi) willingness of sexually active subjects to practice a reliable method of contraception during the study. Suitable patients may not include, e.g., those with i) active viral infection based on clinical observations or serological evidence of HIV, or Hepatitis A, B or C infection, ii) ongoing immunosuppressive therapy or immunosuppressive therapy within 6 months of starting the trial (e.g., corticosteroids, cyclosporine, tacrolimus, methotrexate, cyclophosphamide, intravenous immunoglobulin), iii) persistent leukopenia or leukocytosis (WBC≤3.5 K/μL or ≥20.0 K/μL) or an absolute neutrophil count <1.5K/μL, iv) AAV1 binding antibody titers ≥1:50 as determined by ELISA immunoassay, v) concomitant illness or requirement for chronic drug treatment that in the opinion of the PI creates unnecessary risks for gene transfer, vi) ankle contractures or surgeries preventing proper muscle strength testing, vii) pregnancy, breast feeding, or plans to become pregnant, viii) other causes of neuropathy, and/or ix) limb surgery in the past six months. In an exemplary clinical protocol, CMT1A patients receive a total dose of vector scAAV1.tMCK.NTF3 divided into medial and lateral heads of the gastrocnemius and tibialis anterior (TA) muscles of legs which are preferentially causing ankle weakness and instability in CMT. Subjects receive one of the following: i) low dose of vector of $2\times10^{12}$ vg/kg (total dose) or ii) a high dose of vector of $6\times10^{12}$ vg/kg (total dose).

In one embodiment, the vector is administered by IM injection without diluent. In alternative embodiments, compositions for intramuscular injection include an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical carriers, diluents or excipients suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

In another aspect, rAAV genomes are provided herein. The genomes of the rAAV administered comprise a NT-3 polynucleotide under the control of transcription control sequences. The rAAV genomes lack AAV rep and cap DNA. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11 and AAVrh.74. The nucleotide sequences of the genomes of these AAV serotypes are known in the art as noted in the Background Section above.

In some embodiments, the transcription control sequences of the rAAV genomes are muscle-specific control elements, including, but not limited to, those derived from the actin and myosin gene families, such as from the myoD gene family [See Weintraub et al., *Science*, 251: 761-766 (1991)], the myocyte-specific enhancer binding factor MEF-2 [Cserjesi and Olson, *Mol. Cell. Biol.*, 11: 4854-4862 (1991)], control elements derived from the human skeletal actin gene [Muscat et al., *Mol. Cell. Biol.*, 7: 4089-4099 (1987)], the cardiac actin gene, muscle creatine kinase (MCK) promoter [Johnson et al., Mol. Cell. Biol., 9:3393-3399 (1989)] and the MCK enhancer, MHCK7 promoter (a modified version of MCK promoter that incorporates an enhancer from myosin heavy chain (Salva et al., *Mol. Ther.*, 15: 320-329 (2007)), desmin promoter, control elements derived from the skeletal fast-twitch troponin C gene, the slow-twitch cardiac troponin C gene and the slow-twitch troponin I gene: hypozia-inducible nuclear factors (Semenza et al., *Proc. Natl. Acad. Sci. USA*, 88: 5680-5684 (1991)), steroid-inducible elements and promoters including the glucocorticoid response element (GRE) (See Mader and White, *Proc. Natl. Acad. Sci. USA*, 90: 5603-5607 (1993)), and other control elements. In some embodiments, the transcription control elements include the MCK promoter. In some embodiments, the transcription control elements include the MHCK7 promoter.

In some embodiments, the NT-3 polynucleotide in a rAAV genome is the NT-3 cDNA set out in SEQ ID NO: 1 (corresponding to nucleotides 1077-1850 of SEQ ID NO: 11). In some embodiments, the NT-3 polynucleotide in a rAAV genome is the NT-3 cDNA set out in Genbank Accession #NM_001102654 or the NT-3 cDNA sequence set out as SEQ ID NO: 1, or is a variant polynucleotide having 80%, 81%, 82%, 83%, 84%, 85%, 86%, 87%, 88%, 89%, 90%, 91%, 92%, 93%, 94%, 95%, 96%, 97%, 98% or 99% sequence identity to the NT-3 cDNA. In some embodiments, the variant NT-3 polynucleotide encodes the same NT-3 polypeptide as the polypeptide encoded by NT-3 cDNA of SEQ ID NO: 1. The amino acid sequence of the NT-3 polypeptide encoded by the NT-3 cDNA set out as SEQ ID NO: 1 or provided as Genbank Accession #NM_001102654 is set out in SEQ ID NO:2. In some embodiments, the variant NT-3 polynucleotide encodes a variant NT-3 polypeptide with at least one amino acid sequence alteration as compared to the amino acid sequence of the polypeptide (SEQ ID NO: 2) encoded by NT-3 cDNA set out in SEQ ID NO: 1 or provided as Genbank Accession #NM_001102654. An amino acid sequence alteration can be, for example, a substitution, a deletion, or an insertion of one or more amino acids, preferably conservative substitutions. A variant NT-3 polypeptide can have any combination of amino acid substitutions, deletions or insertions where activity of the polypeptide is retained. In one aspect, a variant NT-3 polypeptide can have a number of amino acid alterations such that its amino acid sequence shares at least 60, 70, 80, 85, 90, 95, 97, 98, 99 or 99.5% identity with the amino acid sequence (SEQ ID NO: 2) encoded by NT-3 cDNA set out as SEQ ID NO: 1 or provided as Genbank Accession #NM_001102654.

In some embodiments, the rAAV genome is the AAV.tMCK.NTF3 genome, the sequence of the NT-3 gene cassette of which is set out in SEQ ID NO: 11 and is annotated in Table 4 (see Example 3).

In yet another aspect, an isolated nucleic acid comprising the nucleotide sequence depicted in SEQ ID NO: 11 is provided. In some embodiments, the isolated nucleic acid consists of the nucleotide sequence depicted in SEQ ID NO:11.

Also provided is an isolated nucleic acid comprising, in order from 5' to 3': (i) a first AAV2 inverted terminal repeat sequence (ITR) (SEQ ID NO: 4); (ii) a muscle creatine kinase promoter sequence (SEQ ID NO: 3); (iii) a nucleotide sequence encoding a human NT-3 polypeptide (SEQ ID NO: 1); and (iv) a second AAV2 ITR sequence (SEQ ID NO: 8), wherein the human NT-3 polypeptide has an amino acid sequence that is at least 90% identical to SEQ ID NO: 2, is 100% identical to SEQ ID NO:2, or is encoded by nucleotides 1077-1850 of SEQ ID NO: 11.

Recombinant AAV comprising the foregoing nucleic acids are contemplated as well as rAAV comprising a nucleotide sequence that is at least 90% identical to the nucleotide sequence depicted in SEQ ID NO: 1.

DNA plasmids comprising rAAV genomes of the disclosure are provided. The DNA plasmids comprise rAAV genomes contemplated herein. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11 and AAV rh74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014).

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982,

*Proc. Natl. Acad. S6. USA,* 79:2077-2081), addition of synthetic linkers containing restriction endonuclease cleavage sites (Laughlin et al., 1983, *Gene,* 23:65-73) or by direct, blunt-end ligation (Senapathy & Carter, 1984, *J. Biol. Chem.,* 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells. Methods for producing rAAV with self-complementary genomes are also known in the art.

General principles of rAAV production are reviewed in, for example, Carter, 1992, *Current Opinions in Biotechnology,* 1533-539; and Muzyczka, 1992, *Curr. Topics in Microbial. and Immunol.,* 158:97-129). Various approaches are described in Ratschin et al., *Mol. Cell. Biol.* 4:2072 (1984); Hermonat et al., *Proc. Natl. Acad. Sci. USA,* 81:6466 (1984); Tratschin et al., *Mol. Cell. Biol.* 5:3251 (1985); McLaughlin et al., *J. Virol.,* 62:1963 (1988); and Lebkowski et al., 1988 *Mol. Cell. Biol.,* 7:349 (1988). Samulski et al. (1989, *J. Virol.,* 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) *Vaccine* 13:1244-1250; Paul et al. (1993) *Human Gene Therapy* 4:609-615; Clark et al. (1996) *Gene Therapy* 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

In a further aspect, the disclosure thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.,* 10(6): 1031-1039 (1999); Schenpp and Clark, *Methods Mol. Med.,* 69 427-443 (2002); U.S. Pat. No. 6,566,118 and WO 98/09657.

Thus, in another aspect, the disclosure contemplates a rAAV comprising a NT-3 polynucleotide. In some embodiments, the rAAV comprises AAV rh74 capsid and a NT-3 polynucleotide. In some embodiments, the genome of the rAAV lacks AAV rep and cap DNA. In some embodiments of the methods, the rAAV is rAAVrh7.4.tMCK.NTF3. In some embodiments, the rAAV is a self-complementary genome.

In another aspect, the disclosure contemplates compositions comprising a rAAV described herein. Compositions of the disclosure comprise rAAV in a pharmaceutically acceptable carrier. The compositions may also comprise other ingredients such as diluents. Acceptable carriers and diluents are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, pluronics or polyethylene glycol (PEG). In some embodiments, the rAAV is formulated in Tris, $MgCl_2$, NaCl and pluronic F68. In some embodiments, the rAAV is formulated in 20 mM Tris (pH 8.0), 1 mM $MgCl_2$ and 200 mM NaCl containing 0.001% pluronic F68.

Combination treatments are also contemplated herein. Combinations as used herein include simultaneous treatment or sequential treatments. Combinations of methods of the disclosure with standard medical treatments (e.g., corticosteroids and/or immunosuppressive drugs) are specifically contemplated, as are combinations with novel treatments. In various embodiments, subjects are treated with corticosteroids before, during or after (or with any permutation of combinations of two or more of the three possibilities), the subject is treated according to a method contemplated herein. For example, the combinations include administering a corticosteroid, e.g. prednisolone, before, during and/or after administration of the rAAV vector.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Stimulating Muscle Growth

One aspect of the invention provides a method of stimulating muscle growth in a subject, comprising administering a therapeutically effective amount of neurotrophin-3 (NT-3), pro-NT-3, or an effective fragment thereof, or a nucleic acid encoding NT-3, pro-NT-3, or an effective fragment thereof; to a subject in need thereof In some embodiments, the methods of the invention may be used to increase muscle strength, muscle mass, or muscle endurance and decrease muscle fatigue in a subject.

Muscle can be divided into three types: skeletal muscle, cardiac muscle, and smooth muscle. Skeletal muscle is muscle tissue capable of generating force and transferring that force to the skeleton enables breathing, movement, and posture maintenance. Cardiac muscle is muscle of the heart. Smooth muscle is muscle tissue of the arterial and bowel walls. The methods and compositions of the present invention apply primarily to skeletal muscle and, but may additionally positively affect smooth muscles. "Skeletal muscle" and "skeletal muscles" are defined as muscles with interactions with bones, tendons, and joints.

In some embodiments, the present invention provides a method of treatment of illnesses, diseases, disorders, and conditions that cause a decrease in muscle strength (also referred to herein as musculoskeletal diseases, and as muscle dysfunction and muscle-wasting diseases). The main categories of musculoskeletal diseases are muscular dystrophies and muscular atrophy.

In some embodiments, the invention provides methods for the treatment of musculoskeletal diseases, including muscle dysfunction and muscle-wasting diseases or disorders, including hereditary myopathy, neuromuscular disease, muscular atrophy, drug-induced. myopathy, or an illness, disease, disorder or condition that causes a decrease in muscle strength. The invention also provides for methods for the treatment of neuropathies such as CMT-hereditary and CMT1A, as well as axonal and demyelinating polyneuropathies such as chronic inflammatory demyelinating polyneuropathy. The method of treatment includes administering to a patient in need thereof a therapeutically effective amount of neurotrophin-3 (NT-3), pro-NT-3, or an effective fragment thereof, or a nucleic acid encoding NT-3, pro-NT-3, or an effective fragment thereof. In some embodiments, the subject has a muscle disease selected from the group consisting of sarcopenia, cachexia, type II muscle fiber atrophy and acquired autoimmune primary muscle disorders associated with impaired radial growth phase of regeneration.

In some embodiments, NT-3 can be used to treat muscular atrophy. Muscular atrophy is a general term used to describe a condition marked by the wasting or loss muscle tissue resulting from a variety of diseases, disorders, other conditions, or events. Muscle atrophies can be the result of, but are not limited to, protracted immobilization resulting from recovery from severe burns, major joint replacement surgery, neuropathic pain, peripheral neuropathy, necrotizing vasculitis, zero gravity environment (e.g., astronauts and cosmonauts), extended hospitalization, degenerative disease (e.g., amyotrophic lateral sclerosis) and organ transplant as well as spinal cord injury, chronic hemodialysis, and stroke.

In some embodiments, NT-3 can be used to treat disuse muscular atrophy. Disuse muscular atrophy is a condition marked by the wasting or loss muscle tissue resulting from long periods of inactivity. Disuse muscular atrophy can be result of, but are not limited to, protracted immobilization resulting from recovery from severe burns, major joint replacement surgery, neuropathic pain, zero gravity environment (e.g., astronauts and cosmonauts), extended hospitalization, anorexia, and. organ transplant as well as spinal cord injury, chronic hemodialysis, and stroke.

In some embodiments, NT-3 can be used to treat age-related muscular atrophy. Age-related muscular atrophy is a condition marked by the wasting or loss muscle tissue and the replacement of muscle tissue with fibrosis tissue as the subject ages.

In some embodiments, NT-3 can be used to treat sarcopenia. Sarcopenia is a condition marked by the wasting or loss muscle tissue and the replacement of muscle tissue with fibrosis tissue as the subject ages.

In some embodiments, NT-3 can be used to treat the muscle wasting in cachexia. Cachexia is loss of weight, muscle atrophy, fatigue, weakness and significant loss of appetite in someone who is not actively trying to lose weight, but rather as the result of chronic disease. The muscle wasting component of cachexia can be result of, but are not limited to, cancer, multiple sclerosis, tuberculosis, acquired immune deficiency syndrome, human immunodeficiency virus, malnutrition, Parkinson's disease, emphysema, heart failure, motor neuron disease, cystic fibrosis, dementia, sarcopenia, chronic obstructive pulmonary disease, kidney disease, and kidney failure.

In some embodiments, NT-3 can be used to treat muscle wasting resulting from viral infections (e.g., HIV, Epstein-Barr virus), bacterial infections (e.g., mycobacteria and rickettsia), post-polio syndrome, and parasitic infection (e.g., trypanosomes and schistosome) wherein the subject is at risk of developing muscle atrophy.

Neurotophin-3

In some embodiments, a therapeutically effective amount of NT-3, pro-NT-3, or an NT-3 analog thereof is administered to the subject to stimulate muscle growth. Neurotrophin 3 (NT-3) is a neurotrophic factor in the NGF (Nerve Growth Factor) family of neurotrophins. NT-3 is a protein growth factor which has activity on certain neurons of the peripheral and central nervous system; it is best known for helping to support the survival and differentiation of existing neurons, and encourages the growth and differentiation of new neurons and synapses.

The disclosure includes blocking peptides that are substantially similar to at least a portion of the amino acid sequence of an extracellular domain of Cx26. The term "a portion," as used herein, refers to an amino acid sequence within the extracellular domains of Cx26 that includes at least 4 amino acids. In further embodiments, a portion refers to an amino acid sequence that is at least 6 amino acids in length, an amino acid sequence that is at least 8 amino acids in length, or an amino acid sequence that is at least 10 amino acids in length. The blocking peptides therefore consist of at least 4, 6, 8, or 10 amino acids. Likewise, the blocking peptides described herein can have a maximum size. The maximum size of the blocking peptide relates to the overall size of the peptide, and includes any additional sequences linked to the peptide, such as a protein transduction domain. In some embodiments, the blocking peptide has a maximum size of less than about 200 amino acids, while in other embodiments the blocking peptide has a maximum size of less than about 100 amino acids. In other embodiments, the blocking peptide has a maximum size of 75 amino acids or less, 50 amino acids or less, 40 amino acids or less, 30 amino acids or less, or 20 amino acids or less.

As used herein, the term "polypeptide" refers to an oligopeptide, peptide, or protein sequence, or to a fragment, portion, or subunit of any of these, and to naturally occurring or synthetic molecules. The term "polypeptide" also includes amino acids joined to each other by peptide bonds or modified peptide bonds, i.e., peptide isosteres, and may contain any type of modified amino acids, The term "polypeptide" also includes peptides and polypeptide fragments, motifs and the like, glycosylated polypeptides, all "mimetic" and "peptidomimctic" polypeptide forms, and retro-inversion peptides (also referred to as all-D-retro or mtro-enantio peptides).

"Substantially similar" means that a given amino acid (or nucleic acid) sequence shares at least 85%, more preferably at least 90%, and even more preferably at least 95% identity with a reference sequence. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence. shall not be construed as affecting homology.

Substantially similar peptides include those that differ by one or more amino acid alterations, where the alterations, e.g., substitutions, additions or deletions of amino acid residues, do not abolish the properties of the relevant peptides, such as their ability to associate with FAK or NANOG.

Furthermore, only sequences describing or encoding proteins in which only conservative substitutions are made in the conserved regions are substantially similar overall. Preferable, substantially similar sequences also retain the distinctive activity of the poly peptide.

Examples of conservative substitutions include the substitution of a non-polar (hydrophobic) residue such as isoleucine, leucine, or methionine for another. Likewise, the present invention contemplates the substitution of one polar (hydrophilic) residue such as between arginine and lysine, between glutamine and asparagine, and between glycine and serine. Additionally, the substitution of a basic residue such as lysine, arginine or histidine for another or the substitution of one acidic residue such as aspartic acid or glutamic acid for another is also contemplated. Examples of non-conservative substitutions include the substitution of a non-polar (hydrophobic) residue such as isoleucine, valine, leucine, alanine, methionine for a polar (hydrophilic) residues such as cysteine, glutamine, glutamic acid, lysine. and/or a polar residue for a non-polar residue.

The phrase "conservative substitution" also includes the use of chemically derivatized residues in place of a non-derivatized residues as long as the peptide retains the requisite ability to associate with NT-3. Substantially similar peptides also include the presence of additional amino acids or the deletion of one. or more amino acids which do not affect the requisite ability to associate with NT-3, For example, substantially similar peptides can contain an N- or C-. terminal cysteine, by which, if desired, the peptide may be covalently attached to a carrier protein, e.g., albumin. Such attachment can decrease clearing of the peptide from the blood and also decrease the rate of proteolysis of the peptides. In addition, for purposes of the present. invention, peptides containing D-amino acids in place of L-amino acids are also included in the term "conservative substitution." The presence of such D-isomers can. help minimize proteolytic activity and clearing of the peptide.

In some embodiments, a pro-neurotrophin-3 protein (pro-NT-3) is administered to the subject. The pro form of neurotrophin-3 is a ~30 kDa precursor form of NT-3 which is converted to the mature NT by enzymatic cleavage and removal of a ~15 kDa N-terminal prodomain. See Tauris et al., Eur. J Neurosci, 33(4), 622-631 (2011).

Treatment of Muscular Atrophy

The present invention provides a method of treating a subject having periperhal muscle atrophy. Pyruvate compounds can be used to provide prophylactic and/or therapeutic treatment. Pyruvate compounds can, for example, be administered prophylactically to a subject in advance of the occurrence of peripheral neuropathy. Prophylactic (i.e., preventive) administration is effective to decrease the likelihood of the subsequent occurrence of peripheral neuropathy in the subject, or decrease the severity of peripheral neuropathy that subsequently occurs. Prophylactic treatment may be provided to a subject that is at elevated risk of developing peripheral neuropathy, such as a subject with a family history of peripheral neuropathy. The expression of mutations of myelin protein 22 (PMP22) represents 70-80% of all occurrences of Charcot-Marie-Tooth neuropathy, and thus their presence may be useful as criteria for selecting patients to receive treatment using the pyruvate compounds described herein.

Alternatively, the compounds of the invention can be administered therapeutically to a subject that is already afflicted by peripheral neuropathy. In one embodiment of therapeutic administration, administration of the compounds is effective to eliminate the peripheral neuropathy; in another embodiment, administration of the pyruvate compounds is effective to decrease the severity of the peripheral neuropathy or lengthen the lifespan of the subject so afflicted. In some embodiments, the method of treatment consists of administering a therapeutically effective amount of a pyruvate compound in a pharmaceutically acceptable formulation to the subject over a substantial period of time.

CMT Variants

Charcot-Marie-Tooth (CMT) hereditary neuropathy refers to a group of disorders characterized by a chronic motor and sensory polyneuropathy, also known as hereditary motor and sensory neuropathies. The autosomal dominant CMT neuropathy types are: demyelinating (also referred to as CMT1), axonal non-demylinating (also referred to as CMT2) and dominant intermediate CMT (DI-CMT). Other neuropathies that are also equivalent to CMT are distal hereditary motor neuropathy 9dHMN) and distoal spinal muscular atrophy (DSMA) and Dejerine-Sottas syndrome (DSS). Descriptions and classifications of CMT neurophathies are provided in Bird, GeneReviews, Seattle Washington: University of Washington Seattle PIM 20301532, Updated 2018 Jun. 28.

Currently, there are over 70 known genetic variants known to CMT-associated genes. These genetic variants are provided in Table 1 below using the classification system of Magy et al. (Neurology 90:e870-6, 2018). The mode of inherence for each CMT-associated genetic variants are autosomal dominant (AD), autosomal recessive (AR) or X Linked (XL). The neuropathy for each CMT-associated genetic variant are axonal (Ax), demyelinating (De) and intermediate (In). The "other designations" provided in Table 1 are designations used in other classification systems which include dominate intermediate CMT (DI-CMT), distal spinal muscular dystrophy (DSMA), hereditary sensory and autonomic neuropathy (HSAN) and distal hereditary motor neuropathy (dHMN).

TABLE 1

| Gene [1] | MOI | Neuropathy Type | | | Other Phenotypic Features/ Comments | Other Designations [2] |
|---|---|---|---|---|---|---|
| | | Ax | De | In | | |
| GDAP1 | AR | ● | | | Vocal cord paresis [4] | CMT2K |
| | AR | ● | ● | ● | | CMT4A |
| | | | | | | CMT2H |
| | | | | | | CMT2K |
| | | | | | | CMTRIA |
| | AD, AR | ● | | | | |
| GJB1 | XL | ● | | | Family history may appear to be AD as females can be as severely affected as males. | CMTX1 |
| HINT1 | AR | ● | | | Neuromyotonia | |
| MFN2 | AD, AR | ● | | | Optic atrophy | CMT2A2 CMT2I/2J |
| MPZ | AD | ● | ● | ● | | CMT1B CMT2I/J DI-CMTD |
| PMP22 | AD | | ● | | | CMT1A CMT1E |
| SH3TC2 | AR | ● | | | | CMT4C |
| AARS | AD | ● | | | | CMT2N |
| ABHD12 | AR | | | ● | Deafness, cataract, retinitis pigmentosa | PHARC |
| AIFM1 | XL | ● | | | Deafness, intellectual disability | CMTX4 |
| ARHGEF10 | AD | | | ● | | |
| ATP1A1 | AD | ● | | | | |
| ATP7A [5] | XL | ● | | | Distal lower extremities | |

TABLE 1-continued

Figure 4:
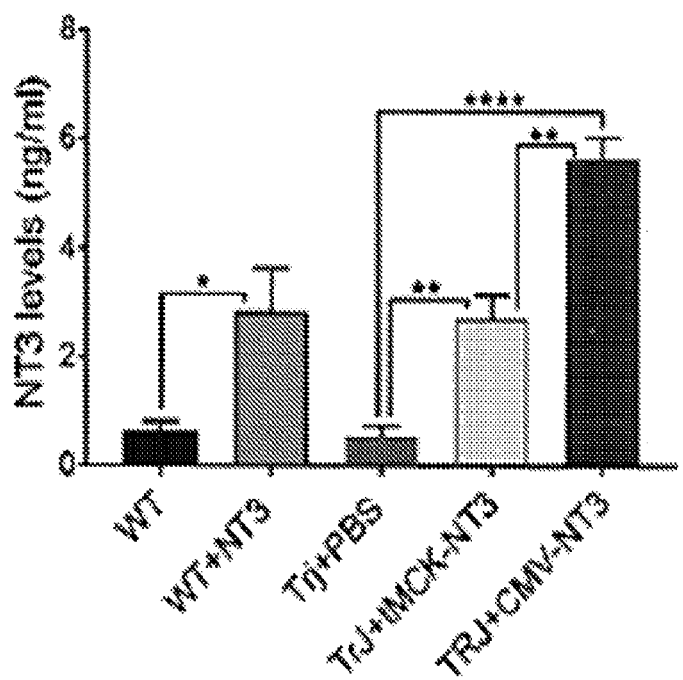
FIG. 4 provides a graph showing serum levels of NT-3 in treated and non treated mice. At the Endpoint serum was collected from each mouse and circulating NT-3 levels were detected by ELISA.

| Gene [1] | MOI | Ax | De | In | Other Phenotypic Features/ Comments | Other Designations [2] |
|---|---|---|---|---|---|---|
| BAG3 | AD | ● | | | Myofibrillar myopathy, cardiomyopathy | |
| BSCL2 | AD | ● | | | Distal lower extremities; UMN involvement can cause spastic paraplegia | dHMN5A |
| CNTNAP1 | AR | ● | ● | | Arthrogryposis, leukodystrophy | |
| COA7 | AR | ● | | | | |
| DCTN1 | AD | | | | Distal lower extremities | dHMN7B |
| DCTN2 | AD | ● | | | Vocal cord paresis [4] | |
| DGAT2 | AD | ● | | | | |
| DHTKD1 | AD | ● | | | | CMT2Q |
| DNAJB2 | AR | ● | | | Distal motor neuropathy | DSMA5 |
| DNMT1 | AD | ● | | | Hearing loss, dementia | DMNT1 |
| DNM2 | AD | | | ● | | CMT2M DI-CMTB |
| DRP2 | XL | | | ● | Autism | |
| DYNC1H1 | AD | ● | | | SMA | CMT2O |
| EGR2 | AD | | ● | | | CMT1D |
| | AR | | ● | | | CMT4E |
| FGD4 | AR | | ● | | | CMT4H |
| FIG4 | AR | | ● | | | CMT4J |
| GARS | AD | ● | | | Onset in hands | CMT2D dHMN5A |
| GNB4 | AD | | | ● | | DI-CMTF |
| HARS | AD | ● | ● | | | CMT2W |
| HSPB1 | AD | ● | | | | CMT2F |
| HSPB3 | AD | | | | | dHMN2B dHMN2C |
| HSPB8 | AD | ● | | | Adult onset | CMT2L dHMN2A |
| IGHMBP2 | AR | ● | | | | CMT2S DSMA1 |
| INF2 | AD | | | ● | Glomerulosclerosis | |
| KIF1B | AD | ● | | | | CMT2A1 |
| KIF5A | AD | ● | | | Spasticity | |
| LITAF | AD | | ● | | | CMT1C |
| LMNA | AR | ● | | | | CMT2B1 |
| LRSAM1 | AD | ● | | | | CMT2G |
| | AR | | | | | CMT2P |
| MARS | AD | ● | | | | CMT2U |
| MCM3AP | AR | ● | ● | | Childhood onset, severe | |
| MED25 | AR | ● | | | | CMT2B2 |
| MME | AR | ● | | | | CMT2T |
| | AD | | | | | |
| MORC2 | AD | ● | | | | CMT2Z |
| MPV17 | AR | ● | | | Navaho neurohepatopathy | |
| MPZ | AD | ● | ● | ● | | CMT1B CMT2I/J DI-CMTD |
| MTMR2 | AR | | ● | | Vocal cord paresis [4] | CMT4B1 |
| NAGLU | AD | ● | | | | CMT2V |
| NDRG1 | AR | | ● | | | CMT4D |
| NEFH | AD | ● | | | | |
| NEFL | AD, AR | ● | ● | | | CMT1F/2E |
| PDK3 | XL | ● | | | | CMTX6 |
| PLEKHG5 | AR | | | ● | Distal predominant | DSMA4 |
| PRPS1 | XL | ● | | | Retinopathy, deafness | CMTX5 |
| PRX | AR | ● | | | | CMT4F |
| PTRH2 | AR | | | | Hearing loss | |
| RAB7A | AD | ● | | | Prominent sensory loss | CMT2B |
| SBF1 | AR | ● | | | | CMT4B3 |
| SBF2 | AR | | ● | | | CMT4B2 |
| SCO2 | AR | ● | | | Motor neuropathy | |
| SETX | AD | | | | Distal lower extremities | FALS |
| SIGMAR1 | AR | ● | | | Motor neuropathy | |
| SGPL1 | AR | ● | | | Recurrent mononeuropathy | |
| SPG11 | AR | ● | | | Spasticity, cognitive decline | CMT2X ALS5 |
| SPTLC1 | AD | ● | | | | HSAN1A |
| TRIM2 | AR | ● | | | Vocal cord paresis [4] | CMT2R |
| TRPV4 | AD | ● | | | Vocal cord paresis [4], skeletal dysplasia | CMT2C |
| VCP | AD | ● | | | Inclusion body myopathy, dementia | CMT2Y |
| WARS | AD | ● | | | Motor neuropathy | dHMN9 |
| YARS | AD | | | ● | | DI-CMTC |
| Unknown [6] | XL | | | ● | Rapid progression, severe hand weakness | CMTX3 |

MOI = mode of inheritance
AD = autosomal dominant
AR = autosomal recessive
XL = X-linked
Ax = axonal
De = demyelinating
In = intermediate
UMN = upper motor neuron
DI-CMT = dominant intermediate CMT
DSMA = distal spinal muscular atrophy
ALS = amyotrophic lateral sclerosis
HSAN = hereditary sensory and autonomic neuropathy
dHMN = distal hereditary motor neuropathy Administration and Formulation The vector or peptide used with some embodiments of the present invention can be incorporated into pharmaceutical compositions suitable for administration to a subject. In some particular embodiments, the pharmaceutical composition comprises the vector of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it can be preferable to include isotonic agents, for example, sugars, polyalcohols such as mannitol, sorbitol, or sodium chloride in the composition. Pharmaceutically acceptable carriers can further comprise minor amounts of auxiliary substances such as wetting or emulsifying agents, preservatives or buffers, which enhance the shelf life or effectiveness of the vector or pharmaceutical composition.

The vectors or peptides can be administered acutely (i.e., during the onset or shortly after events leading to muscular atrophy), or can be administered prophylactically (e.g., before scheduled surgery, or before the appearance of signs or symptoms), or can be administered during the course of muscular atrophy to reduce or ameliorate the progression of symptoms that would otherwise occur. The timing and interval of administration is varied according to the subject's symptoms, and can be administered at an interval of several hours to several days, over a time course of hours, days, weeks or longer, as would be determined by one skilled in the art.

The compositions containing the vectors or peptides are generally administered intravenously. When administered intravenously, the compositions may be combined with other ingredients, such as carriers and/or adjuvants. Peptides may also be covalently attached to a protein carrier, such as albumin, so as to minimize clearing of the peptides. There are no limitations on the nature of the other ingredients, except that such ingredients must be pharmaceutically acceptable, efficacious for their intended administration and cannot degrade the activity of the active ingredients of the compositions.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants or vegetable oils. Sterilization can be accomplished by any art-recognized technique, including but not limited to, filtration or addition of antibacterial or antifungal agents, for example, paraben, chlorobutano, phenol, sorbic acid or thimerosal. Further, isotonic agents such as sugars or sodium chloride may be incorporated in the subject compositions.

Production of sterile injectable solutions containing the subject peptides is accomplished by incorporated these compounds in the required amount in the appropriate solvent with various ingredients enumerated above, as required, followed by sterilization, preferably filter sterilization. To obtain a sterile powder, the above solutions are vacuum-dried or freeze-dried as necessary.

When the peptides of the invention are administered orally, the pharmaceutical compositions thereof containing an effective dose of the peptide can also contain an inert diluent, as assimilable edible carrier and the like, be in hard or soft shell gelatin capsules, be compressed into tablets, or may be in an elixir, suspension, syrup or the like. The subject peptides are thus compounded for convenient and effective administration in pharmaceutically effective amounts with a suitable pharmaceutically acceptable carrier in a therapeutically effective amount.

The expressions "effective amount" or "therapeutically effective amount," as used herein, refers to a sufficient amount of agent to stimulate muscle growth or decrease or prevent muscle atrophy. The exact amount required will vary from subject to subject, depending on the species age, and general condition of the subject, the particular therapeutic agent, its mode and/or route of administration, and the like. It will be understood, however, that the total daily usage of the compounds and compositions of the present invention can be decided by an attending physician within the scope of sound medical judgment. The specific therapeutically effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific composition employed; the duration of the treatment; drugs used in combination or coincidental with the specific composition employed; and like factors well known in the medical arts.

The vectors or peptides can be administered in a manner compatible with the dosage formulation and in such amount as well be therapeutically effective. Systemic dosages depend on the age, weight and conditions of the patient and on the administration route. For example, a suitable dose of peptide for. the administration to adult humans ranges from about 0.001 to about 20.0 mg per kilogram of body weight. The peptides should preferably be administered in an amount of at least about 50 mg per dose, more preferably in an amount up to about 500 mg to about 1 gram per dose. Since the peptide compositions of this invention will eventually be cleared from the bloodstream, re-administration of the compositions is indicated and preferred.

EXAMPLES

Thus, aspects and embodiments of the invention are illustrated by the following examples. However, there are a wide variety of other embodiments within the scope of the present invention, which should not be limited to the particular examples provided herein.

Example 1

AAV1.NT-3 Gene Therapy Increases Muscle Fiber Diameter Through Activation of mTOR Pathway and Metabolic Remodeling in a CMT Mouse Model NT-3 has well-recognized effects on peripheral nerve and Schwann cells, promoting axonal regeneration and associated myelination. The effects of AAV.NT-3 gene therapy on the oxidative state of the neurogenic muscle from the Trembled (TrJ) mice at 16 weeks post-gene injection were assessed and found that muscle fiber size increase was associated with a change in the oxidative state of muscle fibers towards normalization of the fiber type ratio seen in the wild type. NT-3-induced fiber size increase was most prominent for the fast twitch glycolytic fiber population. These changes in the TrJ muscle were accompanied by increased phosphorylation levels of 4E-BP1 and S6 protein as evidence of mTORC1 activation. In parallel, the expression levels of mitochondrial biogenesis regulator PGC 1α, and the markers of glycolysis (HK1 and PK1) increased in the TrJ muscle. In vitro studies showed that recombinant NT-3 can directly induce Akt/mTOR pathway activation in the TrkC expressing myotubes but not in myoblasts. Along with, myogenin expression levels were significantly high in the myotubes while p75NTR expression was downregulated compared to myoblasts, indicating that NT-3 induced myoblast differentiation is associated with mTORC1 activation. These studies for the first time have shown that NT-3 increases muscle fiber diameter in the neurogenic muscle through direct activation of mTOR pathway and that the fiber size increase is more prominent for fast twitch fibers.

Methods

Animals, treatment protocols and histopathology: TrJ mice (B6.D2-Pmp22Tr-J/J) and C57BL/6 wild type were obtained from Jackson Laboratory (Bar Harbor, ME). Nine to 12-week-old TrJ mice were injected in the left gastrocnemius muscle with either PBS (n=6) or $3\times10^{10}$ vg of self complimentary (sc)AAV1.tMCK.NT-3 vector (n=6). Another cohort of TrJ mice were injected with $1\times10^{11}$ vg of single stranded AAV1.CMV.NT-3 to induce high NT-3 expression levels for comparison (n=6). WT mice received either PBS (n=6) or $3\times10^{10}$ vg of scAAV1.tMCK.NT-3 vector (n=4). Groups of mice were euthanized and their muscles harvested at 16 weeks post gene injection and processed for cryostat sectioning. Succinic dehydrogenase (SDH) enzyme histochemistry was used to assess metabolic fiber type differentiation using standard protocol established inhouse. Muscle fiber type specific diameter measurements were obtained from 12 [tin thick-SDH stained cross sections. Three images, each representing three distinct zones of the gastrocnemius muscle (a deep zone predominantly composed of STO, intermediate zone showing a checkerboard appearance of STO and FTO or FTG and the superficial zone predominantly composed of FTG fibers) along the midline axis (per section per zone per animal) was photographed at X20 magnification using an Olympus BX41 microscope and SPOT camera. This approach was chosen to capture the alterations in the oxidative state of fibers in each zone in response to metabolic changes with treatment. Diameters of dark (STO), intermediate (FTO) and light FTG) fibers were determined by measuring the shortest distance across the muscle fiber using Zeiss Axiovision AXIOVISION LE4 software and expressed as percent of total. The mean fiber diameter (mean±SEM) was derived from combining all 3 fiber types in each cohort. An average of 1250 fibers (between 960 to 1486) were measured per group.

AAV.NT-3 vector production and potency: Design of self-complementary AAV viral vectors with serotype 1 containing NT-3 under tMCK or CMV promoter was described previously which were produced in the Viral Vector Core at Nationwide Children's Hospital, Columbus. Sahenk et al., Mol Ther, 22(3):511-521 (2014). Aliquoted viruses were kept in −80° C. until use. Blood samples were collected from treated and non-treated mice by eye bleeding under anesthesia at 6 and 16 weeks post injection and serum was assayed for NT-3 levels using a capture ELISA.

C2C12 myoblast culture and myotube formation: C2C12 myoblasts were cultured in growth medium (GM) consisting DMEM Medium (Gibco-Invitrogen, #10569010, Carlsbad, CA) supplemented with 10% FBS (Fisher Scientific, #26-140-079 Carlsbad, CA), and 1% Penicillin/streptomycin solution (Gibco-Invitrogen, #15640055 Carlsbad, CA) at 37° C. and 5% CO2 in a humidified chamber. Myotube formation was induced on confluent cultured cells by switching the GM to differentiation medium [DMEM (Gibco-Invitrogen, #11965092, Carlsbad, CA) supplemented with 5% Horse serum (Gibco-Invitrogen, #26050088, Carlsbad, CA) and 1% Penicillin/streptomycin solution (Invitrogen, #15640055 Carlsbad, CA)]. All subsequent assays with myotubes including QPCR, Western Blot and ELISA were started 3 days after induction of myotube formation. Both myoblast and myotubes were exposed to recombinant human NT-3 (Pepprotech, Rocky Hill, NJ) at 100 ng/ml concentration in 6 well plates. Culture media was collected for detection of glucose consumption and lactate formation by using glucose and lactate assay kits (Eton Bioscience, San Diego, CA) according to the manufacturer's instructions.

QPCR experiments: Total RNA was isolated from the gastrocnemius muscles of NT-3 treated and non-treated control mice at the endpoint. Total RNAs was isolated from myoblast and myotubes before and 48 hours after NT-3 treatments. A mirVana RNA isolation kit (Life Technologies, #AM1560, TX, USA) was used and subsequently synthesized the cDNA by using Trascriptor First Strand cDNA synthesis kit (Roche, #04379012001 Roche, USA) following manufacturer's instructions. Other qPCR experiments were performed by using iTaq™ universal SYBR® Green supermix (Biorad, #1725122, Hercules, CA, USA). Primer sequences for, PGC 1α (Cunningham et al., Nature, 450 (7170):736-740 (2007)) and GAPDH (Toscano et al., Mol Ther, 18(5):1035-1045 (2010)) (housekeeping gene) were found in the literature. Other primers sequences was found from Primer Band. Wang et al., Nucleic acids research, 40(Database issue):D1144-1149 (2012). All qPCR experiments were done by using ABI 7500 Real time PCR machine and the results were analyzed using Data Assist Software (ABI).

Protein extraction and western blot experiments: Frozen gastrocnemius muscle blocks were cut in 20 μin thickness, put into small 2 ml plastic tubes (15-20 section per block) and homogenized in lysis buffer [RI PA lysis buffer (Thermo Fisher, #89900, USA) with lx Halt protease inhibitor (Thermo Fisher, #78429, USA) and lx phosphatase inhibitor (Sigma, #P0044, USA)] using an automatic pellet mixer and disposable pestles with 20 seconds periods for three times. For in vitro signal transductions assays, myoblast and myotubes were collected in small 2 ml tubes after 30 minutes of incubation with NT-3 (100 ng/ml) and lysed in the same way as mentioned above. The lysates were centrifuged at 13,000 rpm for 10 minutes at 4° C. and the supernatants were carefully collected. Protein concentration was measured by using BCA Protein Assay Kit (Thermo Fisher, #23252, Waltham, MA, USA). Protein samples (10-40 itg) were run in 4-12% Bolt® Bis-Tris Plus precast 10 or 15-well polyacrylamide gels (Thermo Fisher, #NW04120BOX) and transferred to PDVF membranes (GE Healthcare, #10600021, Pittsburgh, USA). Membranes were blocked for 2 hours at room temperature with 5% bovine serum albumin (BSA, Bedford, MA, USA) in TBS buffer with 0.05% TWEEN-20 (TBS-T, Amresco, OH, USA) and incubated with the appropriate primary antibody in TBS-T buffer with 5% BSA overnight in cold room at 4° C. The primary antibodies used in this study were as follows: anti-phospho S6 protein Ser235/236 (#4858), anti-S6 protein (#2217), anti-Phospho Akt Ser473 (#4060), anti-Akt (#9272), anti-phospho 4E-BP1 thr37/46 (#2855), anti-4E-BP1 (#9644), anti-GAPDH (Santa cruz, #sc365062). After washing 5 minutes for 5 times on an orbital shaker with TBS-T, the membranes were incubated with secondary antibodies [HRP conjugated anti-rabbit (#HAF008), HRP conjugated anti mouse (HAF007)] from R&D Systems, Minneapolis, MN, USA] in 5% dry milk in TBS-T buffer for 1 hour. The membranes were washed again with TBS-T in the same way as above and then incubated with ECL Prime western detection reagent (Amersham, #RPN2232 NJ, USA) for 1-3 minutes followed by exposing to X-ray films (Denville, #E3018, MA, USA) using multiple exposure times. Protein bands on the film were pictured using a camera (Sony A600, Japan) and the band intensities were quantified using (Quantity-One software, BioRad, v.4.6.9). The relative content of analyzed proteins in each sample was determined by normalizing band intensities to the content of GAPDH in the same sample. The membranes were stained with 0.1% Coomassie Brilliant Blue R stain (Thermo Fisher, USA), rinsed and photographed to confirm equal protein loading in each lane.

Statistics: For muscle fiber size comparisons between treated and non-treated groups, statistical analysis were performed in Graph pad Prism 6 software, using one-way analysis of variance (Anova). Student t-test or one-way Anova was performed when applicable for other statistical analyses. Significance level was set at $P<0.05$. Results were given as mean±SEM in all experiments.

Results

AAV1.NT-3-Induced Fiber Type Remodeling in TrJ Muscle

Previously in the TrJ muscles, a switch from fast to slow-type fibers was observed as part of neuropathic phenotype. Nicks et al., J Neuropathol Exp Neurol, 72(10):942-954 (2013). In this study, SDH stain was used to assess the metabolic fiber type differentiation in the gastrocnemius muscle of TrJ and age-matched WT by sampling from deep, intermediate and the superficial zones of the muscle as described. At 16 weeks post-gene injection, there was a notable decrease in the STO fibers along with fiber size increase, particularly of the FTO and FTG types compared to the untreated (PBS) group, which showed neurogenic changes, small angular fibers and type groupings (FIGS. 1A and B). Quantitative studies showed that in the TrJ-PBS muscles both the number per unit area as well as the percentage of STO fibers were significantly higher than the WT muscle, in agreement with the previous studies. In the treatment groups, AAV1.NT-3 at $1 \times 10^{11}$ vg dose with both promoters resulting either low (tMCK) or high (CMV) NT-3 expression (FIG. 4) showed fiber type switching from STO to FTO/FTG fibers. Mean density or percent of STO (derived from n=3-5 mice in each group) in both treatment groups was not significantly different from the WT muscle indicating a change towards normalization of fiber type distribution with NT-3 (FIG. 1C). Moreover, AAV1.NT-3 treated WT muscle did not show a significant change in fiber type distribution profile.

NT-3 treatment in TrJ mice showed a differential effect on muscle fiber size increase (Table 2). When NT-3 was expressed under the control of tMCK promoter a significant diameter increase was observed, only in the FTG fibers. In the second treatment cohort, where high NT-3 expression was obtained with the CMV promoter, there was significant diameter increase in all fiber types. Interestingly, this dose dependent NT-3 effect was only seen in the neurogenic TrJ muscle; no significant in diameter change was seen in any of the fiber types in the WT muscle with NT-3 gene therapy at the same time point, 16 weeks post gene injection.

Table 2 shows that the fiber size increase in the neurogenic TrJ muscle following NT-3 gene therapy is more prominent for fast twitch fibers.

Figure 2:
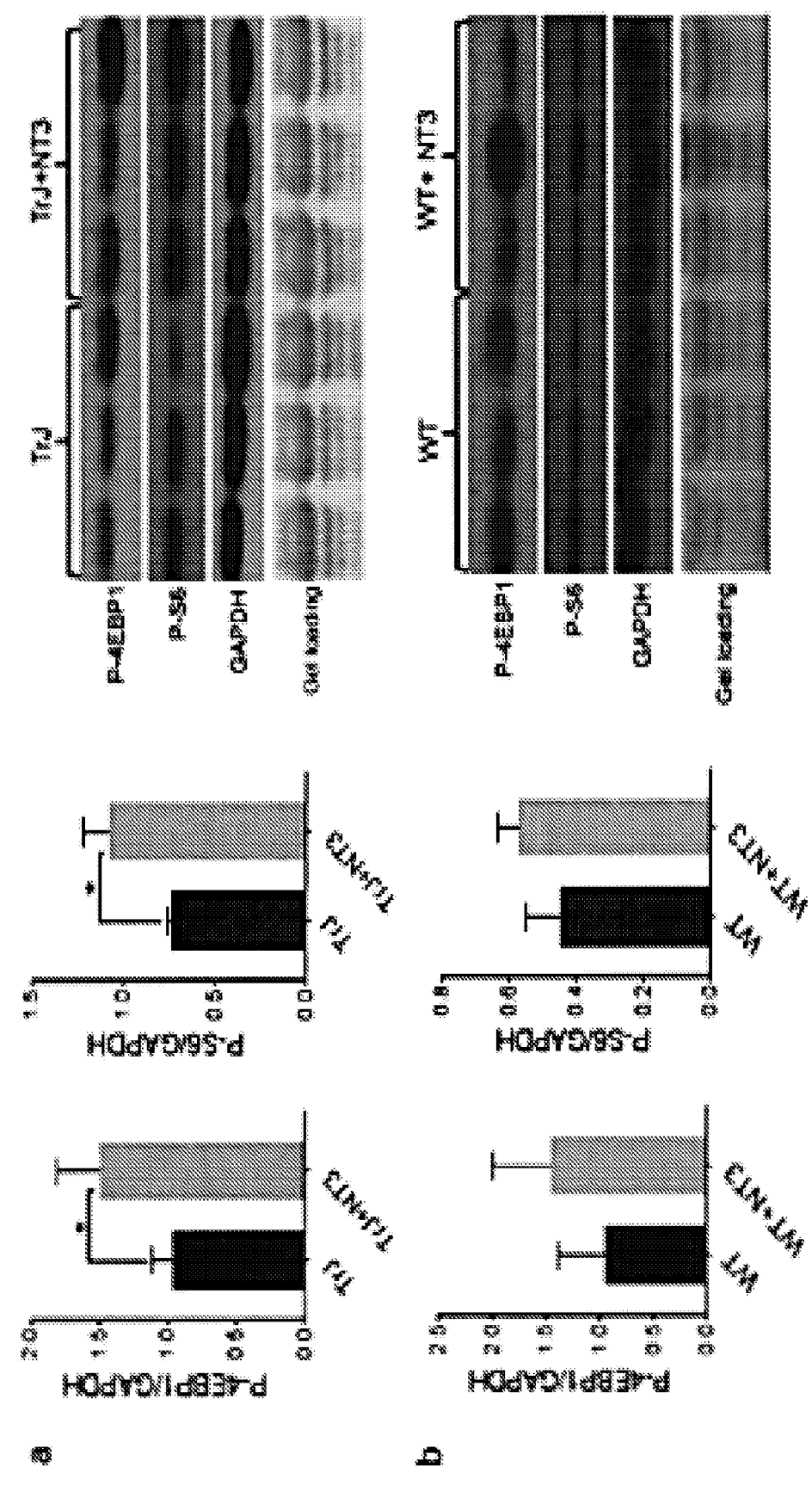
FIGS. 2A-C provide graphs and images showing the effect of AAV 1 .NT3 treatment on mTOR signaling and metabolic markers. Representative western blot images and analysis of mTOR targets, Phospho (P)-4EBP1 (Thr37/46), and P-S6 (Ser235/236) in TrJ (FIG. 2A) and wild type (WT) (FIG. 2B) gastrocnemius muscles at 16 weeks post injection. The graphs show expression levels of the phosphorylated form of proteins normalized to GAPDH. Coomassie Blue stained membranes represent equal gel loading. Error bars are ±SEM; n=5-6 in each group, *P<0.05, unpaired t test.
Figure 2:
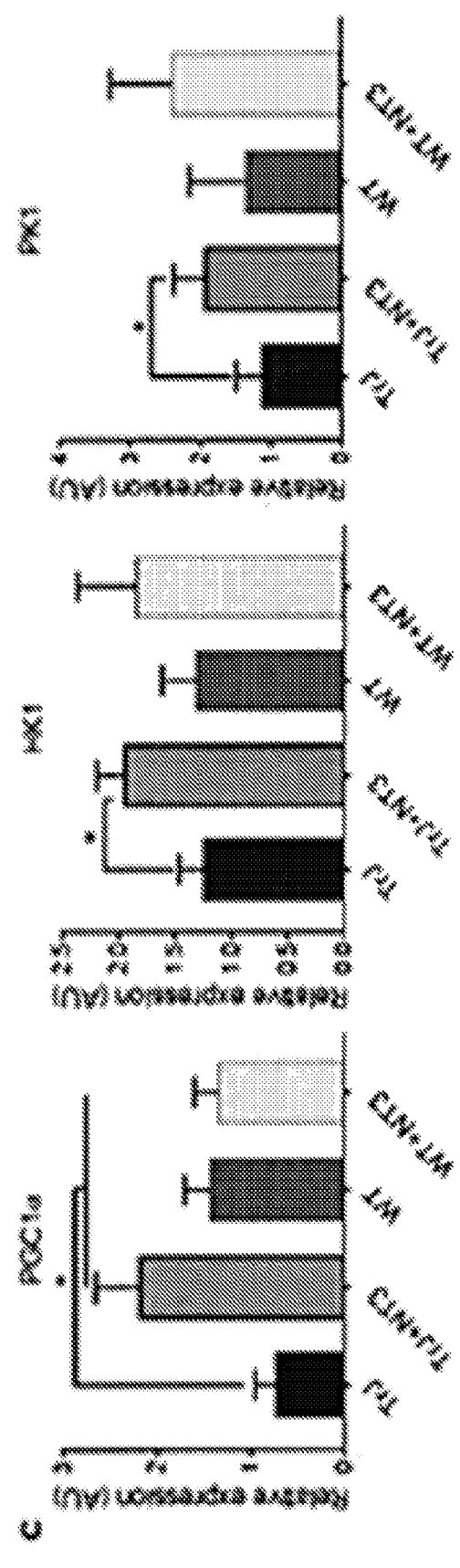

Mean Fiber Diameter sumption and production[17]. Accordingly, the master regulator of mitochondrial biogenesis, PGC 1α was upregulated in the NT-3 treated TrJ muscle indicating that NT-3 is capable of reversing the defective expression levels of PGC 1α seen in the neurogenic muscle (FIG. 2C). In concert with the lack of mTORC1 activation, no change in PGC 1α expression levels was seen in the WT muscle with NT-3 treatment (FIG. 2C). The fiber size increase in TrJ muscle with NT-3 gene therapy mainly occurred in FTO and FTG fibers, which have greater glycolytic activity than slow fibers [18]. In agreement, it was also found that the expression of the rate limiting enzymes of glycolysis, HK1 and PK1 in the treated TrJ muscle was upregulated suggesting increased glycolytic flux. These changes were not significant in the AAV.NT-3 treated WT muscle.

NT-3 Activates Akt/mTORC1 Pathway through TrkC Receptors in C2C12 Myotubes

The in vivo studies described herein showed that AAV1.NT-3 treatment-induced fiber size increase and fiber type remodeling in the TrJ muscle is associated with mTORC1 activation. However, the question whether this change is solely the consequence of reinnervation, or NT-3, independent of nerve regeneration may directly alter muscle protein synthesis and cell metabolism needs to be answered. As the next step, the direct effects of NT-3 on mTOR pathway in an in vitro system was investigated, free of nerve influence by exposing C2C12 myoblast and myotubes to recombinant NT-3. The results indicated that NT-3 can induce Akt/mTOR pathway activation in myotubes (FIG. 3A) but not in myoblasts. Treatment of myotubes with 100 ng of recombinant NT-3 for 30 minutes resulted in significantly higher phosphorylation of Akt, 4EBP1 and S6P compared to the control group (FIG. 3A). In another set of experiment, NT-3 was found to be significantly enhanced the expression the mitochondrial biogenesis marker PGC 1α and the marker of glycolysis, PK1 in myotubes upon 48

| | WT (n = 3) | | WT + NT3 (n = 4) | | TrJ-PBS (n = 3) | | TrJ-tMCK (n = 4) | | TrJ-CMV (n = 5) | |
|---|---|---|---|---|---|---|---|---|---|---|
| | Number | Diameter (μm) | Number | Diameter (μm) | Number | Diameter (μm) | Number | Diameter (μm) | Number | Diameter (μm) |
| STO | 315 | 31.4 ± 0.35 | 413 | 31.25 ± 0.32 | 605 | 28.52 ± 0.29* | 524 | 29.41 ± 0.23 | 436 | 33.46 ± 0.4* |
| FTO | 262 | 38.09 ± 0.5 | 378 | 37.35 ± 0.39 | 273 | 34.32 ± 0.65* | 457 | 35.33 ± 0.47 | 374 | 39.15 ± 0.6* |
| FTG | 383 | 46.02 ± 0.45 | 525 | 45.76 ± 0.4 | 194 | 39.79 ± 0.74'* | 505 | 43.77 ± 0.41* | 458 | 44.35 ± 0.52* |
| All Fiber | 960 | 39.06 ± 0.32 | 1316 | 38.79 ± 0.28 | 1072 | 32.04 ± 0.3* | 1486 | 36.11 ± 0.27* | 1268 | 39.07 ± 0.32* |

*p < 0.001

AAV-NT-3 Improved mTOR Signaling and Metabolic Markers in TrJ Muscle

Above shown histological findings in the TrJ muscle in response to AAV1.NT-3 treatment prompted the investigation of whether mTORC1 activation played a role in the NT-3-induced radial growth of muscle fibers. The activity of mTORC1 was assessed by phosphorylation levels of its downstream substrates, 4EBP-1 and ribosomal S6P in muscle samples from groups. In AAV1.NT-3 treated TrJ muscle, levels of phosphorylated 4EBP-1 and S6P significantly increased compared to untreated counterparts obtained from TrJ-PBS controls (FIG. 2A). In contrast, it was found that NT-3 treatment did not affect the phosphorylation levels of 4EBP-1 and S6P in the WT muscle significantly (FIG. 2B).

Via 4E-BPs, mTORC1 regulates synthesis of nucleus-encoded mitochondrial proteins, controls mitochondrial activity and biogenesis, therefore coordinates energy conhours incubation (FIG. 3B). Accordingly, analysis of supernatants at this time point revealed increased glucose consumption and lactate production in NT-3 treated myotubes compared to control (FIG. 3C). Under the conditions these experiments were carried out, no NT-3 effect on the HK1 expression levels was observed.

The expression of p75NTR and TrkC receptors, and myogenin which is the marker for the entry of myoblasts into the differentiation pathway in myoblast and myotube cultures, were analyzed. NT-3 exerts its biological effect through its preferred receptor TrkC or binding to low affinity neurotrophin receptor p75NTR. Schecterson L C, Bothwell M, Neuron, 9(3):449-463 (1992). p75NTR is expressed in C2C12 myoblasts and downregulated during myogenic differentiation. Seidl et al., Journal of cellular physiology, 176(1):10-21 (1998). It has been shown that neurotrophic factor, NGF affects myogenic differentiation and cell growth via p75NTR and downregulation of p75NTR is thought to be essential for myogenic differentiation. Similar to NGF effects, it was found that NT-3 also enhanced the expression of myogenin in the myotubes, and as expected, this was associated with strikingly higher expression of p75NTR in myoblasts compared to the myotubes, whereas TrkC expression levels were not different in both groups (FIG. 3D). NT-3 did not exert a differential effect on the expression levels of these receptors in myoblasts or in myotubes.

Discussion

Presented herein is evidence that NT-3 can have direct effect on neurogenic muscle metabolism resulting in fiber size increase and fiber type remodeling toward normalization via activation of mTORC1. The fiber size increase was most prominent for type II fibers, particularly for the FTO subtype. Moreover, it is shown that NT-3 can induce Akt/mTOR pathway activation in myotubes but not in myoblasts directly, as an important contributor to its in vivo effect in neurogenic muscle. Interestingly, NT-3 gene therapy in WT muscle at the same dose did not affect these properties, although the NT-3 effect on the denervated WT muscle using the gene therapy paradigm was not studied. A differential effect of NT-3 on type II muscle fiber sub type was shown previously in rat gastrocnemius muscle 8 months after nerve repair with or without local delivery of NT-3 to the nerve crush site and found both proportion and size of type IIb fibers returned to normal. Sterne et al., J Cell Biol, 139(3): 709-715 (1997). This effect however was interpreted as NT-3-enhanced axonal regeneration having a beneficial result on the motor target organ as well as the possibility of NT-3 may be specifically influencing a subset of motoneurons that determine type IIb muscle fiber phenotype. It can be argued that findings from our in vivo studies may represent a combinatorial effect of NT-3 on both nerve and muscle. Our in vitro data however emphasize the evidence that NT-3 has direct effect on muscle metabolism via activation of Akt/mTORC1 and that this direct effect is likely to be important in the neurogenic muscle leading to preferential size increase in FTG, i.e. type Erb fibers.

In a conditional transgenic mouse expressing a constitutively active form of Akt lead to muscle hypertrophy due to the growth of type III) muscle fibers. Izumiya et al., Cell metabolism, 7(2):159-172 (2008). This was associated with upregulation of transcripts involved in glycolysis, increased glucose consumption and lactate production, which were linked to lower insulin levels, increased glucagon levels in the blood and resistance to high fat diet induced obesity. Conversely, mTOR inactivation was associated with reduction of glycolytic enzymes, PK1 and HK1. Risson et al., J Cell Biol, 187(6):859-874 (2009). In our studies, AAV.NT-3 treatment in the TrJ muscle increased both the size of the FTG fibers and the expression of glycolytic enzymes PK-1 and HK-1. In addition, in vitro studies revealed that NT-3 increased glucose uptake and lactate formation in myotubes along with upregulation of PK-1. Although these results suggest that NT-3 might take part in controlling whole body metabolism by regulating fast/glycolytic fibers, further studies are needed to characterize its role in detail. In addition, AAV.NT-3 treatment was capable of reversing the defective expression levels of PGC 1α seen in the TrJ neurogenic muscle along with enhanced levels of activated 4E-BP1. It was previously suggested that in the skeletal muscle, mTOR regulates mitochondrial biogenesis and metabolism through 4E-BP1/PGC 1α. Tsai et al., J Clin Invest, 125(8):2952-2964 (2015). NT-3 might also be playing role promoting oxidative phosphorylation through activation of 4EBP1 and PGC 1α in the muscle.

NT-3, is found in high levels first in the central nervous system (CNS) during fetal development and is reduced in the adult brain, suggesting that it has a central role during early neuronal development [28, 29]. NT-3 is also important in the peripheral nerves, and has positive effects at multiple stages of neuromuscular development. In Xenopus nerve-muscle co-cultures muscle-derived NT-3 significantly enhances maturation of synaptic transmission at the neuromuscular junction [30-33]. Moreover, NT-3 increases the survival of a crucial element of the neuromuscular system, the SC [34]. NT-3, expressed in SCs, promotes nerve regeneration, and is an important component of the autocrine survival loop, ensuring SC survival and differentiation in adult nerves[35-39]. In the studies in the CMT1A mouse models several important biological effects of NT-3 were observed, (i) an increase in the SC numbers, (ii) an increase in the number of myelinated fibers, and (iii) a normalization of axonal neurofilament cytoskeleton [5, 40]. Another NT-3 effect of particular interest here, is an increase in myelin thickness, which was perceived as the morphologic evidence that NT-3 might influence myelin protein production.

Earlier studies have shown considerable evidence that mTORC1 has a role in regulating myelination in the CNS. Transgenic overexpression of a constitutively active Akt kinase is sufficient to enhance myelin membrane growth in the CNS via mTOR signaling [41, 42] and IGF-1-stimulated protein synthesis in oligodendrocyle progenitors requires PI3KJAkt and MER/ERK pathways [43]. The capacity of NT-3 targeting the translational machinery to stimulate myelin protein synthesis was first shown in oligodendrocyte primary cultures [44]. NT-3 was found to upregulate 4EBP1 phosphorylation in the oligodendrocytes through PI3K/mTOR pathway. Using gene inactivation approach, ablating mTOR function specifically in SCs influenced their ability to myelinate normally [45]. In fact, in mutants the myelin sheath was found thin, internodal length was short and the radial growth of axons was impaired. Along with, the mTOR downstream targets, S6 and 4E-BP1 were less phosphorylated [45].

In light of these previous studies, it was possible that NT-3 effect on the muscle fiber diameter increase is through the same mechanism, a direct effect via activation of mTORC1. It is important to note that NT-3 gene therapy in WT muscle at the same dose used in the TrJ did not induce a significant change in fiber type size or type distribution. These observations in WT muscle suggest NT-3 effect is not directed to well-differentiated or normal functioning cells, but rather is functional upon remodeled-cell metabolism that may result from a pathological process. One supporting evidence is that NT-3 does not alter functional recovery following crush injury in WT animals, resulting in only slightly more axons than control or NGF-treated animals [46]. Our toxicology studies assessing scAAV1.tMCK.NT-3 are in agreement with these observations showing no treatment-related toxicity or histopathological abnormalities of organ tissues in C57BL/6 or in TrJ mice, dosed at $1\times10^{13}$ vg/kg, which is 10-fold higher than the highest dose proposed for human trials for the treatment of CMT1A.

Figure 5:
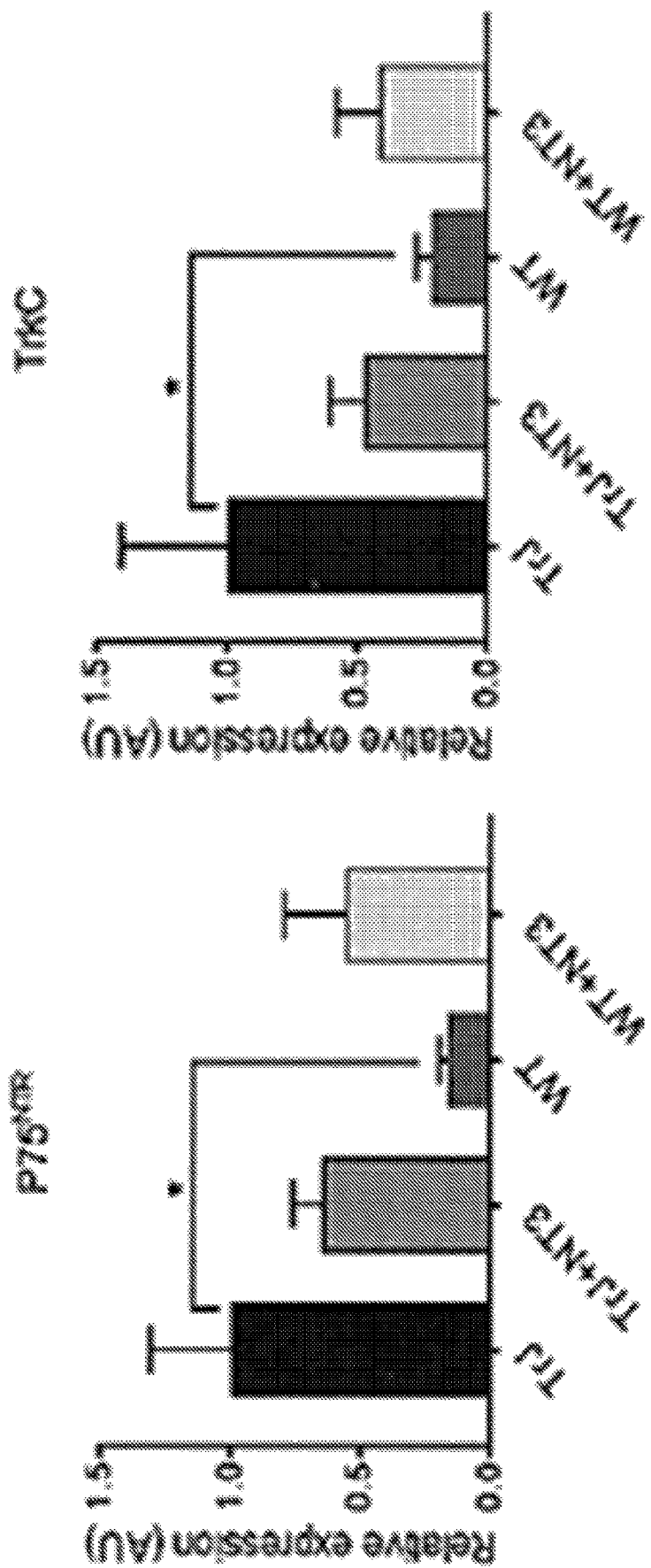
FIG. 5 shows the relative mRNA expression of P75$^{NTR}$ and TrkC in TrJ and WT gastrocnemius muscle. GAPDH was as housekeeping gene in the analyses. The results shown are mean±SEM from at least three independent experiment, *P<0.05, Student's t-test.
Figure 6:
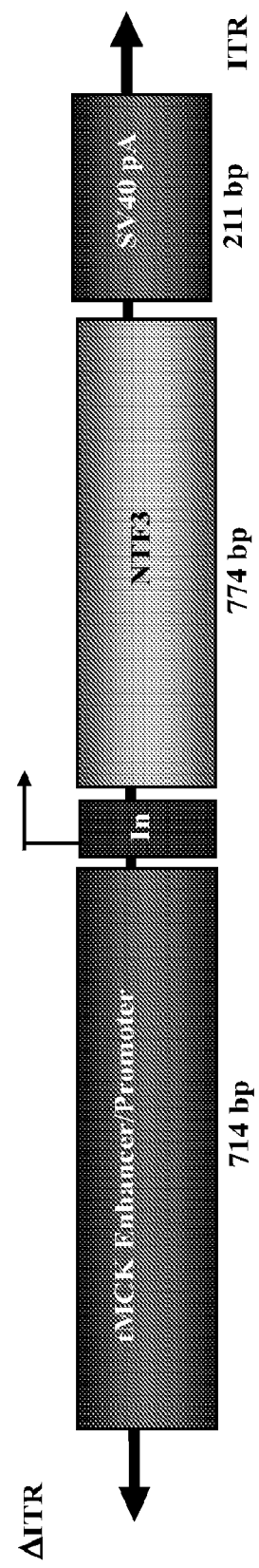
FIG. 6 provides a schematic of the construct AAV.tMC-K.NTF3 (SEQ ID NO: 11). The vector contains the muscle specific tMCK promoter (SEQ ID NO: 3), chimeric intron (SEQ ID NO: 5), consensus Kozak sequence (SEQ ID NO: 6), the NTF3 cDNA (SEQ ID No: 1), and a polyadenylation signal (SEQ ID NO: 7).

During muscle development, p75NTR is expressed transiently on myoblasts that will form myotubes/muscle fibers or differentiate into satellite cells [23]. The temporal expression pattern of the receptor indicates that p75NTR mediates survival of myoblasts prior to differentiation and that the activity of this receptor during myogenesis is important for developing muscle [23]. Similar to the NGF effect [21], it was found that NT-3 enhanced the expression of myogenin in the myotubes, and as expected, this was associated with strikingly higher expression of p75NTR in myoblasts, which significantly down regulated in the myotubes. p75NTR and TrkC expression in TrJ and WT muscle samples were examined and found significantly high expression levels of both in the neurogenic TrJ muscle compared to WT and the levels came down in response to NT-3 (FIG. 5). Although interesting, this observation does not allow any conclusion as to which cell types express these receptors, or whether they are expressed in all or only a subtype of muscle fibers, in satellite cells or SCs. The available data on the expression of NT-3 and other neurotrophins and their receptors in human muscle disease are limited. However, recent studies so far combining histological investigations of muscle biopsies with molecular and cellular analyses of primary muscle precursor cells have shown that p75NTR is expressed by most satellite cells in vivo and is a marker for regenerating fibers in inflamed and dystrophic muscle [47, 48]. Our findings in neurogenic muscle are of particular interest and more comprehensive studies on mechanisms in different disease processes are required.

As a conserved Ser/Thr kinase, mTOR is a central regulator of cell growth by integrating signals from nutrients, growth factors, energy status, and environmental stress. The essential role of mTOR in cell biology and pathobiology, particularly in muscle with remarkable metabolic and morphological adaptive capabilities is now of great interest. mTOR associates with raptor to form mTORC1 and muscle-specific inactivation of raptor was shown to lead to muscle atrophy, impaired oxidative capacity, and increased glycogen stores, resulting in dystrophic features that were most prominent in oxidative muscles [49]. Loss of mTOR activity on the other hand exacerbated the myopathic features in both slow oxidative and fast glycolytic muscles and display metabolic changes similar to those observed in muscles lacking raptor, including impaired oxidative metabolism, altered mitochondrial regulation, and glycogen accumulation [26]. In studies using a paradigm of cardiotoxin-induced cycles of muscle necrosis/regeneration, the inventors recently showed impaired regeneration in a mouse model of limb girdle muscular dystrophy type 2A, and showed that calpain-3 null muscle is associated with perturbations in mTORC1 signaling and defective mitochondrial biogenesis (in review). Taken together, the findings described herein have many implications for the potential use of NT-3, not only for treatment of neuropathies with benefits to both nerve and muscle, but also for muscle wasting conditions including aging, cancer cachexia or type II muscle fiber atrophy as well as genetic or acquired autoimmune primary muscle disorders associated with impaired radial growth phase of regeneration [50-52]. Understanding the role of perturbations in mTOR signaling in these disorders should allow development of novel combinatorial therapeutic strategies in which NT-3 may have an important role.

Example 2

NT-3 Delivery Using the scAAV1.tMCK.NFT3 Vector

Figure 3:
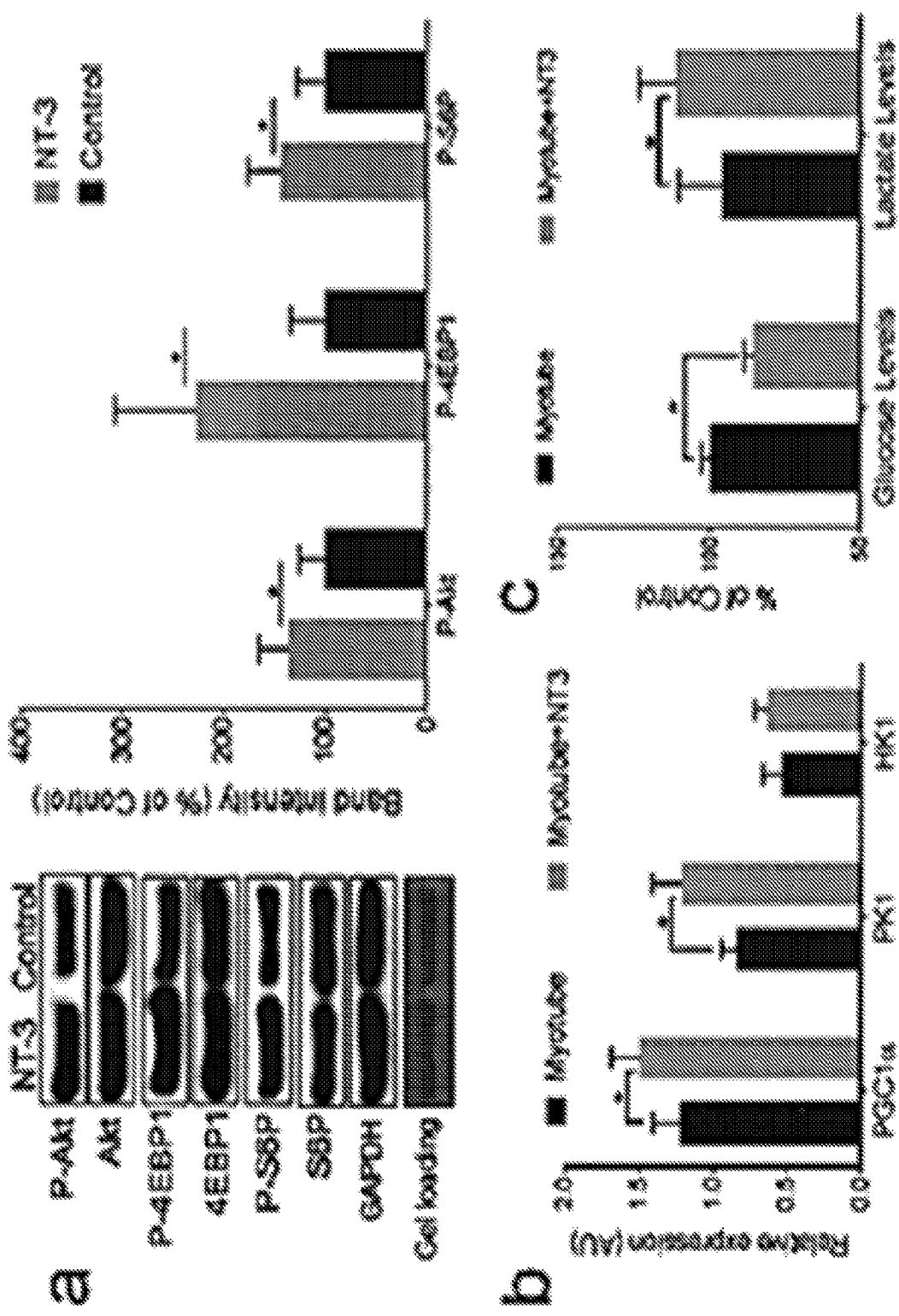
FIGS. 3A-D provide graphs and images showing the direct effect of NT-3 on myotubes.
Figure 3:
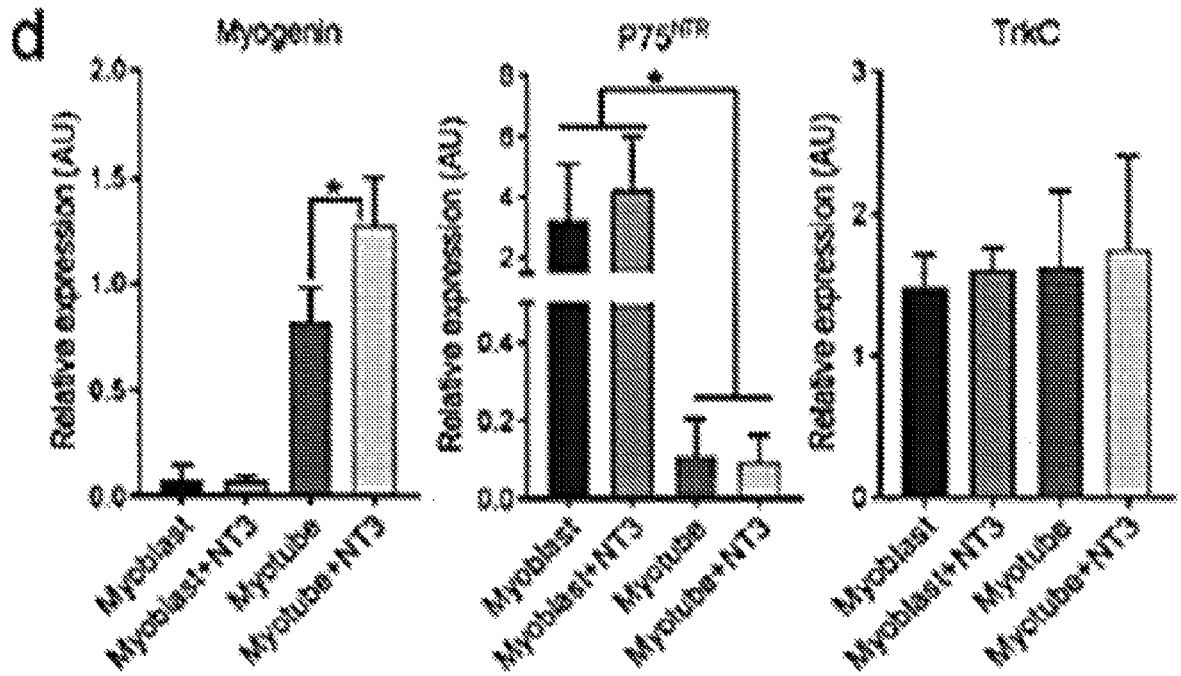

The composition administered is a non-replicating recombinant adeno-associated virus termed scAAV1.tMCK.NTF3, which is shown in FIG. 3. The vector contains the human NT-3 gene under the control of a tMCK muscle-specific promoter. In vivo biopotency will be tested following the intramuscular injection of the vector ($1\times10^{11}$ vg) into gastrocnemius muscles of C57B16 mice followed by quantification of circulating NT-3 in the serum by ELISA at 4 to 6 weeks after gene injection.

Firstly it was demonstrated that ssAAV1.CMV.NTF3 delivered to gastrocnemius muscle produced prolonged and therapeutic NT-3 blood levels sufficient to provide functional, electrophysiological and histopathological improvement in TrJ nerves. It was then investigated if it was possible to produce the required vector dose and achieve same level of expression by packaging the expression cassette by scAAV1. A dose-response study was performed on C57BL/6 mice comparing serum NT-3 ELISA data following intramuscular injection of scAAV1.tMCK.NTF3 and scAAV1.CMV.NTF3 at 3 doses ($3\times10^9$ vg, $1\times10^{10}$ vg and $3\times10^{10}$ vg). Adminstraton of sc.rAAV1.CMV.NTF3 vector at $1\times10^{11}$ vg produced significantly higher NT-3 levels than the single-stranded vector at the same dose consistent with greater potency using self-complementary vectors. At a half-log less dose ($3\times10^{10}$ vg), both CMV and tMCK vectors produced comparable NT-3 serum levels to those obtained from mice that received ss.AAV1.CMV.NTF3 at $1\times10^{11}$ vg dose, which produced a biological response. The NT-3 levels (mean±SEM) from TrJ mice at 24 weeks post injection. There is significant difference in NT-3 levels among all 7 groups, p value<0.0001. A significant difference in NT-3 levels was observed for highest and intermediate doses of vectors for both promoters and control. However, analysis failed to find significant difference for lower doses for both vectors. Kruskal-Wallis test is used to compare serum NT-3 among all groups (PBS, CMV 3E+09/1E+10/3E+10 and tMCK 3E+09/1E+10/3E+10). Mann-Whitney U test is used to compare NT-3 between each group and PBS (control) group, and Bonferroni correction is used to adjust for multiple comparisons. See Sahenk et al., Mol. Ther. 22(3): 511-521, 2014, which is incorporated by reference herein in its entirety.

Muscle diameter increases at 40 weeks posttreatment: The effects of NT-3 gene therapy was assessed in TrJ mice upon muscle fiber size at 40 weeks postinjection in a subset of animals injected with ssAAV1.CMV.NTF3 ($1\times10^{11}$ vg) compared to PBS. Neurogenic changes characterized by atrophic angular fibers and group atrophy were evident in the muscles from untreated mice while evidence for reinnervation as fiber type groupings and an overall fiber size increase were recognizable as treatment effect. Muscle fiber size histograms generated from contralateral anterior and posterior compartment muscles of the left lower limb (tibialis anterior and gastrocnemius) showed an increase in fiber diameter.

Additional studies in our laboratory have shown that NT-3 stimulates Akt/mTOR pathway in SCs cells giving rise to improved myelination and radial growth of axons in the nerve and NT-3 also has a direct stimulatory effect on myotubes through Trk-C receptors indicating its role in fiber diameter increase in muscles of TrJ mice. FIG. 3A shows NT-3 increased the phosphorylation of Akt (P-Akt) and mTOR targets, 4EBP-1 (P-4EBP1) and PS6K (P-S6K) in SC and myotube cultures. These studies provide evidence justifying our choice of anterior and posterior muscles of the lower leg for vector delivery in this clinical trial.

Studies with Self-Complementary (sc) AAV1 and the Use of a Muscle Specific Truncated Creatine Kinase (tMCK) Promoter scAAV permits lower dosing that adds up to enhanced safety and dosing levels that will meet production standards. The use of tMCK promoter is a valued objective again offering greater safety by avoiding off target effects. In the following set of experiments the efficacy of scAAV1.NTF3 under control of the CMV promoter was compared to the muscle specific tMCK promoter both given at three doses, within a half-log range ($3\times10^9$ vg, $1\times10^{10}$ vg and $3\times10^{10}$ vg). The efficacy AAV1.NTF3 gene transfer in TrJ mice peripheral nerves were assessed by electrophysiological (Table 3) and morphological studies 24 weeks post gene transfer. The evidence of transgene expression was assessed by measuring serum NT-3 levels using ELISA.

TABLE 3

CMAP and Conduction Velocity in the TrJ Sciatic Nerve

| Treatment Group (number) | | Latency (ms) | Duration (ms) | CMAP (mV) | Area (mVms) | Conduction Velocity (m/s) |
|---|---|---|---|---|---|---|
| PBS | 29 | 2.36 ± 0.08 | 7.00 ± 0.42 | 0.42 ± 0.03* | 0.70 ± 0.09 | 8.24 ± 0.43 |
| AAV1.NTF3.CMV-HD | 23 | 2.43 ± 0.10 | 6.58 ± 0.50 | 0.57 ± 0.04* | 0.84 ± 0.09 | 10.30 ± 0.65 |
| AAV1.NTF3.tMCK-HD | 27 | 2.52 ± 0.07 | 5.64 ± 0.49 | 0.54 ± 0.03** | 0.64 ± 0.04 | 8.90 ± 0.56 |
| AAV1.NTF3.CMV-ID | 21 | 2.08 ± 0.09 | 5.20 ± 0.38 | 0.46 ± 0.04 | 0.61 ± 0.07 | 9.00 ± 0.63 |
| AAV1.NTF3.tMCK-ID | 26 | 2.20 ± 0.08 | 5.85 ± 0.42 | 0.45 ± 0.03 | 0.61 ± 0.06 | 9.01 ± 0.40 |
| AAV1.NTF3.CMV-LD | 22 | 2.23 ± 0.10 | 6.38 ± 0.53 | 0.48 ± 0.04 | 0.68 ± 0.07 | 8.95 ± 0.74 |
| AAV1.NTF3.tMCK-LD | 23 | 2.18 ± 0.06 | 7.29 ± 0.60 | 0.43 ± 0.03 | 0.80 ± 0.08 | 8.40 ± 0.59 |

*p = 0.0017;
**p = 0.0051;
Values are Mean ± SEM;
HD = High Dose;
ID = Intermediate Dose;
LD = Low Dose The examiner during electrodiagnostic studies was blinded to the treatment groups. There is no statistical difference between AAV1.NTF3.CMV (high dose, HD) and AAV1.NTF3.tMCK (high dose, HD) on CMAP and it was preferred to use the muscle specific tMCK promoter. This is further supported by the NT-3 levels in ELISA Assay where a significant difference in NT-3 levels was observed for highest and intermediate doses of vectors for both promoters and control.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Example 3

Construction of NT-3 Expressing AAV Construct

Design of self-complementary AAV viral vectors with serotype 1 containing NT-3 cDNA under tMCK or CMV promoter was described previously in Sahenk et al., Mol Ther, 22(3):511-521 (2014), which is incorporated by reference herein in its entirety. Aliquoted viruses were kept in −80° C. until use. Blood samples were collected from treated and non-treated mice by eye bleeding under anesthesia at 6 and 16 weeks post injection and serum was assayed for NT-3 levels using a capture ELISA. The construct is referred to herein as scAAV1.tMCK.NTF3.

A tMCK promoter/enhancer sequence was used to drive muscle-specific gene expression and is composed of the muscle creatine kinase promoter with an added enhancer element (enh358MCK, 584-bp) fused to it. A triple tandem of the MCK enhancer (206-bp) was ligated to the 87-bp basal promoter in the tMCK promoter/enhancer.

Figure 7:
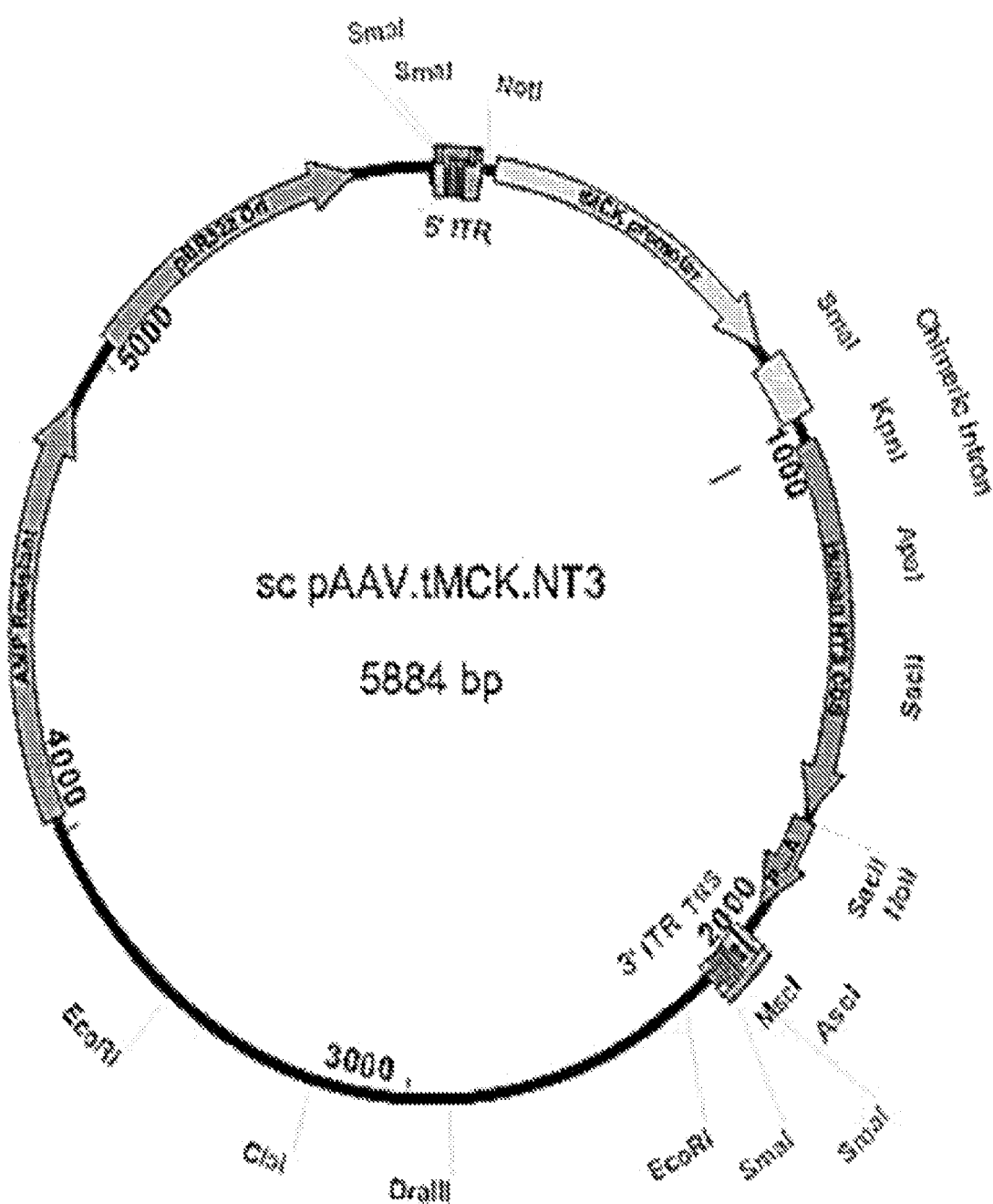
FIG. 7 provides a restriction map and ORF Analysis pAAV.tMCK.NTF3.

The scAAV1.tMCK.NTF3 drug product was produced by 3 plasmid DNA transfection of human HEK293 Master Cell Bank cells with: (i) the pAAV.tMCK.NTF3-vector plasmid (see FIG. 7), (ii) an AAV1 helper plasmid termed R88/C1 containing the AAV rep2 and Cap1 wild-type genes and (iii) the helper adenovirus plasmid A schematic representation of the plasmid with molecular features and open reading frames is shown in 7. The AAV vector genome derived from pAAV.tMCK.NTF3 plasmid is a self-complementary DNA genome containing the human NTF3 cDNA expression cassette flanked by AAV2 inverted terminal repeat sequences (ITR). It is this sequence that is encapsulated into AAV1 virions. Plasmid pAAV.tMCK.NTF3 was constructed by inserting the tMCK expression cassette driving a NTF3 gene sequence into the AAV cloning vector psub201. The human NTF3 gene is expressed from the mouse triple tandem MCK promoter which is a modification of the previously described CK6 promoter and contains a triple E box sequence. An SV40 polyadenylation signal is used for efficient transcription termination. The cassette also contains a chimeric intron for increased gene expression and is composed of the 5' donor site from the first intron of the human β-globin gene and the branchpoint and 3' splice acceptor site from the intron that is between the leader and the body of an immunoglobulin gene heavy chain variable region. The NTF3 expression cassette has a consensus Kozak immediately in front of the ATG start and 200 bp SV40 polyA signal for efficient mRNA termination. The NTF3 cDNA is included in its entirety (NCBI Reference Sequence: NM_001102654). The only viral sequences included in this vector are the inverted terminal repeats of AAV2, which are required for both viral DNA replication and packaging. The AAV ITRs are sequences that are nearly identical on both ends, but in opposite orientation. The "left" (mutated) ITR has the terminal resolution site deleted to allow hairpin formation of the genome. The identity of all DNA plasmid elements are confirmed by DNA plasmid sequencing on the plasmid source stock.

Shown in Table 4 are the base pair locations of relevant molecular features within in the AAV vector DNA plasmid of SEQ ID NO: 11.

TABLE 4

Molecular Features of plasmid sc pAAV.tMCK.NTF3

| TYPE | START | END | NAME | DESCRIPTION |
|---|---|---|---|---|
| REGION | 7 | 112 | 5' ITR | AAV2 inverted terminal repeat with terminal resolution site deleted |
| REGION | 147 | 860 | tMCK promoter/enhancer | Mouse muscle creatine kinase promoter/enhancer |
| REGION | 892 | 1024 | chimeric Intron | 5' donor site from human β-globin and the branchpoint and 3' splice acceptor site from IgG HC variable region. |
| GENE | 1077 | 1850 | Human NTF3 gene | Human NTF3 gene |
| REGION | 1860 | 2059 | SV40 pA | SV40 polyadenylation signal |
| REGION | 2121 | 2248 | 3' ITR | Wild-type AAV2 inverted terminal repeat |
| GENE | 4032 | 4892 | AmpP<sup>r</sup> | AmpP<sup>r</sup>P resistance gene |
| REGION | 5040 | 5707 | ori | Plasmid origin of replication |

Example 4

Phase I Intramuscular Study

For the initial phase I intramuscular (IM) safety study, sustained NT-3 transgene expression is the proposed outcome measure in this first phase is important for several reasons. The true assessment of toxicity depends on demonstrating gene expression. If muscle is not transduced, the tests of toxicity (adverse effects) will be more difficult to interpret (failure of transduction versus loss of gene expression). The study offers the opportunity to establish methods for unequivocally recognizing transgene expression and differentiating it from endogenous gene expression.

This clinical trial is an open-label, one-time injection ascending dose study in which scAAV1.tMCK.NTF3 is administered by intramuscular injection into gastrocnemius and tibialis anterior muscles in both legs in CMT1A subjects with PMP22 gene duplication. Nine adult CMT1A patients, 18 years of age and older are enrolled into one of two cohorts in this trial. The first three subjects are enrolled at a low-minimally effective dose ($2.0 \times 10^{12}$ vg/kg) distributed bilaterally between both limbs in Cohort 1. An additional six subjects are enrolled with a 3-fold dose escalation ($6.0 \times 10^{12}$ vg/kg) in Cohort 2. Post-gene transfer monitoring includes follow up visits on days 7, 14, 30, 60, 90, 120, and 3 month intervals for the remainder of the trial extending for 2 years. Safety is a primary endpoint for this clinical gene transfer trial. Stopping criteria are based on development of unacceptable toxicity defined as the occurrence of any Grade II ocular or systemic toxicity not resolving after two weeks or any Grade III or higher toxicities. The secondary endpoint is efficacy defined as halting of the decline in abilities measured by the CMT Pediatric Scale (CMTPedS) at 2 years post gene transfer. The CMTPedS is an 11-item scale comprised of the Functional Dexterity Test, Nine-Hole Peg Test (SHPT), hand grip, foot plantarflexion, and foot dorsiflexion strength using handheld myometry, pinprick and vibration sensation, the Bruininks Oseretsky Test-Balance assessment, gait assessment, long jump, and six-minute walk test (6MWT). Exploratory outcome measures will include 100-meter timed test (100M), peroneal and ulnar CMAP amplitude and sensory and motor conduction velocities, a revised sensory testing to increase sensitivity for pinprick, touch-test and vibration assessments, visual analogue scales for pain and fatigue, Short Form Health Survey (SF-36) as Quality of Life measure, and circulating NT-3 levels.

Patients enrolled in the trial include any racial, ethnic, or gender background. Criteria for this disease have been defined and will follow the guidelines previously established by Shy et al. (Neurology 64: 1209-1214, 2001 and Neurology 70:378-383, 2008).

Inclusion Criteria for the study are as follows:

Adult subjects (>18 years) diagnosed with CMT1A

Must exhibit a 1.5 Mb duplication at 17p11.2 inclusive of the peripheral myelin protein 22 (PMP22) gene Males and females of any ethnic or racial group Must exhibit weakness of the ankle dorsiflexion muscle (should have full ROM against gravity but cannot maintain full dorsiflexion against gravity or able to stand heels 3 seconds or greater (Northstar criteria)]

Abnormal nerve conduction velocities

Ability to cooperate for clinical evaluation and repeat nerve conduction studies Willingness of sexually active subjects to practice a reliable method of contraception during the study Exclusion Criteria for the study are as follows:

Active viral infection based on clinical observations or serological evidence of HIV, or Hepatitis A, B or C infection Ongoing immunosuppressive therapy or immunosuppressive therapy within 6 months of starting the trial (e.g., corticosteroids, cyclosporine, tacrolimus, methotrexate, cyclophosphamide, intravenous immunoglobulin)

Persistent leukopenia or leukocytosis (WBC≤3.5 K/µL or ≥20.0 K/µL) or an absolute neutrophil count <1.5K/µL Subjects with AAV1 binding antibody titers ≥1:50 as determined by ELISA immunoassay Concomitant illness or requirement for chronic drug treatment that in the opinion of the PI creates unnecessary risks for gene transfer Ankle contractures or surgeries preventing proper muscle strength testing Pregnancy, breast feeding, or plans to become pregnant Other causes of neuropathy Limb surgery in the past six months

TABLE 5

Study Design

| Cohort | Dose (vg/kg) | *Patient Weight (kg) | *Conc. (vg/mL) | Volume/70 kg patient (mL) | Volume/leg (mL) | injections/leg (#) |
|---|---|---|---|---|---|---|
| 1. Low dose Bilateral (n = 3) | $2 \times 10^{12}$ | 70 | $1.5 \times 10^{13}$ | 9.33 | 4.67 | 5 |
| 2. High dose Bilateral (n = 6) | $6 \times 10^{12}$ | 70 | $1.5 \times 10^{13}$ | 28.00 | 14 | 14 |

*Table 5 provides an outline of the dosing plan based on a patient bodyweight of 70 Kg as an example. Dosing volumes are based on target product concentration of approximately $1.5 \times 10^{13}$ vg/ml.

Baseline Measures Prior to Injection (Day −30 to Day −1)

After obtaining written informed consent and completing hospital registration procedures, the following baseline medical procedures and measurements will be performed.

Medical history
Intake of concomitant medications
Physical exam
Chest X-ray
Echocardiogram
EKG
Hematology blood labs (CBC)
Coagulation parameters: Platelets, PT/INR, PTT
Clinical Chemistry blood labs: Bilirubin, Blood Urea Nitrogen (BUN), GGT,
Alkaline phosphatase, Alpha-fetoprotein (AFP), Creatinine, Amylase, Serum Protein Electrophoresis, Electrolytes, Glucose, Creatine Kinase
Urinalysis
Viral screen (hepatitis and HIV)
Pregnancy test (only females of childbearing age)
Blood Immunology: Neutralizing antibodies (AAV1) and ELISpots
(NT-3 and AAV1)
Serum for ELISA (circulating NT-3)
Efficacy Measures
Exploratory Measures
Photographs of injection site Pre-Injection Prednisolone Dose Prior to gene transfer, each patient will receive a dose of oral prednisone 1 mg/kg/day with a max of 60 mg/day, followed by a second dose the day of gene transfer. The subject will receive prednisone both 24 and 48 hours post-gene transfer for a total of 4 doses.

Protocol for Gene Transfer

Self-complementary AAV1 carrying a human NTF3 gene under the control of the tMCK promoter (scAAV1.tMCK.NTF3) is administered in a one-time bilateral intramuscular injection to the medial and lateral heads of the gastrocnemius and tibialis anterior (TA) muscles.

Gene Transfer Procedure

The gene transfer procedure is as follows:
The gene transfer infusion procedure is performed under sterile conditions.
Vector is delivered without diluent for a total of approximately 10 mL to 28 mL per patient (5 to 14 mL per limb, which is divided into 3 muscles).
Vector is delivered to the procedure room in pre-labeled syringes sealed in double leak-proof bags, carried in a designated labeled cooler.
A total of 5 mL to 14 mL of vector is administered to each and lateral heads of the gastroc and TA muscle in a total of 3 to 6 injections per muscle (each injection volume will be 0.5 to 1.0 ml). See schematic of injection sites in FIGS. 8A. and 8B.
The injections are at least 0.25 cm below the fascia with injections following a longitudinal axis of the muscle guided by ultrasound.
Each injection is approximately 1.5 cm apart.

In-Patient Monitoring

Following gene transfer injection, subjects return to a designated inpatient bed with close monitoring of vital signs and respiratory function. Vital signs are monitored approximately every hour for the first 4 hours, then every 4 hours until discharge. Safety is assessed by physical exam and laboratory evaluation. Subjects are given the third dose of oral prednisone (Day 1) and fourth and final dose of prednisone are given the following day (48 hours post injection, Day 2). Patients will be discharged approximately 48 hours after gene transfer (if no side effects are observed).

Out-Patient Monitoring

After discharge, patients return for follow up visits on days 7, 14, 30, 60, 90, 120, and 3 month intervals for the remainder of the trial extending for 2 years following gene transfer. Blood samples obtained at all visits are assessed for NT-3 protein expression as demonstrated with anti-NT-3 antibodies in a serum ELISA. Additionally, patients will be tested at visits 7, 9, 11, 13 and 14 for efficacy and exploratory measures. The serum ELISA are a direct measure of functional gene expression with secondary outcome measures demonstrating efficacy of the circulating transgene Primary Endpoint:

Safety is a primary endpoint for this clinical gene transfer trial. This is evaluated based on development of unacceptable toxicity defined as the occurrence of any one Grade III or higher, unanticipated, treatment-related toxicities.

Safety Measures

Safety will be measured at each study with a collection of height and weight, vital signs, physical exam and review of systems, and a battery of blood lab work. Lab work will include CBC, platelets, blood urea nitrogen (BUN), GGT, bilirubin, alkaline phosphatase, alpha-fetoprotein, creatinine, amylase, serum protein electrophoresis, electrolytes, glucose, PT/INR and PTT, CK, urinalysis. Immunology consists of neutralizing antibodies to AAV1 and ELISA for detection of antibodies to NT-3, ELISpots to detect T cell responses to AAV1 and NT-3. All adverse events will be recorded and assessed for relatedness to gene transfer.

Secondary Endpoint

The secondary endpoint of the clinical gene transfer trial is efficacy defined as halting of the decline in abilities measured by the CMT Pediatric Scale (CMTPedS) at 2 years post gene transfer.

Upper and lower limb muscle strength testing is conducted using hand held dynamometer for distal movements in the upper extremity (hand grip) and legs (foot dorsiflexion). The extremity for testing is immobilized for testing, which significantly improves reliability of foot isometric contraction measures (29). Upper limb function is measured with the 9-hole peg test (SHPT). Lower limb function is measured with the timed 10 meter run/walk (T10MW) test.

Exploratory Outcome Measures

Exploratory outcomes include 100-meter timed test (100M), peroneal and ulnar CMAP amplitude and sensory and motor conduction velocities, a revised sensory testing to increase sensitivity for pinprick, touch-test and vibration assessments, visual analogue scales for pain and fatigue, Short Form Health Survey (SF-36) as Quality of Life measure, and circulating NT-3 levels.

Electrophysiological testing includes measurement of ulnar sensory nerve amplitude and compound muscle action potential (CMAP) amplitude of the ulnar nerve (recorded from the abductor digiti minimi muscle) and the peroneal nerve (recorded from the tibialis anterior muscle) and sensory and motor conduction velocities. Peroneal CMAP amplitude from tibialis anterior has been shown to be a useful outcome measure for clinical trials in patients with CMT1A(30); and for upper limb motor symptoms ulnar CMAP amplitude has proven to be the most informative parameter(31). Foot and hand temperatures will be kept at 32-34° C. during these testing procedures. Visual analogue scales will be used for measure of pain and fatigue (32). The Short Form Health Survey (SF-36) are used as a quality life document to monitor and compare disease burden pre and post-treatment.

Patients are offered a financial incentive to undergo optional fascicular sural nerve biopsies. If elected, biopsies are obtained before the start of treatment (from left sural), and at the end of the study (from right sural). Biopsies are performed as an out-patient visit under local anesthetic. Tissues will be processed and examined to assess the effects of NT-3 on the myelinated fiber regeneration. In order to match the level of the pre and post treatment material in respect to the length of the entire nerve, the proximal end of an incision (2.5 cm in length), is placed precisely 10 cm above the Achilles tendon (8).

Statistical Analysis

Safety is a primary endpoint for this clinical gene transfer trial. This is will be evaluated based on development of unacceptable toxicity defined as the occurrence of any one Grade III or higher, unanticipated, treatment-related toxicities. Safety will be measured at each study with a collection of height and weight, vital signs, physical exam and review of systems, and a battery of blood lab work. Lab work will include CBC, platelets, blood urea nitrogen (BUN), GGT, bilirubin, alkaline phosphatase, alpha-fetoprotein, creatinine, amylase, serum protein electrophoresis, electrolytes, B12, glucose, PT/INR and PTT, CK, urinalysis. Immunology will consist of neutralizing antibodies to AAV1 and ELISA for detection of antibodies to NT-3, ELISpots to detect T cell responses to AAV1 and NT-3. All adverse events will be recorded and assessed for relatedness to gene transfer.

The main secondary outcome measure is defined as lack of decline in disease severity on the CMT Disease Pediatric Scale score (CMTPedS). The computerized scoring system of the CMTPedS uses z scores from a normative sample to determine the individuals score based on the number of standard deviations the patients performance differs from the healthy population. Scoring the CMTPedS is at a fixed age of 20 years for all patients throughout the study, which is necessary for two reasons. The first reason is that the original CMTPedS scale relies on normative values for individual scale items in the computation of the final score, but normative values do not exist for individuals over the age of 2030. The second reason is that, although a score comparing the child to healthy peers is essential for children who are still developing, it has the limitation of imposing a functional decline when the child has another birthday. Even if the child's raw score on the test does not change, the scoring criteria is designed to become more stringent as they age, reflecting the expected motor skill improvement typically seen in healthy kids. However, in a clinical trial of a degenerative disease, a halting of the actual progression would constitute a successful trial. Keeping the age of the reference control data consistent throughout the study allows for use of the validated scoring system built into the CMTPedS. It also allows for the observation of actual change on the assessment so that a halt in progression is detected.

The proportion of patients whose CMTPedS scores have improved or stayed the same over a two-year period using binomial tests are estimated with 95% confidence intervals. As an exploratory aim, the proportion of patients with a non-decline in each of the 11 items of the CMTPedS are estaimated separately, as well as in the 100 meter timed test (100M), CMAP amplitudes, the visual analog scale of pain intensity (VAS), scores on the Short Form Health Survey (SF-36), and circulating NT-3 levels. In addition, Pearson or Spearman correlation coefficients are used at each measurement point to assess the association between circulating NT-3 levels and each outcome measure. Because this study is in the preliminary stages, the p-values for multiple comparisons will not be adjusted. However, a sensitivity analysis is performed and indicates which associations are statistically significant after adjustment, based on the Bonferroni-Holm step-down procedure.

Based on longitudinal natural history data (31,32), a successful secondary outcome measure is defined as a halt in the rate of deterioration in a standardized composite score of hand grip and ankle dorsiflexion strength, time to complete the 9-hole peg test and time to walk/run 10 meters.

Example 5

Toxicology Study

The purpose of this study was to assess safety of a self-complementary adeno-associated viral (scAAV) vector expressing the human neurotrophin factor 3 (NTF3) cDNA under the control of a muscle specific tMCK promoter (scAAV1.tMCK.NTF3) in wild-type (C57BL/6) and Trembler (Tr$^J$) mice following a single intramuscular injection in the gastrocnemius muscle. The results of this report demonstrate that a single intramuscular injection in wild-type and trembler mice is safe and well tolerated up to 48 weeks post injection.

Test Animals

Wild-type C57BL/6 (negative control) and Tr$^J$ (test article) mice were injected intramuscularly with either vehicle (0.9% sterile saline) or $1 \times 10^{13}$ vg/kg of scAAV1.tMCK.NTF3 in a total volume of 50 μl. This strain of carrier mice is available from Jackson Laboratories (stock #000664) or Charles River (stock #027). Tr$^J$ mice are available from Jackson Laboratories (stock #002504).

Trembler mice were 8-10 weeks old at time of injection. Due to availability of animals and known breeding issues of the animal strain, a subset of animals was treated at 12 weeks of age.

A total of 88 (44 Male/44 Female) animals were included in the study. 44 animals (22 C57BL/6, 22 TrJ) were treated with saline control and 44 animals (22 C57BL/6, 22 TrJ) were treated with scAAV1.tMCK.NTF3 test article. Out of these numbers, half of the animals from each cohort were euthanized at 24 weeks post treatment and the remaining animals were euthanized at 48 weeks post treatment. Animals were uniquely identified by ear tags.

Study Design

To assess safety of the scAAV1.tMCK.NTF3 test article, 4-6 week old wild-type C57BL/6 and 8-12 week old $Tr^J$ mice were injected with either vehicle (0.9% sterile saline) or $1\times10^{13}$ vg/kg of scAAV1.tMCK.NTF3 in a total volume of 50 µl via a single IM injection in the left gastrocnemius muscle. Animals were observed daily throughout the course of the study for general health and morbidity. Checks for mortality were performed twice daily. Body mass was measured every 2 weeks. Functional testing for hypersensitivity (Hot Plate and Acoustic Startle testing) every 8 weeks. Behavioral tests (rotarod and wire hanging) were performed every 2 weeks.

Thermal sensitivity was tested started two weeks prior to injection followed by Day 0, and every 8 weeks using the Rodent Hot Plate Test. To perform the test, the animal was placed on the plate surface that has been maintained at a temperature of 55° C., and locomotion was constrained to a 100 cm² area using a 15 cm high Plexiglas wall surrounding the plate surface. A timer was started the moment the animal was placed on the heated surface, and the latency to respond time was recorded to 0.1 s via stopwatch. The following activities are considered a response to the heat stimulus: hind-paw lick or flick/flutter, an attempt to escape by jumping is also an acceptable response. The mouse was immediately removed when this response was observed.

Acoustic sensitivity was tested two weeks prior to injection followed by Day 0 (baseline), at the peak of serum NT-3 levels (8 to 12 weeks) and every 8 weeks after, all animals were tested for auditory hypersensitivity using the Acoustic Startle Test (AST). Startle reactivity was measured using a single startle chamber (SR-Lab, San Diego Instruments, San Diego, CA) as previously described in Beigneux et al., Behavioral Brain Res. 171:295-302, 2006.

The chamber consisted of a clear nonrestrictive Plexiglas cylinder resting on a platform inside a ventilated chamber. A high-frequency loudspeaker inside the chamber produced both a continuous background noise of 65 dB and the various acoustic stimuli. Vibrations of the Plexiglas cylinder caused by the whole-body startle response of the animal were transduced into analogue signals by a piezoelectric unit attached to the platform. The signals were then digitized and stored by the computer. Sixty-five readings were taken at 1 ms intervals, starting at stimulus onset, and the average amplitude ($V_{avg}$) was used to determine the acoustic startle response. A 65 dB background noise level was presented for a 5 min acclimation period and continued throughout the test session. All pre-pulse inhibition (PPI) test sessions consisted of startle trials (pulse alone), prepulse trials (prepulse+ pulse), and no-stimulus trials (no-stim). The pulse alone trial consisted of a 40 ms 120 dB pulse of broad-band noise. PPI was measured by prepulse+pulse trials that consisted of a 20 ms noise prepulse, 100 ms delay, and then a 40 ms 120 dB startle pulse. The acoustic prepulse intensities were 69, 73, and 81 dB. The no-stimulus trial consisted of background noise only. The test session began and ended with five presentations of the pulse alone trial; in between, each trial type was presented 10 times in pseudorandom order. There was an average of 15 s (range 12-30 s) between trials.

For the rotarod analysis, at least one week of training was needed to ensure that all subjects have learned the task to the same degree. In the accelerating rotation protocol, the animals were placed on a rod which accelerates to 5 rpm and then increases at 5 rpm/sec7. Animals undergo three trials per session which were averaged.

For the wire hanging analysis, the animals were placed by their four paws on a 2-mm diameter wire metal wire maintained horizontally 35 cm above a thick layer of soft bedding. The length of time until the mice fell from the wire were recorded and after each fall mice were given 1-minute recovery period. Each testing session consisted of three trials from which the scores were averaged.

At 22 and 46 weeks post-injection (2 weeks prior to euthanasia), blood was collected from the retro-orbital sinus for hematology studies (Erythrocyte count, Hematocrit, Hemoglobin, Leukocyte count, total and differential, Mean Corpuscular Hemoglobin, Mean Corpuscular Hemoglobin Concentration, Mean Corpuscular Volume, Mean Platelet Volume, Platelet Count, Reticulocyte Count). Clinical chemistries were analyzed for the following parameters: Alanine aminotransferase, Alkaline Phosphatase, Aspartate aminotransferase, Bilirubin (Total and Direct), Blood Urea nitrogen, Creatinine, Creatine Kinase, Glucose, Total Protein.

At 24 and 48 weeks post injection, blood was collected by intracardiac puncture with the serum used for immune studies. Serum samples were collected for anti-AAV1 and anti-NT-3 antibody titration for all animals in each cohort (regardless of treatment or gender). Serum samples were additionally used for ELISA assay of circulating NT-3 levels.

At 24 and 48 weeks post injection, the following tissues from $Tr^J$ animals were collected for histopathology analysis: gonad, brain, spleen, kidney, jejunum, colon, pancreas, heart, lung, stomach, liver, inguinal lymph nodes, spinal cord, gastrocnemius muscle (right and left), and gross lesions (if any). Tissues were fixed in 10% neutral buffered formalin, sectioned and stained with Hematoxylin and eosin. Histological analysis was performed by SNBL USA.

At 24 and 48 weeks post injection, tissue for in-house histopathology was collected for 6 animals per cohort (3M, 3F), with the exception of the $Tr^J$ control cohort (n=5, 3M, 2F). Mice were sacrificed and perfused transcardially with 4% paraformaldehyde in phosphate buffer (0.1M, pH 7.4). Lumbar spinal cord, dorsal root ganglions (DRGs) and the entire sciatic nerve segment (sciatic notch to popliteal fossa) were dissected. the proximal half of the sciatic segment in its in situ length and one lumbar DRG were transferred to glutaraldehyde fixative, processed for plastic embedding and 1-µm thick sectioning. The remainder of the sciatic nerve tissue and lumbar DRGs were cryo-protected in 30% sucrose, frozen in isopentane cooled in liquid nitrogen and cut in 12 µm sections for immunohistochemistry for detection of CGRP positivity in DRG neurons and axons (spinal cord and brain from TrJ mice were placed in 10% neutral buffered formalin.

TABLE 6

Study Design

| Cohort Number | Strain | Study Agent | Dose (vg/kg) | Treatment Day 0 | Sacrificial End-Points Week 24 | Week 48 | Extra |
|---|---|---|---|---|---|---|---|
| 6 High Dose | C57BL/6 | scAAV1.tMCK.NTF3 | $1 \times 10^{13}$ | Single IM injection to the gastroc muscle of a single leg | n = 10 (5M/5F) | n = 10 (5M/5F) | +2 (1M/1F) |
| 7 High Dose | Tr$^J$ | scAAV1.tMCK.NTF3 | $1 \times 10^{13}$ | | n = 10 (5M/5F) | n = 10 (5M/5F) | +2 (1M/1F) |
| 8 Control | C57BL/6 | Vehicle (0.9% Sterile Saline) | 0 | | n = 10 (5M/5F) | n = 10 (5M/5F) | +2 (1M/1F) |
| 0 Control | Tr$^J$ | Vehicle (0.9% Sterile Saline) | 0 | | n = 10 (5M/5F) | n = 10 (5M/5F) | +2 (1M/1F) |
| TOTAL MICE | | | | | N = 88 (44M/44F) | | |

Animal Dosing, Observation and Analysis

The animals indicated were dosed once on day 0 with a 50 µL volume via a single IM injection into the left gastrocnemius muscle. To perform accurate dosing, animals were anesthetized with isoflurane inhalation, for a minimum of 15 minutes. Doses were administered by direct injections into the left gastrocnemius. Care is taken to accurately deposit the entire vector dose into the muscle. After the dosing was performed, animals were observed until ambulatory and returned to the cage. Observations of each animal are performed daily for the whole duration of the study. Body mass is measured every 2 weeks. Mortality checks were performed twice daily.

At the appropriate age, mice were overdosed with Ketamine/Xylazine mixture (200 mg/kg/20 mg/kg). Blood was collected via heart puncture. Tissues were then collected and sent for analysis.

Body weights, mouse hematology and clinical chemistries are plotted for each cohort per time point. ELISA assays for anti-AAV1 circulating antibodies, anti-NT-3 circulating antibodies, and circulating NT-3 levels were performed for all end points. Hypersensitivity functional testing using the rodent hot plate and acoustic startle apparatus were performed every 8 weeks for all animals. Behavioral testing was performed every two weeks for rotarod and wire hanging tests for all animals. Formal histopathology on organs was performed for all animals. In-house histopathology on lumbar spinal cord and DRGs were performed on 6 mice per cohort (3M, 3F), with the exception of the Tr$^J$ cohort which included 5 animals (3M, 2F). Histopathology assessment included immunocytochemical distribution of CGRP positivity (in lumbar DRG neurons and spinal cord) and plastic embedding of sciatic nerves and DRG neurons for analysis of pathological changes.

Results

Morbidity and Mortality

All mice survived the injection procedure and an initial observation period passed without any signs of distress. Four Tr$^J$ animals died due to malfunction in the water delivery system. There were no test article related deaths.

Body Weights

The body weights of all mice in each group were measured every two weeks throughout the course of the study. All treatment groups kept gaining weight in a steady manner throughout the study.

In C57BL/6 male animals there was no significant differences between test article injected animals and controls. In female animals, weights were slightly higher in control animals as compared to test article injected animals. In the Tr$^J$ male animals, the saline treated cohort was significantly heavier than the NT-3 treated cohort. For female Tr$^J$ mice, there was no significant difference in body weights.

Hematology and Clinical Chemistries

There were no test article-related changes in the hematology parameters at the 22 and 46 or in the serum chemistry at the 24 and 48-week time points.

ELISA Assays

ELISA assays for anti-AAV1 antibodies, anti-NT-3 antibodies and circulating NT-3 were performed with serum samples collected during the 24 and 48 week necropsies.

To measure circulating anti-AAV1 antibodies, serum samples were collected at 24 and 48 weeks post vector administration and antibody titers were determined by binding Enzyme-Linked Immunosorbant Assay (ELISA), see Table 7 below. Animals treated with scAAV1.tMCK.NTF3 had elevated circulating antibodies to AAV1 capsid. Antibody titers were similar in both males and females at both time points. Positive titer (>1:50) was not detected in saline control treated animals.

TABLE 7

Median Circulation Serum Antibody Titers to AAV1 capsid from mice treated with scAAV1.tMCK.NT-3

| Time-Post Vector Administration | Treatment Group | | | |
|---|---|---|---|---|
| | Median | | Range | |
| | Male | Female | Male | Female |
| Group 1: Saline Control (0) | | | | |
| 24 weeks | <1:50 | <1:50 | <1:50 | <1:50 |
| 48 weeks | <1:50 | <1:50 | <1:50 | <1:50 |
| Group 2: scAAV1.tMCK.NT-3 Vector ($2.0 \times 10^{11}$) | | | | |
| 24 weeks | 1:25600 | 1:25600 | 1:25600-1:25600 | 1:25600-1:25600 |
| 48 weeks | 1:3200 | 1:12800 | 1:3200-1:25600 | 1:12800-1:25600 |

To measure anti-NT-3 circulating antibodies, serum samples were collected at 24 and 48 weeks post vector administration and antibody titers to NT-3 were determined by binding Enzyme-Linked Immunosorbant Assay (ELISA). All mice had antibody titers of <1:50 (considered negative) at 24 and 48 weeks post vector administration. See Table 8.

TABLE 8

Median Circulation Serum Antibody Titers to NT-3 peptide from mice treated with scAAV1.tMCK.NT-3

| Time-Post Vector Administration | Dose Level (vg) | | | |
|---|---|---|---|---|
| | Median | | Range | |
| | Male | Female | Male | Female |
| Group 1: Saline Control (0) | | | | |
| 24 weeks | <1:50 | <1:50 | <1:50 | <1:50 |
| 48 weeks | <1:50 | <1:50 | <1:50 | <1:50 |
| Group 2: scAAV1.tMCK.NT-3 Vector ($2.0 \times 10^{11}$) | | | | |
| 24 weeks | <1:50 | <1:50 | <1:50 | <1:50 |
| 48 weeks | <1:50 | <1:50 | <1:50 | <1:50 |

Circulating NT-3 levels were determined in serum samples of Tr$^J$ mice collected at 24 and 48 weeks post vector administration via standard binding ELISA assay. Intramuscular injection of scAAV1.tMCK.NTF3 vector resulted in robust expression and secretion of NT-3 Tr$^J$ mice at 24 and 48 weeks post vector administration. Table 9 shows the mean and standard deviations of serum NT-3 levels at 24 and 48 post-injection in Tr$^J$ from saline and vector injected groups. Gender had no effect on the circulating NT-3 levels.

TABLE 9

Circulating NT3 Serum Levels (ng/mL)

| Group | Dose (vg/kg) | Sex | 24 Weeks | | 48 Weeks | |
|---|---|---|---|---|---|---|
| | | | Mean | SD | Mean | SD |
| Saline | 0 | M | 0.000 | 0.000 | 0.019 | 0.038 |
| | | F | 0.003 | 0.004 | 0.000 | 0.000 |
| scAAV1.tMCK.NT-3 | $1.0 \times 10^{13}$ | M | 10.808 | 6.705 | 7.616 | 4.572 |
| | | F | 10.410 | 3.729 | 9.312 | 4.809 |

Hypersensitivity Testing

Thermal sensitivity testing was performed at baseline (before the treatment with either the test article of control saline) and every 8 weeks until 48 weeks post-injection in C57BL/6 and TrJ mice. There were no differences between control and vector injected mice in C57BL/6 and TrJ cohorts. There was also no significant difference in the withdrawal latencies between male and female mice in each cohort.

The results for the auditory sensitivity measurements performed in the acoustic startle test demonstrated that the AST was clearly inhibited by the pre-pulse at all intensities (69, 73 and 81 dB) and the level of inhibition was dependent upon the intensity of the pre-pulse in both wild type and TrJ mice. Treatment with the test article did not alter the PPI responses in the C57BL/6 wild type mice. The %-PPI was detectably lower in control article treated TrJ animals which was improved toward normalization in test article (NT-3) treated TrJ animals. This improvement in NT-3 treated Tr$^J$ animals was seen predominantly in the male animals.

Behavioral Testing

For the rotarod assessment, animals in the C57BL/6 cohort demonstrated no differences in rotarod functional testing regardless of treatment. Animals in the TrJ NT-3 treated cohort demonstrated significant improvement in rotarod performance as compared to control TrJ animals beginning at 16 weeks post-treatment which persisted through to endpoint.

For the wire hang assessment, animals in the C57BL/6 cohort demonstrated no differences in wire hanging functional testing regardless of treatment. Animals in the TrJ NT-3 treated cohorts demonstrated significant improvement in wire hanging ability as compared to control TrJ animals beginning at 28 weeks post-treatment which persisted to endpoint.

Histopathology

Formal histopathology was carried out. A listing of the organs and tissues analyzed are presented below in Table 10.

TABLE 10

List Organs examined for histology

| Organ/Tissue | Histo-pathology |
|---|---|
| Gonads | X |
| Brain | X |
| Spleen | X |
| Kidneys | X |
| Jejunum | X |
| Colon | X |
| Pancreas | X |
| Heart | X |
| Lung | X |
| Stomach | X |
| Liver | X |
| Inguinal lymph nodes | X |
| Spinal cord | X |
| Gastrocnemius muscle* | X |
| Gross lesions (if any) | X |

*Right and Left Gastrocnemius

Following euthanasia, lumbar spinal cord, dorsal root ganglions (DRGs), and the entire sciatic nerve (from sciatic notch to popliteal fossa) were removed and processed for histopathological evaluation. A list of the individual animals included for the in-house histopathology is shown in Table 11.

TABLE 11

In house histopathology outline following scAAV1.tMCK.NTF3 administered via intramuscular injection to the gastrocnemius muscle of Tr$^J$ and C57BL/6 mice

| Strain | ID Number | Gender | Article Injected | Strain | ID Number | Gender | Article Injected |
|---|---|---|---|---|---|---|---|
| | Endpoint: 24 weeks | | | | Endpoint: 48 weeks | | |
| Tr$^J$ | 3935 | F | 0.9% Sterile Saline | Tr$^J$ | 3901 | M | 0.9% Sterile Saline |
| | 3936 | F | | | 3902 | M | |
| | 3937 | F | | | 3903 | M | |
| | 3915 | M | | | 3928 | F | |
| | 3913 | M | | | 3943 | F | |
| | 3914 | M | | | | | |

TABLE 11-continued

In house histopathology outline following scAAV1.tMCK.NTF3 administered via intramuscular injection to the gastrocnemius muscle of Tr$^J$ and C57BL/6 mice

| Strain | ID Number | Gender | Article Injected | Strain | ID Number | Gender | Article Injected |
|---|---|---|---|---|---|---|---|
| | | | Endpoint: 24 weeks | | | | Endpoint: 48 weeks |
| Tr$^J$ | 3940 | F | scAAV1.tMCK.NTF3 | Tr$^J$ | 3904 | M | scAAV1.tMCK.NTF3 |
| | 3941 | F | | | 3905 | M | |
| | 3942 | F | | | 3906 | M | |
| | 3924 | M | | | 3930 | F | |
| | 3922 | M | | | 3931 | F | |
| | 3923 | M | | | 3932 | F | |
| C57BL/6 | 931 | F | 0.9% Sterile Saline | C57BL/6 | 926 | F | 0.9% Sterile Saline |
| | 931 | F | | | 927 | F | |
| | 933 | F | | | 928 | F | |
| | 942 | M | | | 937 | M | |
| | 943 | M | | | 939 | M | |
| | 946 | M | | | 940 | M | |
| C57BL/6 | 956 | F | scAAV1.tMCK.NTF3 | C57BL/6 | 951 | F | scAAV1.tMCK.NTF3 |
| | 957 | F | | | 952 | F | |
| | 958 | F | | | 953 | F | |
| | 964 | M | | | 959 | M | |
| | 965 | M | | | 960 | M | |
| | 966 | M | | | 963 | M | |

Immunocytochemical Analysis of CGRP Distribution

For immunocytochemical analysis of CGRP distribution, examination of cross-sections from lumbar spinal cord segments at 24 and 48 weeks post-injection was carried out. This analysis revealed no increase in CGRP reactivity with NT-3 in Tr$^J$ and C57BL/6 animals regardless of treatment article.

Pathological Changes in Plastic-Embedded Sections were analyzed. Plastic-embedded left sciatic nerves and left lumbar DRG neurons examined at 24 and 48 weeks post-injection showed no pathological changes in C57BL/6 animals. Age-related changes such as myelin corrugation/infoldings and outfoldings suggesting axonal atrophy were seen in both treatment cohorts of C57BL/6 animals at 48 weeks post-treatment. In Tr$^J$ animals treated with saline there was a notable dropout in myelinated fibers and numerous hypomyelinated or nude axons. Tr$^J$ animals treated with the test article show a visible increase in small myelinated fibers, myelin thickness and decrease in nude axons. There were not any adverse effects of NT-3 treatment in TrJ mice, as evidenced by lack of axonal sprouting within DRGs.

Overall, the absence of adverse treatment-related findings throughout the throughout the study in both C57BL/6 and Tr$^J$ animals indicates that the treatment was well tolerated through 48 weeks post injection.

Discussion

To assess safety of scAAV1.tMCK.NTF3 delivered via a single intramuscular injection, a toxicology study was designed including a total of 88 (44 Male/44 Female) animals. 44 animals (22 C57BL/6, 22 TrJ) were treated with 0.9% sterile saline control and 44 animals (22 C57BL/6, 22 TrJ) were treated with scAAV1.tMCK.NTF3 test article at a concentration of $1\times10^{13}$ vg/kg. Of these animals, half of the animals from each cohort were euthanized at 24 weeks post treatment and the remaining animals were euthanized at 48 weeks post treatment.

The data in this report demonstrate that treatment of animals with a dose 10-fold higher than the proposed clinical dose did not result in the manifestation of test article related adverse safety effects. Throughout the study, animals were observed daily for general health and morbidity, with mortality checks performed twice daily. Body mass of animals was measured every 2 weeks. Functional testing for hypersensitivity (thermal and acoustic) was performed every 8 weeks. Behavioral testing was performed every 2 weeks. All animals survived the injection procedure and initial observation period with no signs of distress. Due to a malfunction in the water delivery system there were 4 deaths in TrJ animals that were not related to administration of the test article. No other deaths were recorded in this study.

Following necropsy, blood hematology and clinical chemistries were measured and did not demonstrate any test article-related differences. Anti-AAV1 serum ELISAs were performed and demonstrated an expected increase in circulating antibodies in animals treated with the test article which was not gender specific. Anti-NT-3 serum ELISAs were performed with all animals demonstrating negative antibody titers for all timepoints. Circulating NT-3 levels were also measured for all treatment groups and were elevated only in test article treated animals. There was no gender-specific effect on circulating NT-3 levels. Thermal hypersensitivity testing revealed no treatment or gender specific changes in C57BL/6 or Tr$^J$ animals. Auditory sensitivity measurements revealed no test article related changes in C57BL/6 animals, but did demonstrate a deficit in control article treated Tr$^J$ animals with an improvement toward normalization in test article treated Tr$^J$ animals. This improvement was seen primarily in male Tr$^J$ animals. Rotarod assessment of motor control in C57BL/6 animals revealed no differences related to treatment with the test article. Test article treated TrJ animals demonstrated a significant improvement as compared to control Tr$^J$ animals beginning at 16 weeks post treatment. Similarly, wire hanging assessment revealed no differences in the C57BL/6 cohort related to the test article. Tr$^J$ animals treated with the test article demonstrated a significant improvement in wire hanging time beginning at 28 weeks post treatment which persisted to endpoint.

Tissues and organs collected from all cohorts at 24 and 48 weeks post treatment were evaluated. To summarize a minimal infiltration of mononuclear cells was observed in the test article-injected left gastrocnemius muscle in 3/4 Group 1 males and 4/5 group 1 females from the 24-week necropsy. However, similar infiltration was also observed in the gastrocnemius muscle that was non-injected in the remaining Group 1 female (animal 3942). This change was not observed in either the saline-injected left or non-injected right gastrocnemius muscles in any Group 2 (control) animals from the 24-week necropsy. In the 48-week necropsy animals, minimal infiltration of mononuclear cells was again observed in the test article-injected left gastrocnemius muscle of 2/5 group 1 males and 1/6 group 1 females. All other microscopic findings were randomly distributed across control and treated animals, were background findings for the species, or were considered incidental to test-article administration.

In-house histology was performed on lumbar spinal cord section, dorsal root ganglions and the sciatic nerve of a subset of animals (3M, 3F per group). Examination of cross-sections from lumbar spinal cord segments revealed no increase in CGRP activity with NT-3 in animals regardless of treatment. Pathology evaluation of plastic-embedded sciatic nerves and lumbar DRG neurons showed no changes in C57BL/6 animals beyond age-related differences. In $Tr^J$ animals, treatment with the test article resulted in improved pathology as evidenced by an increase in small myelinated fibers, increased myelin thickness and a decrease in nude axons. Lack of axonal sprouting in DRGs further support the safety of the test article.

Overall, the collected data presented in this study indicate that the test article scAAV1.tMCK.NTF3 injected directly into the gastrocnemius muscle by a single intramuscular injection at a dose of $1 \times 10^{13}$ vg/kg was well tolerated out to 48 weeks post injection in both male and female C57BL/6 wild-type and $Tr^J$ mice as evidenced by the multiple measures presented above.

REFERENCES

1. Lupski J R, de Oca-Luna R M, Slaugenhaupt S, et al. DNA duplication associated with Charcot-Marie-Tooth disease type 1A. Cell 1991; 66:219-232.
2. Saporta A S, Sottile S L, Miller L J, Feely S M, Siskind C E, Shy M E. Charcot-Marie-Tooth disease subtypes and genetic testing strategies. Ann Neurol 2011; 69:22-33.
3. Sahenk Z. Abnormal Schwann cell-axon interactions in CMT neuropathies. The effects of mutant Schwann cells on the axonal cytoskeleton and regeneration-associated myelination. Ann NY Acad Sci 1999; 883:415-426.
4. Verhamme C, de Haan R J, Vermeulen M, Baas F, de Visser M, van Schaik I N. Oral high dose ascorbic acid treatment for one year in young CMT1A patients: a randomised, double-blind, placebo-controlled phase II trial. BMC medicine 2009; 7:70.
5. Micallef J, Attarian S, Dubourg O, et al. Effect of ascorbic acid in patients with Charcot-Marie-Tooth disease type 1A: a multicentre, randomised, double-blind, placebo-controlled trial. Lancet Neurol 2009; 8:1103-1110.
6. Pareyson D, Reilly M M, Schenone A, et al. Ascorbic acid in Charcot-Marie-Tooth disease type 1A (CMT-TRIAAL and CMT-TRAUK): a double-blind randomised trial. Lancet Neurol 2011; 10:320-328.
7. Lewis R A, McDermott M P, Herrmann D N, et al. High-dosage ascorbic acid treatment in Charcot-Marie-Tooth disease type 1A: results of a randomized, double-masked, controlled trial. JAMA neurology 2013; 70:981-987.
8. Sahenk Z, Nagaraja H N, McCracken B S, et al. NT-3 promotes nerve regeneration and sensory improvement in CMT1A mouse models and in patients. Neurology 2005; 65:681-689.
9. de Waegh S M, Brady S T. Local control of axonal properties by Schwann cells: neurofilaments and axonal transport in homologous and heterologous nerve grafts. J Neurosci Res 1991; 30:201-212.
10. Yin X, Crawford T O, Griffin J W, et al. Myelin-associated glycoprotein is a myelin signal that modulates the caliber of myelinated axons. J Neurosci 1998; 18:1953-1962.
11. de Waegh S, Brady S T. Altered slow axonal transport and regeneration in a myelin-deficient mutant mouse: the trembler as an in vivo model for Schwann cell-axon interactions. J Neurosci 1990; 10:1855-1865.
12. de Waegh S M, Lee V M, Brady S T. Local modulation of neurofilament phosphorylation, axonal caliber, and slow axonal transport by myelinating Schwann cells. Cell 1992; 68:451-463.
13. Adlkofer K, Martini R, Aguzzi A, Zielasek J, Toyka K V, Suter U. Hypermyelination and demyelinating peripheral neuropathy in Pmp22-deficient mice. Nat Genet 1995; 11:274-280.
14. Adlkofer K, Frei R, Neuberg D H, Zielasek J, Toyka K V, Suter U. Heterozygous peripheral myelin protein 22-deficient mice are affected by a progressive demyelinating tomaculous neuropathy. J Neurosci 1997; 17:4662-4671.
15. Anzini P, Neuberg D H, Schachner M, et al. Structural abnormalities and deficient maintenance of peripheral nerve myelin in mice lacking the gap junction protein connexin 32. J Neurosci 1997; 17:4545-4551.
16. Bosio A, Bussow H, Adam J, Stoffel W. Galactosphingolipids and axono-glial interaction in myelin of the central nervous system. Cell Tissue Res 1998; 292:199-210.
17. Martini R, Zielasek J, Toyka K V, Giese K P, Schachner M. Protein zero (P0)-deficient mice show myelin degeneration in peripheral nerves characteristic of inherited human neuropathies. Nat Genet 1995; 11:281-286.
18. Sahenk Z, Chen L. Abnormalities in the axonal cytoskeleton induced by a connexin32 mutation in nerve xenografts. J Neurosci Res 1998; 51:174-184.
19. Sahenk Z, Chen L, Freimer M. A novel PMP22 point mutation causing HNPP phenotype: studies on nerve xenografts. Neurology 1998; 51:702-707.
20. Sahenk Z, Chen L, Mendell J R. Effects of PMP22 duplication and deletions on the axonal cytoskeleton. Ann Neurol 1999; 45:16-24.
21. Sanchez I, Hassinger L, Paskevich P A, Shine H D, Nixon R A. Oligodendroglia regulate the regional expansion of axon caliber and local accumulation of neurofilaments during development independently of myelin formation. J Neurosci 1996; 16:5095-5105.
22. Sahenk Z, Serrano-Munuera C, Chen L, Kakabadze I, Najagara H N. Evidence for impaired axonal regeneration in PMP22 duplication: studies in nerve xenografts. J Peripher Nery Syst 2003; 8:116-127.
23. Ramer M S, Bishop T, Dockery P, et al. Neurotrophin-3-mediated regeneration and recovery of proprioception following dorsal rhizotomy. Molecular and cellular neurosciences 2002; 19:239-249.
24. Helgren M E, Cliffer K D, Torrento K, et al. Neurotrophin-3 administration attenuates deficits of pyridoxine-induced large-fiber sensory neuropathy. J Neurosci 1997; 17:372-382.
25. Mizisin A P, Calcutt N A, Tomlinson D R, Gallagher A, Fernyhough P. Neurotrophin-3 reverses nerve conduction velocity deficits in streptozotocin-diabetic rats. J Peripher Nery Syst 1999; 4:211-221.

26. Mizisin A P, Kalichman M W, Bache M, Dines K C, DiStefano P S. NT-3 attenuates functional and structural disorders in sensory nerves of galactose-fed rats. J Neuropathol Exp Neurol 1998; 57:803-813.
27. Shy M E, Blake J, Krajew ski K, et al. Reliability and validity of the CMT neuropathy score as a measure of disability. Neurology 2005; 64:1209-1214.
28. Shy M E, Chen L, Swan E R, et al. Neuropathy progression in Charcot-Marie-Tooth disease type 1A. Neurology 2008; 70:378-383.
29. Solari A, Laura M, Salsano E, Radice D, Pareyson D. Reliability of clinical outcome measures in Charcot-Marie-Tooth disease. Neuromuscul Disord 2008; 18:19-26.
30. Komyathy K, Neal S, Feely S, et al. Anterior tibialis CMAP amplitude correlations with impairment in CMT1A. Muscle & nerve 2013; 47:493-496.
31. Mannil M, Solari A, Leha A, et al. Selected items from the Charcot-Marie-Tooth (CMT) Neuropathy Score and secondary clinical outcome measures serve as sensitive clinical markers of disease severity in CMT1A patients. Neuromuscul Disord 2014; 24:1003-1017.
32. Pareyson D, Schenone A, Fabrizi G M, et al. A multi-center, randomized, double-blind, placebo-controlled trial of long-term ascorbic acid treatment in Charcot-Marie-Tooth disease type 1A (CMT-TRIAAL): the study protocol [EudraCT no.: 2006-000032-27]. Pharmacological research 2006; 54:436-441.
33. Piscosquito G, Reilly M M, Schenone A, et al. Responsiveness of clinical outcome measures in Charcot-Marie-Tooth disease. European journal of neurology: the official journal of the European Federation of Neurological Societies 2015; 22:1556-1563.

While the present invention has been described in terms of specific embodiments, it is understood that variations and modifications will occur to those skilled in the art. Accordingly, only such limitations as appear in the claims should be placed on the invention.

What is claimed:

1. A nucleic acid comprising a nucleotide sequence that is at least 90% identical to SEQ ID NO: 11.

2. The nucleic acid of claim 1, wherein the nucleic acid comprises the nucleotide sequence set out in SEQ ID NO: 11.

3. A recombinant adeno-associated virus particle (rAAV) comprising the nucleic acid of claim 2, wherein the rAAV is infectious.

4. The rAAV particle of claim 3, wherein the rAAV particle is AAV-1, AAV-2, AAV-3, AAV-4, AAV-5, AAV-6, AAV-7, AAV-8, AAV-9, AAV-10, AAV-11, or AAVrh.74.

5. A recombinant adeno-associated virus particle (rAAV) comprising the nucleic acid of claim 1, wherein the rAAV is infectious.

6. The rAAV particle of claim 5, wherein the AAV DNA in the rAAV genome is from AAV-1, AAV-2, AAV-3, AAV-4, AAV-5, AAV-6, AAV-7, AAV-8, AAV-9, AAV-10, AAV-11, AAVrh.74.

7. A composition comprising the rAAV particle of claim 5 and a pharmaceutically acceptable carrier.

8. A method of treating a muscle wasting disorder or neuropathy in a human subject in need thereof comprising the step of administering to the human subject the nucleic acid of claim 1.

9. The method of claim 8, wherein the route of administration is intramuscular injection.

10. The method of claim 8 wherein the nucleic acid is a recombinant adeno-associated virus (rAAV) genome, and the rAAV is administered at a dose that results in sustained expression of NT-3 polypeptide.

11. The method of claim 8, wherein the rAAV is administered using an intramuscular route and the dose of the rAAV administered is about $1.5 \times 10^{12}$ vg/kg to about $6.5 \times 10^{12}$ vg/kg, about $2 \times 10^{12}$ vg/kg to about $6 \times 10^{12}$ vg/kg, about $2 \times 10^{12}$ vg/kg, about $4 \times 10^{12}$ vg/kg, or about $6 \times 10^{12}$ vg/kg.

12. The method of claim 8, wherein the rAAV is administered using an intramuscular injection at a concentration of about $2 \times 10^{13}$ vg/ml administered using 3 to 6 injections per muscle of about 0.5 to 1 ml.

13. The method of claim 8, wherein the rAAV is administered using an intramuscular injection at a concentration of about $2 \times 10^{13}$ vg/ml administered using multiple injections at a total volume of about 5 to 14 ml.

14. The method of claim 8, wherein the subject is suffering from Charcot-Marie-Tooth (CMT) neuropathy.

15. The method of claim 14, wherein the subject has the genetic variant Val30Met, Ile107Val, or Ser77Tyr.

16. The method claim 8, wherein the subject is suffering from a transthyretin amyloid neuropathy, an acquired neuropathy caused by cancer, diabetes mellitus, human immunodeficiency virus (HIV) infection, thyroid disorder, hypothyroidism, hypoglycemia, uremia, renal insufficiency, hepatic dysfunction, hepatic failure, polycythemia, connective tissue disorders, lyme disease, celiac disease, leprosy, porphyria, Sjogren's syndrome, poliomyelitis, acromegaly, disorders of lipid/glycolipid metabolism, West Nile syndrome, amyloidosis, mitochondrial disorders, dysproteinemic disorders, monoclonal gammapathy of undetermined significance (MGUS), POEMS syndrome, nutritional/vitamin deficiency, vitamin B12 deficiency, vitamin E deficiency, copper deficiency, hereditary myopathy, peripheral neuropathy, toxic neuropathy, autoimmune peripheral polyneuropathy, acute inflammatory demyelinating polyradiculoneuropathy (AIDP), chronic inflammatory demyelinating polyradiculoneuropathy (CIDP), vasculitic mononeuritis multiplex, paraneuropathy, idiopathic ganglionitis, amyotrophic lateral sclerosis, multifocal motor conduction lock neuropathy, lower motor neuron syndrome, neuromuscular disease, muscular atrophy, drug-induced myopathy, sarcopenia, cachexia, type II muscle fiber atrophy, age-related muscular atrophy or an acquired autoimmune primary muscle disorder.

17. A method of improving muscle strength or stimulating muscle growth in a human subject in need thereof comprising the step of administering to the human subject the nucleic acid of claim 1.

18. The method of claim 17, wherein the route of administration is intramuscular injection.

19. The method of claim 17, wherein the improvement in the muscle strength is measured as a decrease in composite score on CMT Pediatric Scale (CMTPeds) or as a decrease in disease progression over a two year time period.

20. The method of claim 17, wherein the nucleic acid is a recombinant adeno-associated virus (rAAV) genome, and the rAAV is administered at a dose that results in sustained expression of NT-3 polypeptide.

21. The method of claim 17, wherein the rAAV is administered using an intramuscular route and the dose of the rAAV administered is about $1.5 \times 10^{12}$ vg/kg to about $6.5 \times 10^{12}$ vg/kg, about $2 \times 10^{12}$ vg/kg to about $6 \times 10^{12}$ vg/kg, about $2 \times 10^{12}$ vg/kg, about $4 \times 10^{12}$ vg/kg, or about $6 \times 10^{12}$ vg/kg.

22. The method of claim 17, wherein the rAAV is administered using an intramuscular injection at a concentration of about $2 \times 10^{13}$ vg/ml administered using 3 to 6 injections per muscle of about 0.5 to 1 ml.

23. The method of claim 17, wherein the rAAV is administered using an intramuscular injection at a concentration of about $2 \times 10^{13}$ vg/ml administered using multiple injections at a total volume of about 5 to 14 ml.

24. The method of claim 17, wherein the subject is suffering from Charcot-Marie-Tooth (CMT) neuropathy.

25. The method of claim 24, wherein the subject has the genetic variant Val30Met, Ile107Val, or Ser77Tyr.

26. The method claim 17, wherein the subject is suffering from a transthyretin amyloid neuropathy, an acquired neuropathy caused by cancer, diabetes mellitus, human immunodeficiency virus (HIV) infection, thyroid disorder, hypothyroidism, hypoglycemia, uremia, renal insufficiency, hepatic dysfunction, hepatic failure, polycythemia, connective tissue disorders, lyme disease, celiac disease, leprosy, porphyria, Sjogren's syndrome, poliomyelitis, acromegaly, disorders of lipid/glycolipid metabolism, West Nile syndrome, amyloidosis, mitochondrial disorders, dysproteinemic disorders, monoclonal gammapathy of undetermined significance (MGUS), POEMS syndrome, nutritional/vitamin deficiency, vitamin B12 deficiency, vitamin E deficiency, copper deficiency, hereditary myopathy, peripheral neuropathy, toxic neuropathy, autoimmune peripheral polyneuropathy, acute inflammatory demyelinating polyradiculoneuropathy (AIDP), chronic inflammatory demyelinating polyradiculoneuropathy (CIDP), vasculitic mononeuritis multiplex, paraneuropathy, idiopathic ganglionitis, amyotrophic lateral sclerosis, multifocal motor conduction lock neuropathy, lower motor neuron syndrome, neuromuscular disease, muscular atrophy, drug-induced myopathy, sarcopenia, cachexia, type II muscle fiber atrophy, age-related muscular atrophy or an acquired autoimmune primary muscle disorder.

* * * * *

SEQUENCE LISTING

<160> NUMBER OF SEQ ID NOS: 11

<210> SEQ ID NO 1
<211> LENGTH: 774
<212> TYPE: DNA
<213> ORGANISM: Homo sapiens
<220> FEATURE:
<221> NAME/KEY: misc_feature
<223> OTHER INFORMATION: hNT3

<400> SEQUENCE: 1

```
atgtccatct tgttttatgt gatatttctc gcttatctcc gtggcatcca aggtaacaac      60
atggatcaaa ggagtttgcc agaagactcg ctcaattccc tcattattaa gctgatccag     120
gcagatattt tgaaaaacaa gctctccaag cagatggtgg acgttaagga aaattaccag     180
agcaccctgc ccaaagctga ggctccccga gagccggagc ggggagggcc cgccaagtca     240
gcattccagc cggtgattgc aatggacacc gaactgctgc gacaacagag acgctacaac     300
tcaccgcggg tcctgctgag cgacagcacc cccttggagc cccgcccttt gtatctcatg     360
gaggattacg tgggcagccc cgtggtggcg aacagaacat cacggcggaa acggtacgcg     420
gagcataaga gtcaccgagg ggagtactcg gtatgtgaca gtgagagtct gtgggtgacc     480
gacaagtcat cggccatcga cattcgggga caccaggtca cggtgctggg ggagatcaaa     540
acgggcaact ctcccgtcaa acaatatttt tatgaaacgc gatgtaagga agccaggccg     600
gtcaaaaacg gttgcagggg tattgatgat aaacactgga actctcagtg caaaacatcc     660
caaacctacg tccgagcact gacttcagag aacaataaac tcgtgggctg gcggtggata     720
cggatagaca cgtcctgtgt gtgtgccttg tcgagaaaaa tcggaagaac atga           774
```

<210> SEQ ID NO 2
<211> LENGTH: 270
<212> TYPE: PRT
<213> ORGANISM: Homo sapiens
<220> FEATURE:
<221> NAME/KEY: MISC_FEATURE
<223> OTHER INFORMATION: NT-3 amino acid sequence

<400> SEQUENCE: 2

```
Met Val Thr Phe Ala Thr Ile Leu Gln Val Asn Lys Val Met Ser Ile
1               5                   10                  15

Leu Phe Tyr Val Ile Phe Leu Ala Tyr Leu Arg Gly Ile Gln Gly Asn
```

```
                 20                  25                  30
Asn Met Asp Gln Arg Ser Leu Pro Glu Asp Ser Leu Asn Ser Leu Ile
             35                  40                  45

Ile Lys Leu Ile Gln Ala Asp Ile Leu Lys Asn Lys Leu Ser Lys Gln
 50                  55                  60

Met Val Asp Val Lys Glu Asn Tyr Gln Ser Thr Leu Pro Lys Ala Glu
 65                  70                  75                  80

Ala Pro Arg Glu Pro Glu Arg Gly Gly Pro Ala Lys Ser Ala Phe Gln
                 85                  90                  95

Pro Val Ile Ala Met Asp Thr Glu Leu Leu Arg Gln Gln Arg Arg Tyr
            100                 105                 110

Asn Ser Pro Arg Val Leu Leu Ser Asp Ser Thr Pro Leu Glu Pro Pro
            115                 120                 125

Pro Leu Tyr Leu Met Glu Asp Tyr Val Gly Ser Pro Val Val Ala Asn
            130                 135                 140

Arg Thr Ser Arg Arg Lys Arg Tyr Ala Glu His Lys Ser His Arg Gly
145                 150                 155                 160

Glu Tyr Ser Val Cys Asp Ser Glu Ser Leu Trp Val Thr Asp Lys Ser
                165                 170                 175

Ser Ala Ile Asp Ile Arg Gly His Gln Val Thr Val Leu Gly Glu Ile
            180                 185                 190

Lys Thr Gly Asn Ser Pro Val Lys Gln Tyr Phe Tyr Glu Thr Arg Cys
            195                 200                 205

Lys Glu Ala Arg Pro Val Lys Asn Gly Cys Arg Gly Ile Asp Asp Lys
            210                 215                 220

His Trp Asn Ser Gln Cys Lys Thr Ser Gln Thr Tyr Val Arg Ala Leu
225                 230                 235                 240

Thr Ser Glu Asn Asn Lys Leu Val Gly Trp Arg Trp Ile Arg Ile Asp
                245                 250                 255

Thr Ser Cys Val Cys Ala Leu Ser Arg Lys Ile Gly Arg Thr
            260                 265                 270

<210> SEQ ID NO 3
<211> LENGTH: 714
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: tMCK Promoter

<400> SEQUENCE: 3
ccactacggg tctaggctgc ccatgtaagg aggcaaggcc tggggacacc cgagatgcct      60
ggttataatt aaccccaaca cctgctgccc ccccccccc aacacctgct gcctgagcct     120
gagcggttac cccaccccgg tgcctgggtc ttaggctctg tacaccatgg aggagaagct     180
cgctctaaaa ataaccctgt ccctggtgga tccactacgg gtctatgctg cccatgtaag     240
gaggcaaggc ctggggacac ccgagatgcc tggttataat taaccccaac acctgctgcc     300
cccccccccc caacacctgc tgcctgagcc tgagcggtta ccccaccccg gtgcctgggt     360
cttaggctct gtacaccatg gaggagaagc tcgctctaaa aataaccctg tccctggtgg     420
accactacgg gtctaggctg cccatgtaag gaggcaaggc ctggggacac ccgagatgcc     480
tggttataat taaccccaac acctgctgcc cccccccccc aacacctgct gcctgagcct     540
gagcggttac cccaccccgg tgcctgggtc ttaggctctg tacaccatgg aggagaagct     600
```

```
cgctctaaaa ataaccctgt ccctggtcct ccctggggac agcccctcct ggctagtcac      660
accctgtagg ctcctctata taacccaggg gcacaggggc tgcccccggg tcac            714

<210> SEQ ID NO 4
<211> LENGTH: 106
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 5'ITR

<400> SEQUENCE: 4
ctgcgcgctc gctcgctcac tgaggccgcc cgggcaaagc ccgggcgtcg ggcgaccttt       60
ggtcgcccgg cctcagtgag cgagcgagcg cgcagagagg gagtgg                    106

<210> SEQ ID NO 5
<211> LENGTH: 133
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Chimeric Intron

<400> SEQUENCE: 5
gtaagtatca aggttacaag acaggtttaa ggagaccaat agaaactggg cttgtcgaga       60
cagagaagac tcttgcgttt ctgataggca cctattggtc ttactgacat ccactttgcc     120
tttctctcca cag                                                        133

<210> SEQ ID NO 6
<211> LENGTH: 5
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Kozak Sequence:

<400> SEQUENCE: 6 ccacc                                                                   5

<210> SEQ ID NO 7
<211> LENGTH: 200
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: POLY A sequence

<400> SEQUENCE: 7
ggggatccag acatgataag atacattgat gagtttggac aaaccacaac tagaatgcag       60
tgaaaaaaat gctttatttg tgaaatttgt gatgctattg ctttatttgt aaccattata     120
agctgcaata aacaagttaa caacaacaat tgcattcatt ttatgtttca ggttcagggg     180
gaggtgtggg aggttttttc                                                 200

<210> SEQ ID NO 8
```

```
<211> LENGTH: 128
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 3'ITR

<400> SEQUENCE: 8 aggaaccoct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgc                                                            128

<210> SEQ ID NO 9
<211> LENGTH: 861
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: AMP R Sequence

<400> SEQUENCE: 9
atgagtattc aacatttccg tgtcgccctt attccctttt ttgcggcatt ttgccttcct    60 gttttgctc  acccagaaac gctggtgaaa gtaaaagatg ctgaagatca gttgggtgca   120
cgagtgggtt acatcgaact ggatctcaac agcggtaaga tccttgagag ttttcgcccc   180
gaagaacgtt ttccaatgat gagcactttt aaagttctgc tatgtggcgc ggtattatcc   240
cgtattgacg ccgggcaaga gcaactcggt cgccgcatac actattctca gaatgacttg   300
gttgagtact caccagtcac agaaaagcat cttacggatg gcatgacagt aagagaatta   360
tgcagtgctg ccataaccat gagtgataac actgcggcca acttacttct gacaacgatc   420
ggaggaccga aggagctaac cgcttttttg cacaacatgg gggatcatgt aactcgcctt   480
gatcgttggg aaccggagct gaatgaagcc ataccaaacg acgagcgtga ccacgatg    540 cctgtagcaa tggcaacaac gttgcgcaaa ctattaactg gcgaactact tactctagct   600
tcccggcaac aattaataga ctggatggag gcggataaag ttgcaggacc acttctgcgc   660
tcggcccttc cggctggctg gtttattgct gataaatctg gagccggtga gcgtgggtct   720
cgcggtatca ttgcagcact ggggccagat ggtaagccct cccgtatcgt agttatctac   780
acgacgggga gtcaggcaac tatggatgaa cgaaatagac agatcgctga gataggtgcc   840
tcactgatta agcattggta a                                             861

<210> SEQ ID NO 10
<211> LENGTH: 668
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: pBR322 Ori

<400> SEQUENCE: 10
gtagaaaaga tcaaaggatc ttcttgagat cctttttttc tgcgcgtaat ctgctgcttg    60
caaacaaaaa aaccaccgct accagcggtg gtttgtttgc cggatcaaga gctaccaact   120 cttttccga  aggtaactgg cttcagcaga gcgcagatac caaatactgt ccttctagtg   180
```

```
tagccgtagt taggccacca cttcaagaac tctgtagcac cgcctacata cctcgctctg    240
ctaatcctgt taccagtggc tgctgccagt ggcgataagt cgtgtcttac cgggttggac    300
tcaagacgat agttaccgga taaggcgcag cggtcgggct gaacggggg ttcgtgcaca     360 cagcccagct tggagcgaac gacctacacc gaactgagat acctacagcg tgagctatga    420
gaaagcgcca cgcttcccga agggagaaag gcggacaggt atccggtaag cggcagggtc    480
ggaacaggag agcgcacgag ggagcttcca gggggaaacg cctggtatct ttatagtcct    540
gtcgggtttc gccacctctg acttgagcgt cgatttttgt gatgctcgtc aggggggcgg    600
agcctatgga aaaacgccag caacgcggcc ttttacggt tcctggcctt ttgctggcct     660
tttgctca                                                             668

<210> SEQ ID NO 11
<211> LENGTH: 5884
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: sc pAAV.tMCK.NT3 vector full Sequence

<400> SEQUENCE: 11
cagcagctgc gcgctcgctc gctcactgag gccgcccggg caaagcccgg gcgtcgggcg     60
acctttggtc gcccggcctc agtgagcgag cgagcgcgca gagagggagt ggggttaacc    120
aattggcggc cgcaaacttg catgccccac tacgggtcta ggctgcccat gtaaggaggc    180
aaggcctggg gacacccgag atgcctggtt ataattaacc ccaacacctg ctgcccccc     240 ccccccaaca cctgctgcct gagcctgagc ggttacccca ccccggtgcc tgggtcttag    300
gctctgtaca ccatggagga gaagctcgct ctaaaaataa ccctgtccct ggtggatcca    360
ctacgggtct atgctgccca tgtaaggagg caaggcctgg ggacacccga gatgcctggt    420
tataattaac cccaacacct gctgccccc cccccccaac acctgctgcc tgagcctgag    480
cggttacccc accccggtgc ctgggtctta ggctctgtac accatggagg agaagctcgc    540
tctaaaaata accctgtccc tggtggacca ctacgggtct aggctgccca tgtaaggagg    600
caaggcctgg ggacacccga gatgcctggt tataattaac cccaacacct gctgccccc     660 ccccccaaca cctgctgcct gagcctgagc ggttacccca ccccggtgcc tgggtcttag    720
gctctgtaca ccatggagga gaagctcgct ctaaaaataa ccctgtccct ggtcctccct    780
ggggacagcc cctcctggct agtcacaccc tgtaggctcc tctatataac caggggcac     840 aggggctgcc cccgggtcac ctgcagaagt tggtcgtgag gcactgggca ggtaagtatc    900
aaggttacaa gacaggttta aggagaccaa tagaaactgg gcttgtcgag acagagaaga    960
ctcttgcgtt tctgataggc acctattggt cttactgaca tccactttgc ctttctctcc   1020
acaggtgtcc actcccagtt caattacagc gcgtggtacc tgcagggata tccaccatgt   1080
ccatcttgtt ttatgtgata tttctcgctt atctccgtgg catccaaggt aacaacatgg   1140
atcaaaggag tttgccagaa gactcgctca attccctcat tattaagctg atccaggcag   1200
atattttgaa aaacaagctc tccaagcaga tggtggacgt taaggaaaat taccagagca    1260
ccctgcccaa agctgaggct cccgagagc ggagcggggg agggcccgcc aagtcagcat      1320 tccagcggt gattgcaatg gacaccgaac tgctgcgaca acagagacgc tacaactcac    1380
cgcgggtcct gctgagcgac agcacccct tggagccccc gccttgtat ctcatggagg     1440
```

```
attacgtggg cagccccgtg gtggcgaaca gaacatcacg gcggaaacgg tacgcggagc    1500
ataagagtca ccgaggggag tactcggtat gtgacagtga gagtctgtgg gtgaccgaca    1560
agtcatcggc catcgacatt cggggacacc aggtcacggt gctggggag atcaaaacgg     1620 gcaactctcc cgtcaaacaa tatttttatg aaacgcgatg taaggaagcc aggccggtca    1680
aaaacggttg caggggtatt gatgataaac actggaactc tcagtgcaaa acatcccaaa    1740
cctacgtccg agcactgact tcagagaaca ataaactcgt gggctggcgg tggatacgga    1800
tagacacgtc ctgtgtgtgt gccttgtcga gaaaaatcgg aagaacatga ggcggccgcg    1860
gggatccaga catgataaga tacattgatg agtttggaca aaccacaact agaatgcagt    1920
gaaaaaaatg ctttatttgt gaaatttgtg atgctattgc tttatttgta accattataa    1980
gctgcaataa acaagttaac aacaacaatt gcattcattt tatgtttcag gttcaggggg    2040
aggtgtggga ggttttttcg gcgcgcctct agagcatggc tacgtagata agtagcatgg    2100
cgggttaatc attaactaca aggaacccct agtgatggag ttggccactc cctctctgcg    2160
cgctcgctcg ctcactgagg ccgggcgacc aaaggtcgcc cgacgcccgg gctttgcccg    2220
ggcggcctca gtgagcgagc gagcgcgcca gctggcgtaa tagcgaagag gcccgcaccg    2280
atcgcccttc ccaacagttg cgcagcctga atggcgaatg gaattccaga cgattgagcg    2340
tcaaaatgta ggtatttcca tgagcgtttt tcctgttgca atggctggcg gtaatattgt    2400
tctggatatt accagcaagg ccgatagttt gagttcttct actcaggcaa gtgatgttat    2460
tactaatcaa agaagtattg cgacaacggt taatttgcgt gatggacaga ctcttttact    2520
cggtggcctc actgattata aaaacacttc tcaggattct ggcgtaccgt tcctgtctaa    2580 aatccccttta atcggcctcc tgtttagctc ccgctctgat tctaacgagg aaagcacgtt    2640
atacgtgctc gtcaaagcaa ccatagtacg cgccctgtag cggcgcatta agcgcggcgg    2700
gtgtggtggt tacgcgcagc gtgaccgcta cacttgccag cgccctagcg cccgctcctt    2760
tcgctttctt cccttccttt ctcgccacgt tcgccggctt tccccgtcaa gctctaaatc    2820 ggggggctccc tttagggttc cgatttagtg ctttacggca cctcgacccc aaaaaacttg    2880
attagggtga tggttcacgt agtgggccat cgccctgata acggtttttt cgccctttga    2940
cgttggagtc cacgttcttt aatagtggac tcttgttcca aactggaaca acactcaacc    3000
ctatctcggt ctattctttt gatttataag ggattttgcc gatttcggcc tattggttaa    3060
aaaatgagct gatttaacaa aaatttaacg cgaatttaa caaaatatta acgtttacaa     3120
tttaaatatt tgcttataca atcttcctgt ttttggggct tttctgatta tcaaccgggg    3180
tacatatgat tgacatgcta gttttacgat taccgttcat cgattctctt gtttgctcca    3240
gactctcagg caatgacctg atagcctttg tagagacctc tcaaaaatag ctaccctctc    3300
cggcatgaat ttatcagcta gaacggttga atatcatatt gatggtgatt tgactgtctc    3360
cggcctttct cacccgtttg aatctttacc tacacattac tcaggcattg catttaaaat    3420
atatgagggt tctaaaaatt tttatccttg cgttgaaata aaggcttctc ccgcaaaagt    3480
attacagggt cataatgttt ttggtacaac cgatttagct ttatgctctg aggctttatt    3540
gcttaatttt gctaattctt tgccttgcct gtatgattta ttggatgttg gaattcctga    3600
tgcggtattt tctccttacg catctgtgcg gtatttcaca ccgcatatgg tgcactctca    3660
gtacaatctg ctctgatgcc gcatagttaa gccagccccg acaccgcca acacccgctg    3720 acgcgccctg acgggcttgt ctgctcccgg catccgctta cagacaagct gtgaccgtct    3780
ccgggagctg catgtgtcag aggttttcac cgtcatcacc gaaacgcgcg agacgaaagg    3840
```

```
gcctcgtgat acgcctattt ttataggtta atgtcatgat aataatggtt tcttagacgt    3900
caggtggcac ttttcgggga aatgtgcgcg gaaccccctat ttgtttattt ttctaaatac   3960
attcaaatat gtatccgctc atgagacaat aaccctgata aatgcttcaa taatattgaa   4020
aaaggaagag tatgagtatt caacatttcc gtgtcgccct tattccctttt tttgcggcat  4080 tttgccttcc tgttttttgct cacccagaaa cgctggtgaa agtaaaagat gctgaagatc  4140
agttgggtgc acgagtgggt tacatcgaac tggatctcaa cagcggtaag atccttgaga  4200
gttttcgccc cgaagaacgt tttccaatga tgagcacttt taaagttctg ctatgtggcg   4260
cggtattatc ccgtattgac gccgggcaag agcaactcgg tcgccgcata cactattctc   4320
agaatgactt ggttgagtac tcaccagtca cagaaaagca tcttacggat ggcatgacag   4380
taagagaatt atgcagtgct gccataacca tgagtgataa cactgcggcc aacttacttc   4440
tgacaacgat cggaggaccg aaggagctaa ccgcttttttt gcacaacatg ggggatcatg   4500
taactcgcct tgatcgttgg gaaccggagc tgaatgaagc cataccaaac gacgagcgtg   4560
acaccacgat gcctgtagca atggcaacaa cgttgcgcaa actattaact ggcgaactac   4620
ttactctagc ttcccggcaa caattaatag actggatgga ggcggataaa gttgcaggac   4680
cacttctgcg ctcggccctt ccggctggct ggtttattgc tgataaatct ggagccggtg   4740
agcgtgggtc tcgcggtatc attgcagcac tggggccaga tggtaagccc tcccgtatcg   4800
tagttatcta cacgacgggg agtcaggcaa ctatggatga acgaaataga cagatcgctg   4860
agataggtgc ctcactgatt aagcattggt aactgtcaga ccaagtttac tcatatatac   4920
tttagattga tttaaaactt catttttaat ttaaaaggat ctaggtgaag atcctttttg   4980
ataatctcat gaccaaaatc ccttaacgtg agttttcgtt ccactgagcg tcagaccccg   5040
tagaaaagat caaaggatct tcttgagatc cttttttttct gcgcgtaatc tgctgcttgc   5100
aaacaaaaaa accaccgcta ccagcggtgg tttgtttgcc ggatcaagag ctaccaactc   5160
tttttccgaa ggtaactggc ttcagcagag cgcagatacc aaatactgtc cttctagtgt   5220
agccgtagtt aggccaccac ttcaagaact ctgtagcacc gcctacatac ctcgctctgc   5280
taatcctgtt accagtggct gctgccagtg gcgataagtc gtgtcttacc gggttggact   5340
caagacgata gttaccggat aaggcgcagc ggtcgggctg aacggggggt tcgtgcacac   5400
agcccagctt ggagcgaacg acctacaccg aactgagata cctacagcgt gagctatgag   5460
aaagcgccac gcttcccgaa gggagaaagg cggacaggta tccggtaagc ggcagggtcg   5520
gaacaggaga gcgcacgagg gagcttccag ggggaaacgc ctggtatctt tatagtcctg   5580
tcgggtttcg ccacctctga cttgagcgtc gatttttgtg atgctcgtca ggggggcgga   5640
gcctatggaa aaacgccagc aacgcggcct ttttacggtt cctggccttt tgctggcctt   5700
ttgctcacat gttctttcct gcgttatccc ctgattctgt ggataaccgt attaccgcct   5760
ttgagtgagc tgataccgct cgccgcagcc gaacgaccga gcgcagcgag tcagtgagcg   5820
aggaagcgga agagcgccca atacgcaaac cgcctctccc cgcgcgttgg ccgattcatt   5880
aatg                                                                5884
```